(12) United States Patent
Bansal

(10) Patent No.: US 9,926,366 B2
(45) Date of Patent: Mar. 27, 2018

(54) METHODS OF TREATING A HEMOLYTIC DISORDER COMPRISING ADMINISTERING ANTI-PROPERDIN ANTIBODIES

(71) Applicant: NOVELMED THERAPEUTICS, INC., Cleveland, OH (US)

(72) Inventor: Rekha Bansal, Solon, OH (US)

(73) Assignee: NOVELMED THERAPEUTICS, INC., Cleveland, OH (US)

( * ) Notice: Subject to any disclaimer, the term of this patent is extended or adjusted under 35 U.S.C. 154(b) by 219 days.

(21) Appl. No.: 14/433,587

(22) PCT Filed: Oct. 4, 2013

(86) PCT No.: PCT/US2013/063401
§ 371 (c)(1),
(2) Date: Apr. 3, 2015

(87) PCT Pub. No.: WO2014/055835
PCT Pub. Date: Apr. 10, 2014

(65) Prior Publication Data
US 2016/0122419 A1    May 5, 2016

Related U.S. Application Data

(60) Provisional application No. 61/709,796, filed on Oct. 4, 2012.

(51) Int. Cl.
*A61K 39/395* (2006.01)
*C07K 16/18* (2006.01)

(52) U.S. Cl.
CPC .......... *C07K 16/18* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,679,345 A | 10/1997 | Sanfilippo et al. | |
| 6,333,034 B1 | 12/2001 | Gupta-Bansal et al. | |
| 7,365,167 B2 | 4/2008 | Watkins et al. | |
| 7,423,128 B2 | 9/2008 | Gazit-Bornstein et al. | |
| 2003/0198636 A1 | 10/2003 | Gupta-Bansal et al. | |
| 2004/0137513 A1 | 7/2004 | Devaux et al. | |
| 2004/0137514 A1 | 7/2004 | Steenbakkers | |
| 2004/0140265 A1 | 7/2004 | Lihme | |
| 2004/0208888 A1 | 10/2004 | Frank et al. | |
| 2006/0093599 A1 | 5/2006 | Gazit-Bornstein et al. | |
| 2006/0292141 A1 | 12/2006 | Holers et al. | |
| 2007/0041972 A1 | 2/2007 | Rother et al. | |
| 2007/0112177 A1 | 5/2007 | Hedrick et al. | |
| 2008/0025976 A1 | 1/2008 | Le et al. | |
| 2008/0124278 A1 | 5/2008 | Taylor et al. | |
| 2008/0233113 A1 | 9/2008 | Bansal | |
| 2009/0017031 A1 | 1/2009 | Fung | |
| 2009/0117126 A1 | 5/2009 | Adams et al. | |
| 2009/0214538 A1 | 8/2009 | Fung et al. | |
| 2009/0269326 A1 | 10/2009 | Epstein et al. | |
| 2010/0021416 A1 | 1/2010 | Lichter et al. | |
| 2010/0124555 A1 | 5/2010 | Crescence et al. | |
| 2010/0226928 A1 | 9/2010 | Dani | |
| 2010/0263061 A1 | 10/2010 | Song | |
| 2011/0008340 A1 | 1/2011 | Bansal | |
| 2011/0027292 A1 | 2/2011 | Warne et al. | |
| 2013/0071384 A1 | 3/2013 | Andya et al. | |
| 2014/0005367 A1 | 1/2014 | Morichika et al. | |
| 2014/0056888 A1 | 2/2014 | Zhou et al. | |
| 2014/0186348 A1 | 7/2014 | Bansal | |

FOREIGN PATENT DOCUMENTS

| | | |
|---|---|---|
| CN | 1596313 A | 3/2005 |
| JP | 2007-501021 A | 1/2007 |
| JP | 2008-500012 A | 1/2008 |
| WO | WO-99/10009 A1 | 3/1999 |
| WO | WO-03/074726 A2 | 9/2003 |
| WO | WO-2005/007809 A2 | 1/2005 |
| WO | WO-2006/052591 A2 | 5/2006 |
| WO | WO-2006/128006 A1 | 11/2006 |
| WO | WO-2008/154018 A2 | 12/2008 |
| WO | WO-2009/110918 A1 | 9/2009 |
| WO | WO-2010/054403 A1 | 5/2010 |
| WO | WO-2011/015602 A2 | 2/2011 |
| WO | WO-2011/109494 A2 | 9/2011 |
| WO | WO-2011/112850 A2 | 9/2011 |
| WO | WO-2013/152024 A1 | 10/2013 |

OTHER PUBLICATIONS

Rudikoff et al., Proc Natl Acad Sci USA 79: 1979-1983 (1982).*
Colman, Research in Immunology 145: 33-36, 1994.*
Kussie et al., J. Immunol. 152: 146-152, 1994.*
Chen et al., EMBO J., 14: 2784-2794, 1995.*
Bokesch et al., "Anti-human properdin monoclonal antibodies block activation of the alternative pathway in a model of cardiopulmonary bypass," Anesthesiology, American Society of Anesthesiologists, Philadelphia, PA. 91(3A): A717 (1999).
"Gliatech Receives Allowance of U.S. Patent Claims for Anti-Properdin Technology," <http://www.evaluategroup.com?Universal/View.aspx?type=Story&id=17022>, dated Oct. 3, 2001, retrieved on Dec. 10, 2013 (2 pages).
Gupta-Bansal et al., "Inhibition of complement alternative pathway function with anti-properdin monoclonal antibodies," Mol Immunol. 37(5):191-201 (2000).
Holers, "The spectrum of complement alternative pathway-mediated diseases," Immunol Rev. 223:300-316 (2008).
Kimura et al., "Gene targeting of properdin ameliorates disease development in the K/BxN mouse serum transfer model of arthritis," Mol Immunol. 45(16):4112 (2008) (Abstract Only).

(Continued)

*Primary Examiner* — Phillip Gambel
(74) *Attorney, Agent, or Firm* — Clark & Elbing LLP

(57) ABSTRACT

A method of treating a hemolytic disorder in a subject in need thereof includes administering to the subject a therapeutically effective amount of an antibody that binds to a component of alternative pathway C3 convertase and selectively inhibits C3a, C5a, C3b, C5b, and C5b-9 produced exclusively by the alternative pathway, without inhibiting any of the classical pathway's ability to produce C3a, C5a, C3b, C5b, and C5b-9.

16 Claims, 13 Drawing Sheets

(56) References Cited

OTHER PUBLICATIONS

Lindorfer et al., "A novel approach to preventing the hemolysis of paroxysmal nocturnal hemoglobinuria: both complement-mediated cytolysis and C3 deposition are blocked by a monoclonal antibody specific for the alternative pathway of complement," Blood. 115(11):2283-91 (2010).

NCBI GenBank Direct Submission Accession No. S9126, "properdin precursor [validated]—human," <http://www.ncbi.nlm.nih.gov/protein/529126?report=genpept>, retrieved on Dec. 10, 2012 (3 pages).

Noris et al., "STEC-HUS, atypical HUS and TTP are all diseases of complement activation," Nat Rev Nephrol. 8(11):622-33 (2012).

Parker, "Management of paroxysmal nocturnal hemoglobinuria in the era of complement inhibitory therapy," Hematology Am Soc Hematol Educ Program. 2011:21-9 (2011).

Perdikoulis et. al, "Expression and characterisation of the thrombospondin type I repeats of human properdin," Biochim Biophys Acta. 1548(2):266-77 (2001).

Pugsley et al., "Inhibitors of the complement system currently in development for cardiovascular disease," Cardiovasc Toxicol. 3(1):43-69 (2003).

Risitano et al., "C3-mediated extravascular hemolysis in paroxysmal nocturnal hemoglobinuria: an in vitro model to dissect complement C3 activation comparing the effects of complement inhibitors eculizumab, 3E7 and TT30 on C3 fragment processing and hemolysis of PNH erythrocytes," Blood 116(21):279 (2010). Abstract only.

Supplementary Partial European Search Report for European Application No. 13843349.5, dated May 2, 2016 (8 pages).

Warne, "Development of high concentration protein biopharmaceuticals: the use of platform approaches in formulation development," Eur J Pharm Biopharm. 78(2):208-12 (2011).

Natsume et. al, "Engineered antibodies of IgG1/IgG3 mixed isotype with enhanced cytotoxic activities," Cancer Res. 68(10):3863-72 (2008).

Beck et. al, "Therapeutic antibodies and related products: choosing the right structure for success," Med Sci (Paris). 25(12):1024-32 (2009). (English Abstract).

Salfeld, "Isotype selection in antibody engineering," Nat Biotechnol. 25(12):1369-72 (2007).

Labrijn et. al, "When binding is enough: nonactivating antibody formats," Curr Opin Immunol. 20(4):479-85 (2008).

\* cited by examiner

C3b Formation

Inhibition of AP-Mediated C3b Deposition by Anti-Bb in Human Serum.

Inhibition of AP-Mediated C3b Deposition by Anti-P.

Inhibition of AP-Mediated C3b Deposition Anti-C3b

Inhibition of AP-Mediated C3b Deposition onto LPS by Anti-P2.

C5b-9 Formation

Inhibition of AP-Mediated C5b-9 Deposition by Anti-Bb in Human Serum.

Inhibition of AP-Mediated C5b-9 Deposition by Anti-P1.

Inhibition of AP-Mediated C5b-9 Deposition onto LPS by Anti-C3b

Inhibition of AP-Mediated C5b-9 Deposition onto LPS by Anti-P2

Antibodies of the Invention Prevent LDH Release In Vivo in a Model of PNH

SEQUENCE LISTING

<160> NUMBER OF SEQ ID NOS: 75

<210> SEQ ID NO 1
<211> LENGTH: 10
<212> TYPE: PRT
<213> ORGANISM: Mus musculus

<400> SEQUENCE: 1

Gly Tyr Ile Phe Thr Asn Tyr Pro Ile His
1               5                   10

<210> SEQ ID NO 2
<211> LENGTH: 17
<212> TYPE: PRT
<213> ORGANISM: Mus musculus

<400> SEQUENCE: 2

Phe Ile Asp Pro Gly Gly Tyr Asp Glu Pro Asp Glu Arg Phe Arg
1               5                   10                  15

Asp

<210> SEQ ID NO 3
<211> LENGTH: 9
<212> TYPE: PRT
<213> ORGANISM: Mus musculus

<400> SEQUENCE: 3

Arg Gly Gly Gly Tyr Tyr Leu Asp Tyr
1               5

<210> SEQ ID NO 4
<211> LENGTH: 12
<212> TYPE: PRT
<213> ORGANISM: Mus musculus

<400> SEQUENCE: 4

Gly Phe Ser Leu Ser Thr Ser Gly Met Gly Val Gly
1               5                   10

<210> SEQ ID NO 5
<211> LENGTH: 16
<212> TYPE: PRT
<213> ORGANISM: Mus musculus

<400> SEQUENCE: 5

His Ile Trp Trp Asp Asp Val Lys Ser Tyr Asn Pro Ala Leu Lys Ser
1               5                   10                  15

<210> SEQ ID NO 6
<211> LENGTH: 10
<212> TYPE: PRT
<213> ORGANISM: Mus musculus

<400> SEQUENCE: 6

Ile Gly Asp Gly Tyr Tyr Ser Phe Asp Tyr
1               5                   10

<210> SEQ ID NO 7
<211> LENGTH: 10
<212> TYPE: PRT
<213> ORGANISM: Mus musculus

<400> SEQUENCE: 7

Gly Tyr Ile Phe Thr Thr Tyr Pro Ile His

```
<210> SEQ ID NO 8
<211> LENGTH: 17
<212> TYPE: PRT
<213> ORGANISM: Mus musculus

<400> SEQUENCE: 8

Phe Ile Asp Pro Gly Gly Gly Tyr Asp Glu Pro Asp Asp Lys Phe Arg
1               5                   10                  15
Asp

<210> SEQ ID NO 9
<211> LENGTH: 9
<212> TYPE: PRT
<213> ORGANISM: Mus musculus

<400> SEQUENCE: 9

Arg Gly Asp Gly Tyr Tyr Phe Asp Tyr
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Gly Asp Ser Ile Ser Ser Gly Gly His Tyr Trp Ser
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11

Tyr Ile Tyr Tyr Ser Gly Ser Ser Tyr Tyr Asn Pro Ser Leu Lys Ser
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Thr Gly Asp Tyr Phe Asp Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gly Phe Thr Phe Ser Asn Tyr Gly Ile His
1               5                   10
```

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

```
Val Ile Trp Tyr Asp Gly Asn Asn Lys Tyr Tyr Ala Asp Ser Val Lys
1               5                   10                  15

Gly
```

<210> SEQ ID NO 15
<211> LENGTH: 20
<212> TYPE: PRT
<213> ORGANISM: Artificial Sequence
<220> FEATURE:
<223> OTHER INFORMATION: Synthetic Construct

<400> SEQUENCE: 15

```
Gly Gly Tyr Tyr Asp Ser Arg Gly Tyr Tyr Thr Pro Tyr Tyr Tyr Tyr
1               5                   10                  15

Gly Met Asp Val
            20
```

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

```
Gly Phe Thr Phe Ser Cys Tyr Gly Met His
1               5                   10
```

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

```
Val Ile Trp Tyr Asp Gly Ser Asn Lys Tyr Tyr Ala Asp Ser Val Lys
1               5                   10                  15

Gly
```

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

```
Ala Gly Gly Ala Thr Ala Met Asp Val
1               5
```

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 19

Gly Tyr Thr Leu Thr Glu Leu Ser Met His
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Gly Phe Asp Pro Glu Asp Gly Glu Thr Ile Tyr Ala Gln Met Phe Gln
1               5                   10                  15

Gly

<210> SEQ ID NO 21
<211> LENGTH: 19
<212> TYPE: PRT
<213> ORGANISM: Artificial Sequence
<220> FEATURE:
<223> OTHER INFORMATION: Synthetic Construct

<400> SEQUENCE: 21

Gly Thr Tyr Tyr Asp Ile Leu Thr Gly Pro Ser Tyr Tyr Tyr Gly
1               5                   10                  15

Leu Gly Val

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Gly Gly Ser Ile Ser Ile Tyr Tyr Trp Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Tyr Ile Tyr Tyr Ser Gly Ser Thr Asn Tyr Asn Pro Ser Leu Lys Ser
1               5                   10                  15

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Trp Asn Tyr Gly Asp Ala Phe Asp Ile
1               5

<210> SEQ ID NO 25
<211> LENGTH: 11
<212> TYPE: PRT
<213> ORGANISM: Oryctolagus cuniculus
```

<400> SEQUENCE: 25

Gly Phe Ser Phe Ser Ser Gly Tyr Trp Ile Phe
1               5                   10

<210> SEQ ID NO 26
<211> LENGTH: 18
<212> TYPE: PRT
<213> ORGANISM: Oryctolagus cuniculus

<400> SEQUENCE: 26

Gly Ile Tyr Ser Gly Ser Ser Gly Thr Thr Tyr Tyr Ala Asn Trp Ala
1               5                   10                  15

Lys Gly

<210> SEQ ID NO 27
<211> LENGTH: 14
<212> TYPE: PRT
<213> ORGANISM: Oryctolagus cuniculus

<400> SEQUENCE: 27

Ser Val Asp Gly Ile Asp Ser Tyr Asp Ala Ala Phe Asn Leu
1               5                   10

<210> SEQ ID NO 28
<211> LENGTH: 10
<212> TYPE: PRT
<213> ORGANISM: Mus musculus

<400> SEQUENCE: 28

Gly Tyr Thr Phe Thr Asn Tyr Trp Ile His
1               5                   10

<210> SEQ ID NO 29
<211> LENGTH: 17
<212> TYPE: PRT
<213> ORGANISM: Mus musculus

<400> SEQUENCE: 29

Tyr Ile Asn Pro Asn Thr Gly Tyr Asn Asp Tyr Asn Gln Lys Phe Lys
1               5                   10                  15

Asp

<210> SEQ ID NO 30
<211> LENGTH: 12
<212> TYPE: PRT
<213> ORGANISM: Mus musculus

<400> SEQUENCE: 30

Gly Gly Gln Leu Gly Leu Arg Arg Ala Met Asp Tyr
1               5                   10

<210> SEQ ID NO 31
<211> LENGTH: 10
<212> TYPE: PRT
<213> ORGANISM: Oryctolagus cuniculus

<400> SEQUENCE: 31

Gly Phe Asp Leu Ser Thr Tyr Ala Met Ser
1               5                   10

<210> SEQ ID NO 32
<211> LENGTH: 17

```
<212> TYPE: PRT
<213> ORGANISM: Oryctolagus cuniculus

<400> SEQUENCE: 32

Ala Val Ser Ala Thr Thr Gly Asn Thr Tyr Tyr Ala Thr Trp Ala Lys
1               5                   10                  15

Gly

<210> SEQ ID NO 33
<211> LENGTH: 12
<212> TYPE: PRT
<213> ORGANISM: Oryctolagus cuniculus

<400> SEQUENCE: 33

Tyr Ala Ser Ser Gly Val Gly Thr Tyr Phe Asp Leu
1               5                   10

<210> SEQ ID NO 34
<211> LENGTH: 10
<212> TYPE: PRT
<213> ORGANISM: Oryctolagus cuniculus

<400> SEQUENCE: 34

Gly Phe Ser Leu Ser Asn Tyr His Leu Gly
1               5                   10

<210> SEQ ID NO 35
<211> LENGTH: 16
<212> TYPE: PRT
<213> ORGANISM: Oryctolagus cuniculus

<400> SEQUENCE: 35

Val Ile Thr Tyr Gly Gly Ser Thr Tyr Tyr Ala Ser Trp Val Lys Gly
1               5                   10                  15

<210> SEQ ID NO 36
<211> LENGTH: 10
<212> TYPE: PRT
<213> ORGANISM: Oryctolagus cuniculus

<400> SEQUENCE: 36

Arg Asp Ser Gly Gly Tyr His Leu Asp Leu
1               5                   10

<210> SEQ ID NO 37
<211> LENGTH: 10
<212> TYPE: PRT
<213> ORGANISM: Oryctolagus cuniculus

<400> SEQUENCE: 37

Gly Phe Ser Leu Ser Ser Asn Ala Ile Asn
1               5                   10

<210> SEQ ID NO 38
<211> LENGTH: 16
<212> TYPE: PRT
<213> ORGANISM: Oryctolagus cuniculus

<400> SEQUENCE: 38

Thr Ile His Thr Asn Thr Lys Thr Tyr Tyr Ala Thr Trp Ala Arg Gly
1               5                   10                  15

<210> SEQ ID NO 39
<211> LENGTH: 3
```

```
<212> TYPE: PRT
<213> ORGANISM: Oryctolagus cuniculus

<400> SEQUENCE: 39

Ala Asp Leu
1

<210> SEQ ID NO 40
<211> LENGTH: 10
<212> TYPE: PRT
<213> ORGANISM: Mus musculus

<400> SEQUENCE: 40

Gly Tyr Thr Phe Thr Ser Tyr Trp Ile Asn
1               5                   10

<210> SEQ ID NO 41
<211> LENGTH: 17
<212> TYPE: PRT
<213> ORGANISM: Mus musculus

<400> SEQUENCE: 41

Asp Ile Tyr Pro Val Arg Gly Ile Thr Asn Tyr Ser Glu Lys Phe Lys
1               5                   10                  15

Asn

<210> SEQ ID NO 42
<211> LENGTH: 11
<212> TYPE: PRT
<213> ORGANISM: Mus musculus

<400> SEQUENCE: 42

Gly Asn Phe Gly Asn Phe Asp Ala Met Asp Tyr
1               5                   10

<210> SEQ ID NO 43
<211> LENGTH: 11
<212> TYPE: PRT
<213> ORGANISM: Mus musculus

<400> SEQUENCE: 43

Arg Ala Ser Gln Asp Ile Ser Phe Phe Leu Asn
1               5                   10

<210> SEQ ID NO 44
<211> LENGTH: 7
<212> TYPE: PRT
<213> ORGANISM: Mus musculus

<400> SEQUENCE: 44

Tyr Thr Ser Arg Tyr His Ser
1               5

<210> SEQ ID NO 45
<211> LENGTH: 9
<212> TYPE: PRT
<213> ORGANISM: Mus musculus

<400> SEQUENCE: 45

Gln His Gly Asn Thr Leu Pro Trp Thr
1               5

<210> SEQ ID NO 46
<211> LENGTH: 11
```

```
<212> TYPE: PRT
<213> ORGANISM: Mus musculus

<400> SEQUENCE: 46

Lys Ala Ser Gln Asp Val Ser Asp Ala Val Ala
1               5                   10

<210> SEQ ID NO 47
<211> LENGTH: 7
<212> TYPE: PRT
<213> ORGANISM: Mus musculus

<400> SEQUENCE: 47

Ser Pro Ser Tyr Arg Tyr Thr
1               5

<210> SEQ ID NO 48
<211> LENGTH: 9
<212> TYPE: PRT
<213> ORGANISM: Mus musculus

<400> SEQUENCE: 48

Gln Gln His Tyr Ser Thr Pro Trp Thr
1               5

<210> SEQ ID NO 49
<211> LENGTH: 16
<212> TYPE: PRT
<213> ORGANISM: Mus musculus

<400> SEQUENCE: 49

Arg Ser Ser Gln Ser Leu Val His Ser Asn Gly Asn Thr Tyr Leu His
1               5                   10                  15

<210> SEQ ID NO 50
<211> LENGTH: 16
<212> TYPE: PRT
<213> ORGANISM: Mus musculus

<400> SEQUENCE: 50

Arg Ser Ser Gln Ser Leu Val His Ser Asn Gly Asn Thr Tyr Leu His
1               5                   10                  15

<210> SEQ ID NO 51
<211> LENGTH: 9
<212> TYPE: PRT
<213> ORGANISM: Mus musculus

<400> SEQUENCE: 51

Ser Gln Asn Thr His Val Pro Arg Thr
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Arg Ala Ser Gln Asp Ile Ser Asn Tyr Leu Ala
1               5                   10

<210> SEQ ID NO 53
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 53

Ala Ala Ser Thr Leu Gln Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Gln Lys Tyr Asn Ser Ala Pro Trp Thr
1               5

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Arg Ala Ser Gln Gly Ile Ser Asn Tyr Leu Ala
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Ala Ala Ser Thr Leu Gln Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Lys Tyr Asp Ser Ala Pro Trp Thr
1               5

<210> SEQ ID NO 58
<211> LENGTH: 11
<212> TYPE: PRT
<213> ORGANISM: Oryctolagus cuniculus

<400> SEQUENCE: 58

Gln Ala Ser Asp Asn Ile Tyr Ser Leu Leu Ala
1               5                   10

<210> SEQ ID NO 59
<211> LENGTH: 7
<212> TYPE: PRT
<213> ORGANISM: Oryctolagus cuniculus
```

<400> SEQUENCE: 59

Arg Ala Ser Thr Leu Ala Ser
1               5

<210> SEQ ID NO 60
<211> LENGTH: 12
<212> TYPE: PRT
<213> ORGANISM: Oryctolagus cuniculus

<400> SEQUENCE: 60

Gln Gln His Tyr Asp Tyr Asn Tyr Leu Asp Val Ala
1               5                   10

<210> SEQ ID NO 61
<211> LENGTH: 11
<212> TYPE: PRT
<213> ORGANISM: Mus musculus

<400> SEQUENCE: 61

Arg Ala Ser Lys Ser Ile Ser Lys Tyr Leu Ala
1               5                   10

<210> SEQ ID NO 62
<211> LENGTH: 7
<212> TYPE: PRT
<213> ORGANISM: Mus musculus

<400> SEQUENCE: 62

Ser Gly Ser Thr Leu Gln Ser
1               5

<210> SEQ ID NO 63
<211> LENGTH: 9
<212> TYPE: PRT
<213> ORGANISM: Mus musculus

<400> SEQUENCE: 63

Gln Gln His Asp Glu Tyr Pro Trp Thr
1               5

<210> SEQ ID NO 64
<211> LENGTH: 11
<212> TYPE: PRT
<213> ORGANISM: Oryctolagus cuniculus

<400> SEQUENCE: 64

Gln Ala Ser Glu Asn Ile Tyr Ser Arg Leu Ala
1               5                   10

<210> SEQ ID NO 65
<211> LENGTH: 7
<212> TYPE: PRT
<213> ORGANISM: Oryctolagus cuniculus

<400> SEQUENCE: 65

Tyr Ala Ser Asp Leu Ala Ser
1               5

<210> SEQ ID NO 66
<211> LENGTH: 13
<212> TYPE: PRT
<213> ORGANISM: Oryctolagus cuniculus

<400> SEQUENCE: 66

His Ser Tyr Tyr Trp Asn Ser Ala Tyr Ser Asp Asn Thr
1               5                   10

<210> SEQ ID NO 67
<211> LENGTH: 11
<212> TYPE: PRT
<213> ORGANISM: Oryctolagus cuniculus

<400> SEQUENCE: 67

Gln Ala Ser Glu Asn Ile Tyr Ser Tyr Leu Ala
1               5                   10

<210> SEQ ID NO 68
<211> LENGTH: 7
<212> TYPE: PRT
<213> ORGANISM: Oryctolagus cuniculus

<400> SEQUENCE: 68

Lys Ala Ser Tyr Leu Ala Ser
1               5

<210> SEQ ID NO 69
<211> LENGTH: 12
<212> TYPE: PRT
<213> ORGANISM: Oryctolagus cuniculus

<400> SEQUENCE: 69

Leu Ser Thr Ile Ala Ser Ala Ser Asn Phe Asp Ala
1               5                   10

<210> SEQ ID NO 70
<211> LENGTH: 13
<212> TYPE: PRT
<213> ORGANISM: Oryctolagus cuniculus

<400> SEQUENCE: 70

Gln Ser Ser Gln Ser Val Tyr Arg Ser Asn Asn Val Ala
1               5                   10

<210> SEQ ID NO 71
<211> LENGTH: 7
<212> TYPE: PRT
<213> ORGANISM: Oryctolagus cuniculus

<400> SEQUENCE: 71

Glu Ala Ser Ser Leu Ala Ser
1               5

<210> SEQ ID NO 72
<211> LENGTH: 13
<212> TYPE: PRT
<213> ORGANISM: Oryctolagus cuniculus

<400> SEQUENCE: 72

Ala Gly Gly Tyr Ser Ser Ser Val Asp Phe Phe Phe Ala
1               5                   10

<210> SEQ ID NO 73
<211> LENGTH: 10
<212> TYPE: PRT
<213> ORGANISM: Mus musculus

<400> SEQUENCE: 73

Ser Ala Thr Ser Ser Ile Thr Tyr Ile His
1               5                   10

```
<210> SEQ ID NO 74
<211> LENGTH: 7
<212> TYPE: PRT
<213> ORGANISM: Mus musculus

<400> SEQUENCE: 74

Asp Thr Ser Arg Leu Ala Ser
1               5

<210> SEQ ID NO 75
<211> LENGTH: 9
<212> TYPE: PRT
<213> ORGANISM: Mus musculus

<400> SEQUENCE: 75

Gln Gln Trp Ser Ser Asn Pro Pro Thr
1               5
```

METHODS OF TREATING A HEMOLYTIC DISORDER COMPRISING ADMINISTERING ANTI-PROPERDIN ANTIBODIES

RELATED APPLICATION

This application claims priority benefit of U.S. Provisional Patent Application Ser. No. 61/709,796, filed on Oct. 4, 2012, the content of which is incorporated herein by reference in its entirety.

BACKGROUND

The complement system can be activated through three distinct enzymatic cascades, referred to as the "classical pathway", "Lectin/MBL", and "alternative" pathway" (CP, MBL, and AP respectively). MBL is not discussed here. The classical pathway is responsible for aiding in host defense against antigens to prevent infection of cells. The lectin pathway is a variation of the classical pathway. The alternative pathway is currently thought to be responsible for 80-95% of total complement activity in cases where trigger of complement activation is the classical pathway ("AP amplification loop"). The alternative pathway by itself is activated in a number of disease indications where complement components have been found in elevated state.

There are three "alternative pathway specific proteins"; Factors B, D, and P, which play a major role in the; a) initiation and propagation of the alternative pathway and b) classical pathway propagation via the alternative pathway amplification loop. Proteins C3 and C3b, the key players in complement system, are common to all classical and alternative complement pathways. While there may be a one type of C3, there are three different types of C3b produced as each C3 convertase is different. AP C3 convertase is composed of PC3bBb, the classical C3 convertase is made up of different proteins. Therefore it is hard to believe that the cut would be all identical to produce similar C3b molecules. As a result, C3b produced by the alternative pathway is different compared to C3b produced via the classical pathway.

The classical pathway (CP) is initiated by antigen-antibody complex. The CP progression involves proteins such as C1Q, C1r/C1s, C4, and C2. The CP C3 convertase consists of C3bC4b2a. This complex can cleave the C3 into C3b and C3a. This C3b is derived from classical pathway convertase and is usually required for opsonization of various pathogens and bacteria. Inhibition of this C3b is undesirable. C3b coated cells are removed via complement receptors present on various cells.

Both complement pathways independently produce C3a, C3b, C5a, C5b, C5b-9, and sC5b-9 as complement activation byproducts.

During classical pathway triggered activation of the alternative pathway, Classical pathway C3 convertase also cleaves C3 into C3b which can work independent of the alternative pathway with full amplification of the classical pathway in 1% normal human serum in the presence of $Ca^{2+}/Mg^{2+}$ ions. Classical pathway C5 convertase can cleave C5 to generate C5a and C5b. The C5b molecule then inserts into the lipid bilayer of the cell to initiate the formation of C5b-9 or sC5b-9.

In alternative pathway activation, C3b produced by the complement system can bind properdin and Factor B to form the complex "PC3bB". Factor D then cleaves Factor B, within the complex, into Bb and Ba. This cleavage results in the release of Ba from the complex and the formation of the AP convertase PC3bBb. PC3bBb cleaves C3 into C3a and C3b, thereby perpetuating the amplification loop of the alternative pathway for the benefit of the alternative pathway. PC3bBb can then cleave C5 to make C5b and C5a. The C5b molecule then inserts into a lipid bilayer of a cell and forms the nucleus for MAC deposition.

The classical pathway can also initiate the propagation of a part of the alternative pathway known as the amplification loop. Within the amplification loop, C3b binds properdin and Factor B to form the complex "PC3bB". Factor D then cleaves Factor B, within the complex, into Bb and Ba. This cleavage results in the release of Ba from the complex and the formation of the AP convertase PC3bBb. PC3bBb cleaves C3 into C3a and C3b, thereby perpetuating the amplification loop.

C3b is therefore both a component and a byproduct of the complement system irrespective of the type of complement pathway activation. During the amplification of the AP, as the PC3bBb (AP C3 Convertase) generates increasing amounts of C3b, an amplification loop is established so that activation of the alternative pathway can continue. Furthermore, the classical pathway can also generate C3b, which can bind factor B and thereby engage the alternative pathway, even though the trigger is CP mediated. This allows more C3b to deposit on a target, which leads to enhanced amplification of AP activation.

Addition of newly formed C3b to the existing AP C3 convertase PC3bBb generates the AP C5 convertase. Addition of newly formed C3b to the existing CP C3 convertase generates CP C5 convertase. Both C5 convertases have the ability to cleave C5 to produce C5b and C5a. The terminal complex produced as a result of complement activation is known as the MAC complex (also known as C5b-9 or sC5b-9), which is responsible for lysis of cells in a subject. Both C3a and C5a are potent anaphylatoxins that are responsible for activating platelets, neutrophils, and monocytes. As a result, inflammatory molecules such as elastase, TNF-α, IL-1, VEGF, and peroxides are released. Formation of C5b-9/sC5b-9 is responsible for tissue damage and tissue injury/tissue damage seen in "other diseases"

Classical complement pathway activation provides a valuable first-line defense against potential pathogens and can generate C3a/C3b, C5a/C5b, and C5b-9/sC5b-9. Therefore, exacerbation of the classical pathway can produce large amounts of complement byproducts. As described elsewhere, both C3a and C5a are potent anaphylatoxins, C3b mediates opsonization, and C5b is responsible for wanted killing of the pathogens. Here, both C3a and C5a would generate beneficial responses and are produced to kill the invaders. This pathway is required for host defense and therefore must not be inhibited.

Alternative pathway activation in Mg++ ions, without the calcium ions, guarantees only the AP activation. In disease state, this pathway is activated independent of the classical pathway. This pathway is not required for host defense and therefore can be inhibited in its entirety.

SUMMARY

Embodiments described herein relate to antibodies that prevent C3b formation responsible for extravascular hemolysis and C5b-9 responsible for intravascular hemolysis. The invention further relates to methods for treatment of subjects suffering from disorders that involve lysis of red blood cells and platelets via intravascular and extravascular route. The invention also covers protection of neutrophils, monocytes, platelets, and T-lymphocytes against complement attack. This is accomplished by antibodies of the claimed genus that block the formation and deposition of C3b on cells and C5b-9 on cells that are deficient in GPI linked proteins.

This application summarizes a group of complement inhibitor monoclonal antibodies that prevent the formation of alternative pathway derived C3b and C5b-9 formation. These antibodies are being claimed as a genus in this particular application. Although these antibodies bind different targets within the alternative pathway, they have unique feature as they all inhibit alternative pathway generated C3b called 'C3b" but not the classical pathway generated C3b.

It is Removal of cells causes cytopenia depending upon the cell type under attack—neutropenia, monocytopenia, thrombocytopenia, lymphocytopenia, and leukopenia. Thus, inhibition of AP activation by a claimed genus of monoclonal antibodies can prevent cytopenia in a subject (human). Cytopenia is commonly observed in hematological disorders such as Paroxysmal Nocturnal Hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, Neonatal Allo-Immune Thrombocytopenia (NAITP). The antibodies of the claimed genus are capable of preventing cytopenia, cellular activation, cell dysfunction, inflammation, extravascular hemolysis, intravascular hemolysis and tissue injury.

Both the classical and the alternative pathways upon activation produce C3b molecules. The two C3b although called the same but are different. C3b molecules produced by alternative pathway but not the classical pathway in PNH bind erythrocytes, neutrophils, monocytes, platelets, and T lymphocytes. This binding results in clearance of such cells via extravascular hemolysis. Removal via extravascular hemolysis causes cytopenia and increased levels of bilirubin and LDH. C5b-9 (also known as MAC) deposits onto the cell membrane and results in lysis of anucleated cells such as erythrocytes and platelets. Clear evidence of C3b deposition and C5b-9 deposition have not been reported previously. Erythrocyte lysis results in increased LDH levels, increased reticulocyte counts and decreased levels of hemoglobin in erythrocytes.

In PNH, we found that C3b and C5b-9 have been associated with both anucleated and nucleated cells. These patterns of C3b and C5b-9 binding to a variety of cells deficient in GPI linked proteins suggests destruction/partial destruction, activation, or dysfunction of such cells. Current invention is to prevent the formation and deposition of such molecules on a variety of anucleated and nucleated cells that are responsible for pathological outcomes in diseases where the absence of GPI liked proteins is associated with pathology. Neutralizing antibodies that prevent the formation of C3b and C5b-9 via the alternative pathway are covered under this invention.

As an example of hematological disorder where cytopenia occurs is PNH. Cytopenia covers leukopenia, neutropenia, monocytopenia, thrombocytopenia, lymphocytopenia. Nearly all types of cells appear to be deficient in GPI linked proteins in PNH. Such cells are subject to complement attack via C3b deposition and extravascular removal and/or destruction via extravascular route. All antibodies that are selective blocker of only alternative pathway-derived C3b and C5b-9 are covered under this invention. A set of such antibodies that perform such function are covered under this invention.

T-lymphocytes, monocytes, and neutrophils are all deficient in GPI linked proteins and therefore are subject to complement attack and deposition of C3b and C5b-9. C3b coated cells would be deprived of the proper function and C5b-9 deposition would cause cell death resulting in loss of the cells. As an example, the neutrophil is the key cell fighting bacterial and fungal infection in the body. These neutrophils in PNH patients may not ingest germs effectively and are therefore less able to fight infection. These patients, whose white blood cells don't work properly, are much more likely to develop a second infection. It is known via the laboratory testing that by adding GM-CSF in the laboratory testing, it is possible to restore the ability of the white blood cells to ingest bacteria and fight infection. Thus addition of GM-CSF is proposed as a potential use in patients to increase the ability of neutrophils to behave normally. The main function of GM-CSF is known. The protein is a cytokine that functions as a white blood cell growth factor in general. GM-CSF stimulates stem cells to produce granulocytes (neutrophils, eosinophils, and basophils) and monocytes. Thus increased amount of GM-CSF seen in the PNH blood samples indicates that PNH cells are dying. Thus adding GM-CSF with and without the claimed genus of antibodies could help improve the cell quality in general and increase the ability of cells to fight infections.

Based on the old convergence theory describing C3 being the convergence point, those with ordinary skill in the art would expect any activation of the classical pathway to invariably have the effect of alternative pathway activation. This is because the two pathways are believed to "overlap" at the starting point of the C3. According this theory, C3b produced via the classical pathway participates in the AP amplification loop. The invention that is the subject of this patent is the development of a new and unique genus of complement inhibiting antibodies which challenge that assumption. The claimed invention, this new genus of antibodies, specific targets components of the alternative pathway amplification loop in such a way as to inhibit the alternative pathway regardless of whether or not the AP amplification loop has been otherwise triggered by the classical pathway. Thus anti-C3b antibodies of the current invention only inhibit the AP and not the CP amplification loop or the CP propagation. The uniqueness of the invention is not only which components these antibodies target, but how they target those components. Similarly, we describe the anti-Ba, anti-Bb, and -P and anti-C3b for the invention.

Figure 2:
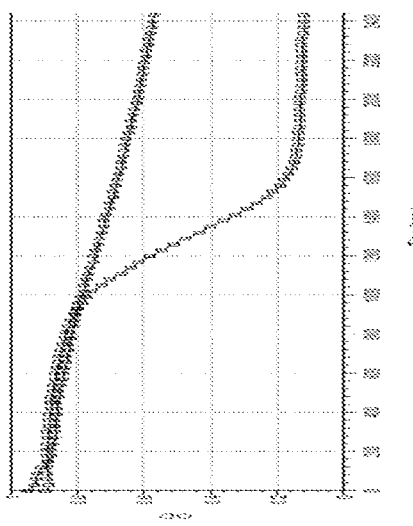
Figure 2:
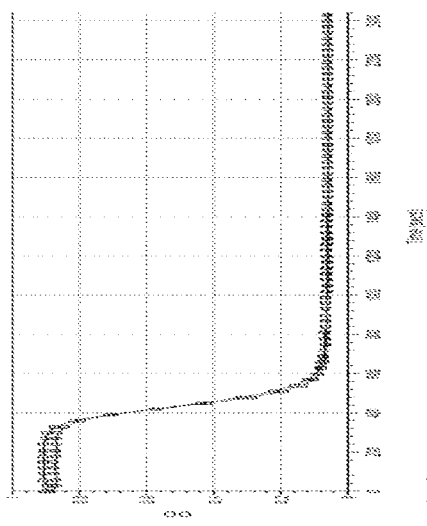
Figure 2:
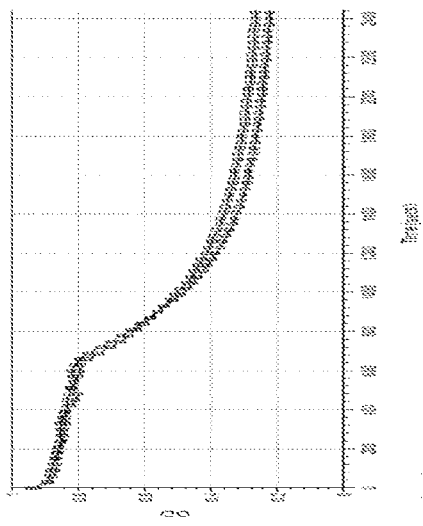
Figure 4:
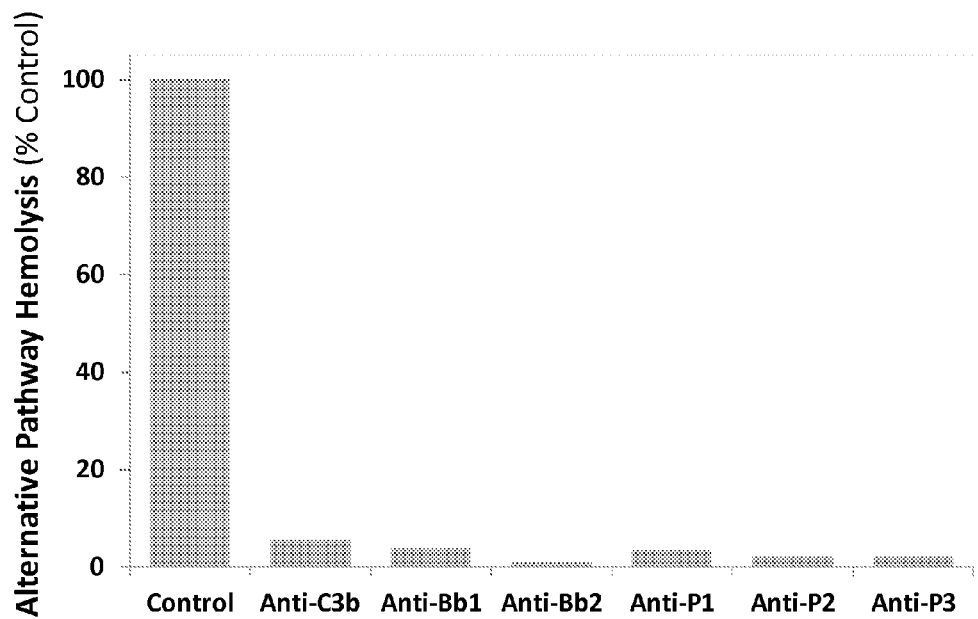

FIG. 2 illustrates three assay figure tracings from real data generated from one of the invented antibodies as a representative FIG. 4. One line represents untreated sample whereas the second line represents the antibody treated sample. The Panel A is a CP assay conducted in 1% NHS in CP buffer. The second panel is a CP assay in 10% NHS that allows CP amplification loop to contribute into the AP. The third panel (Panel C) shows inhibition by the invented antibodies of the genus that inhibit the AP without affecting the CP (Panel B). All antibodies showing this pattern would belong to the invented genus.

Figure 3:
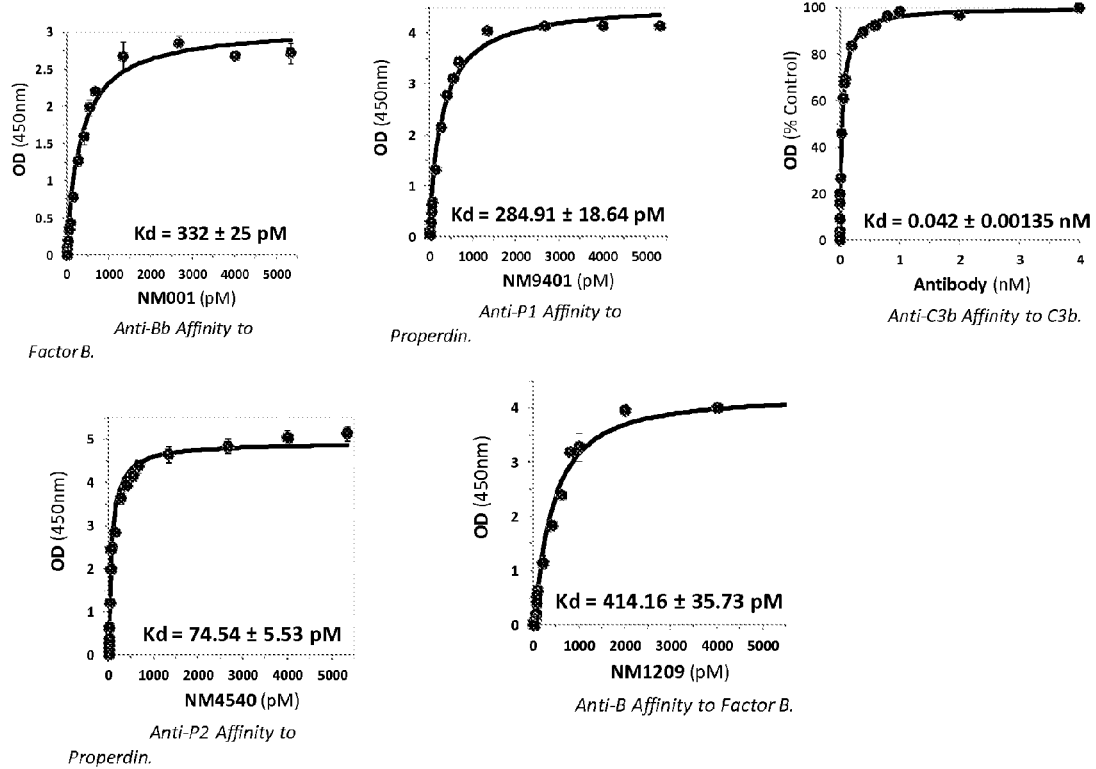

FIGS. 3 (a-e) are plots showing the binding affinities of the invented antibodies to their respective targets (C3b, Bb, and P).

Figure 7:
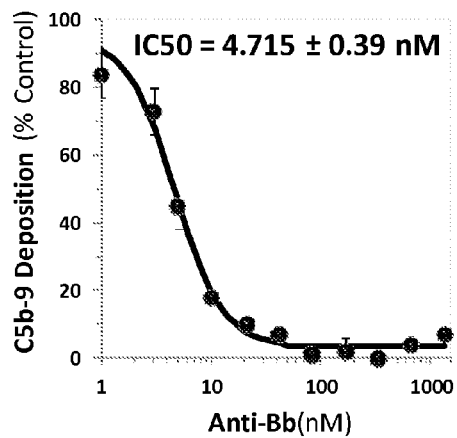
Figure 7:
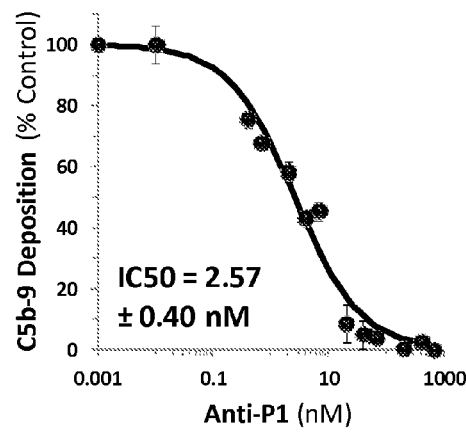
Figure 7:
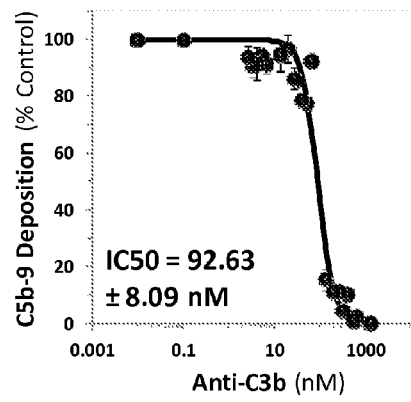
Figure 7:
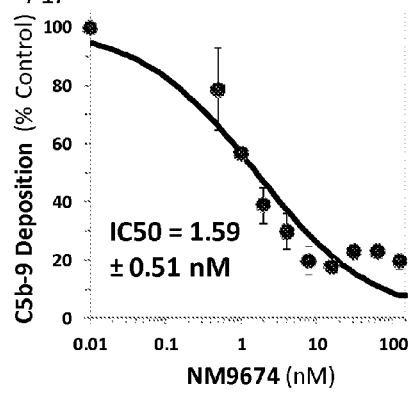

FIG. 4 is a graph showing that the invented antibodies inhibit alternative pathway dependent hemolysis of rabbit erythrocytes (rRBC) in Human Serum (NHS). There exist a multitude of antibodies which inhibit the activities of Properdin (Factor P), Factor Bb, and C3b. All such antibodies inhibit the alternative pathway and not the CP (FIG. 7). However, these antibodies will act on their targets in such a way as to inhibit the alternative pathway without inhibiting the classical pathway.

Figure 5:
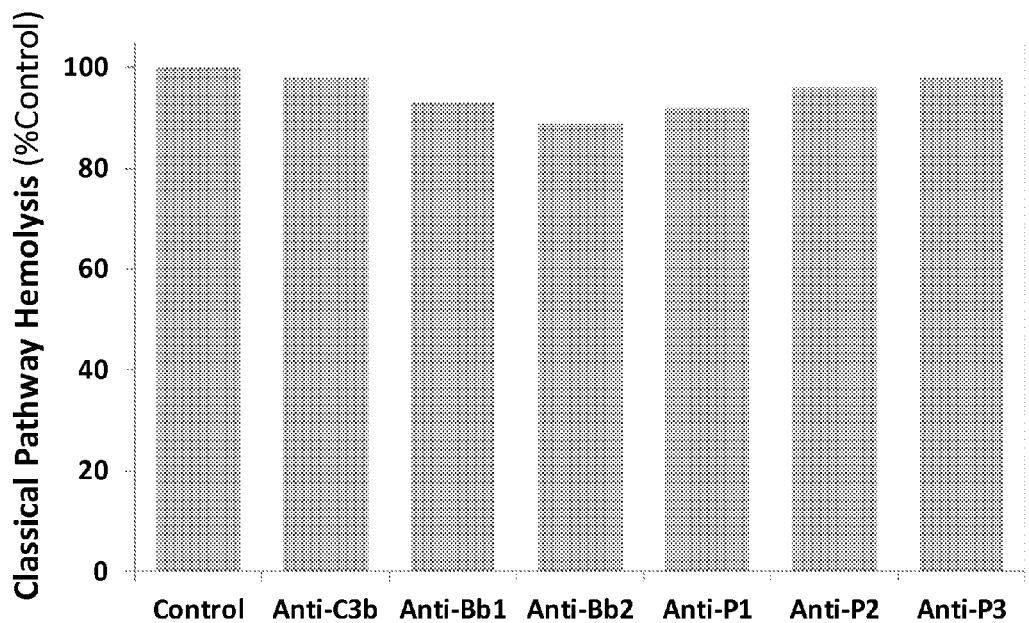

FIG. 5 is a graph showing that the invented antibodies do not inhibit classical pathway dependent lysis of Antibody Sensitized Sheep Erythrocytes (sRBC). The current state of the act teaches that activation of the classical pathway invariably results in activation of the alternative pathway at the amplification loop, which begins with cleavage of C3 by CP produced C3 convertase. The claimed invention makes possible the therapeutic inhibition of the alternative pathway, despite classical pathway activity. As shown, the Anti-C3b, Anti-Ba, Anti-Bb, and Anti-P antibodies of the invented genus do not inhibit the classical pathway and are specific to the alternative complement pathway (FIGS. 2-3). Therefore, the invention could have potential application in any disease characterized or mediated by a pathological over-activation of the alternative complement pathway.

Figure 6:
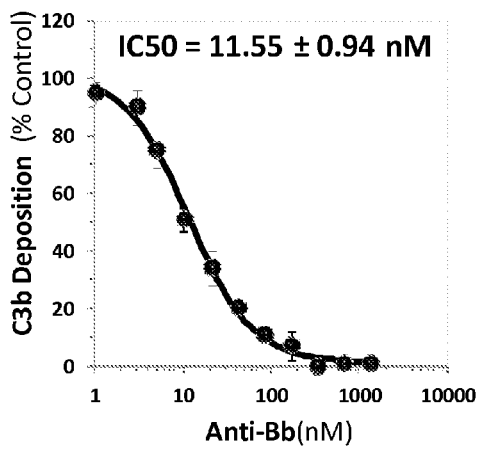
Figure 6:
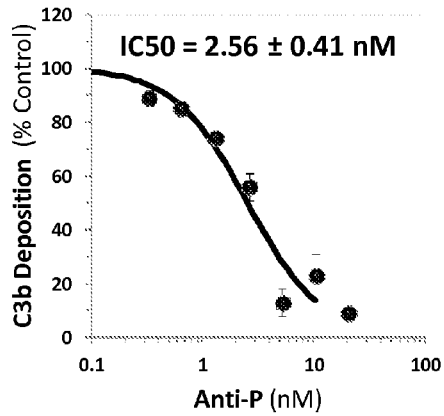
Figure 6:
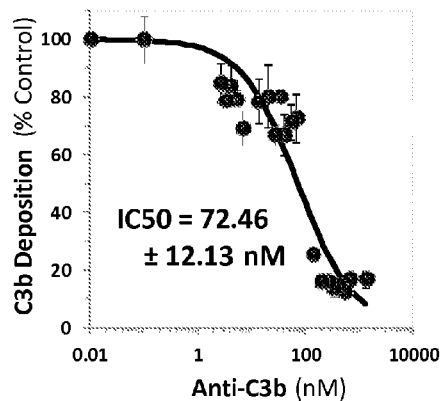
Figure 6:
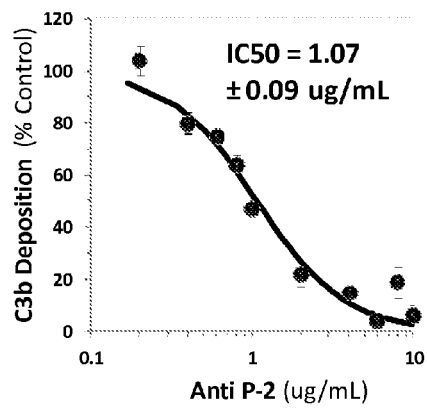

FIGS. 6 (a-c) illustrate plots showing that the invented antibodies inhibit the formation of C3b in serum, a marker for extravascular hemolysis.

FIGS. 7 (a-c) illustrate plots showing that the invented antibodies inhibit the formation of C5b-9 in serum, a marker for intravascular hemolysis.

Figure 8:
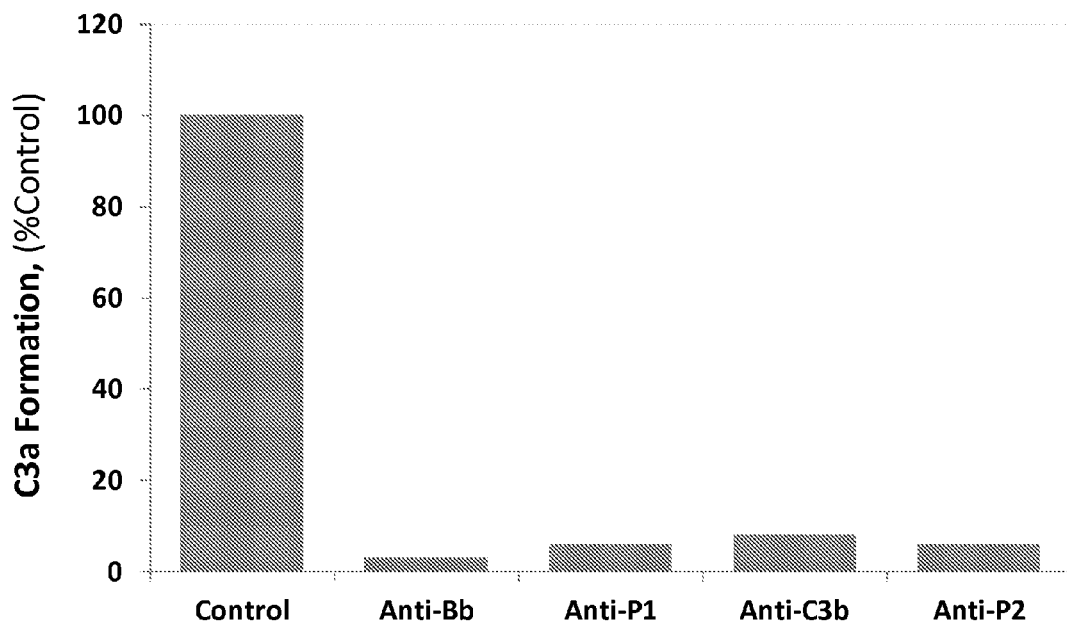

FIG. 8 is a graph showing that the invented antibodies inhibit the formation of C3a in Whole Blood Inflammation. Both C3a (cleaved from C3) and C5a (cleaved from C5) are potent anaphylatoxins (triggers of local inflammation) that are produced upon complement activation. Both the classical pathway and the alternative pathway produce these molecules. The Figure shows the inhibition of C3a derived from the alternative complement pathway. Classical pathway trigger does not exist in this model.

Figure 9:
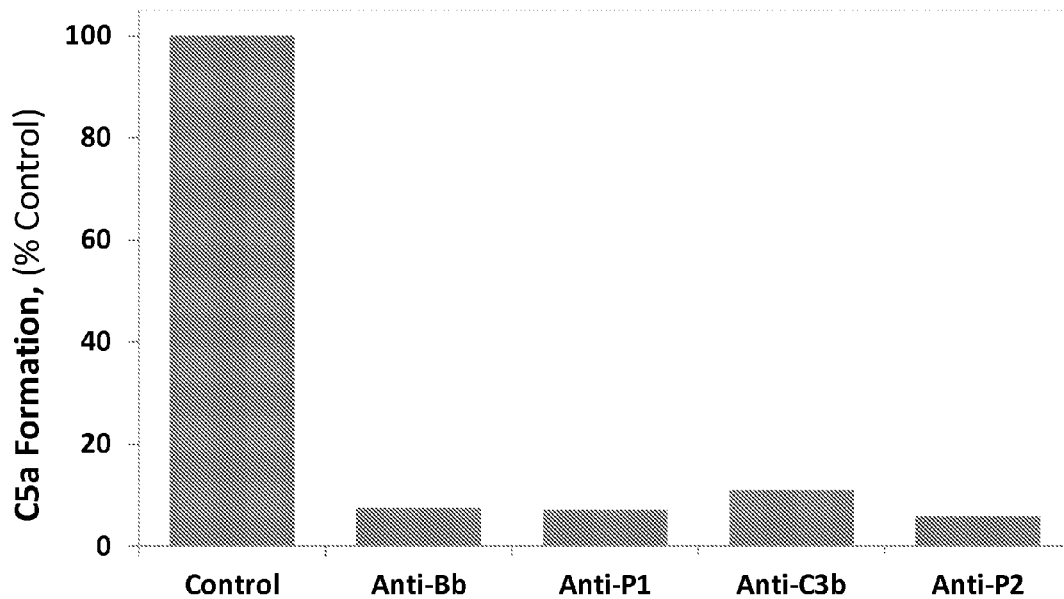

FIG. 9 is a graph showing that the invented antibodies inhibit the formation of C5a in Whole Blood Inflammation. The claimed invention selectively inhibits C3a (FIG. 8) and C5a (FIG. 9) produced from the alternative pathway.

Figure 10:
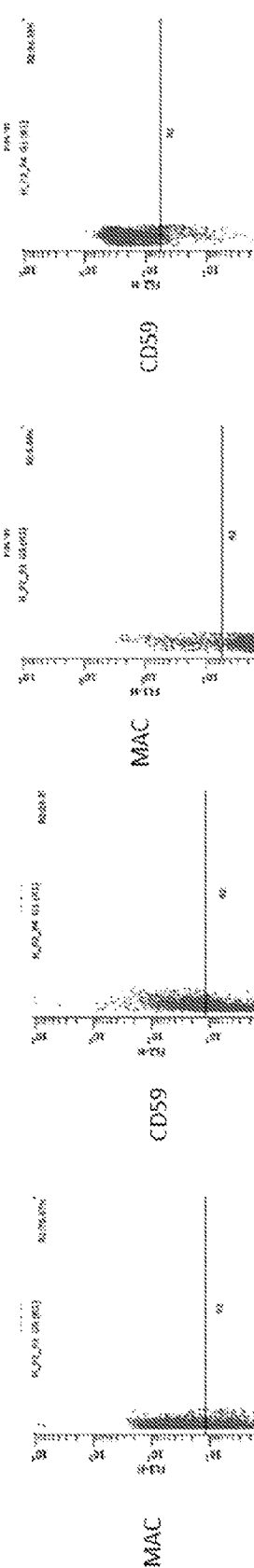
Figure 10:
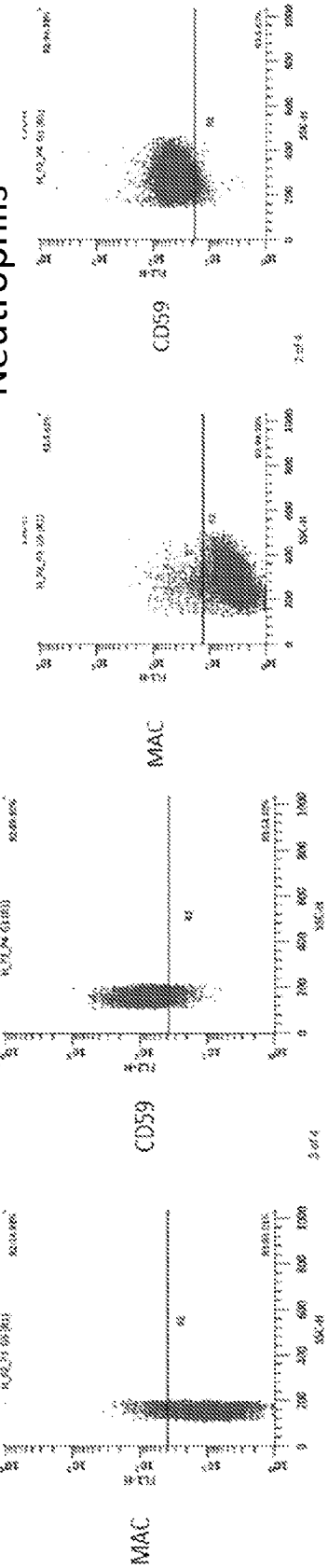

FIG. 10 is a graph showing that the invented antibodies Inhibit formation of sC5b-9 in Whole Blood.

Figure 11:
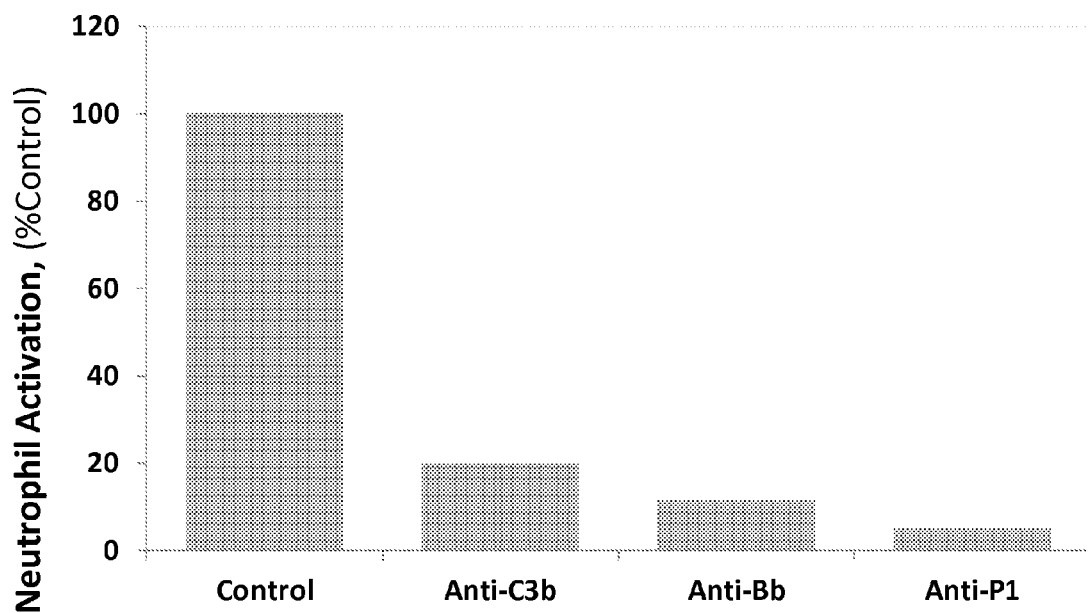

FIG. 11 is a graph showing that the invented antibodies inhibit neutrophil activation. The neutrophils activation occurs due to the activation of the AP and not CP or CP-induced AP.

Figure 12:
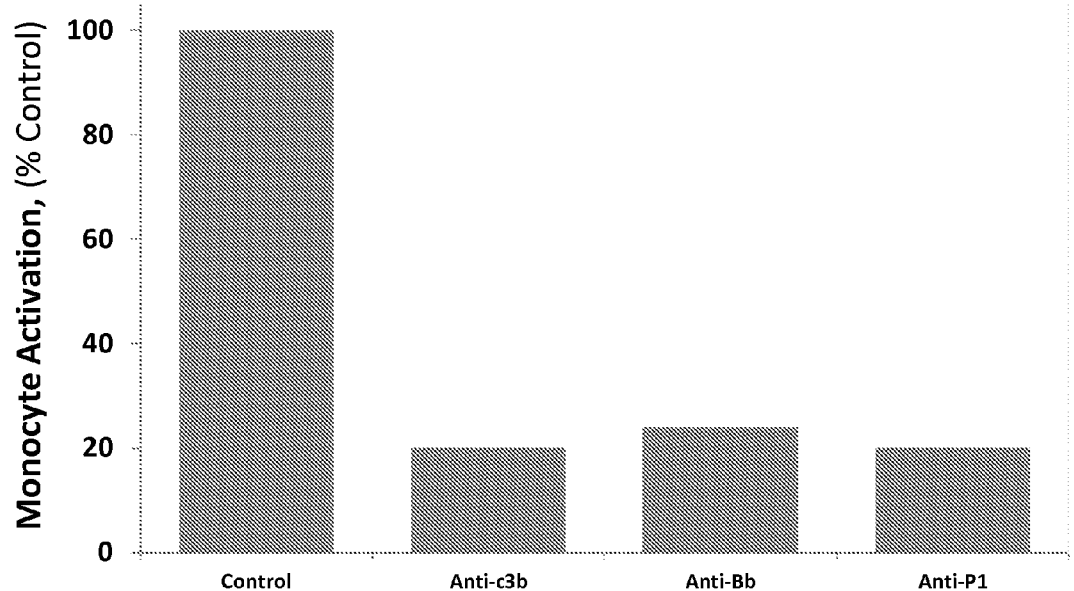

FIG. 12 is a graph showing that the invented antibodies inhibit monocyte activation. The monocyte activation occurs due to the activation of the AP and not CP or CP-induced AP.

Figure 13:
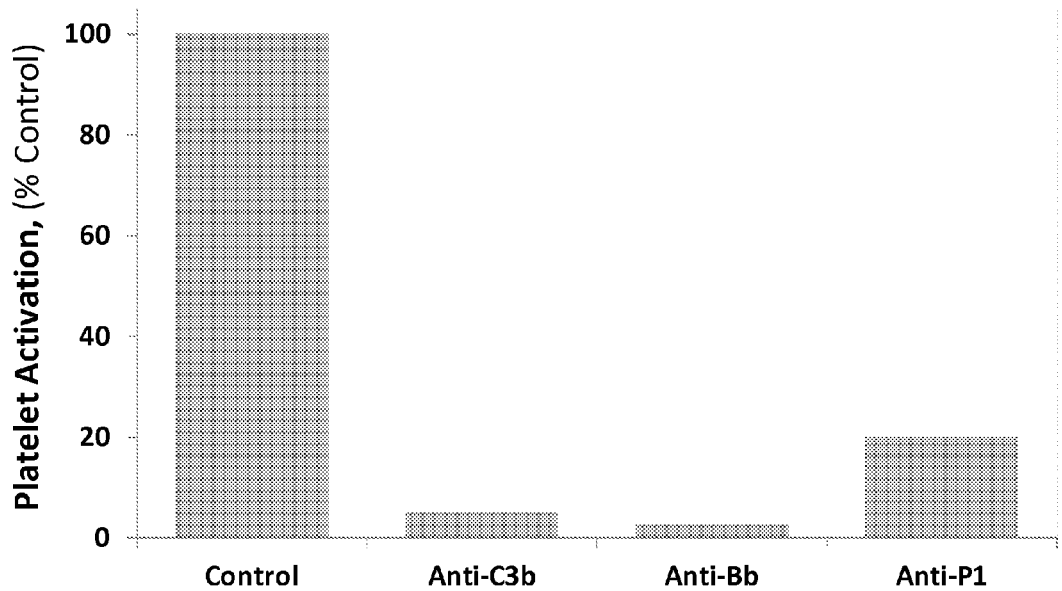

FIG. 13 is a graph showing that the invented antibodies inhibit platelet activation. The platelet activation occurs due to the activation of the AP and not CP or CP-induced AP.

Figure 14:
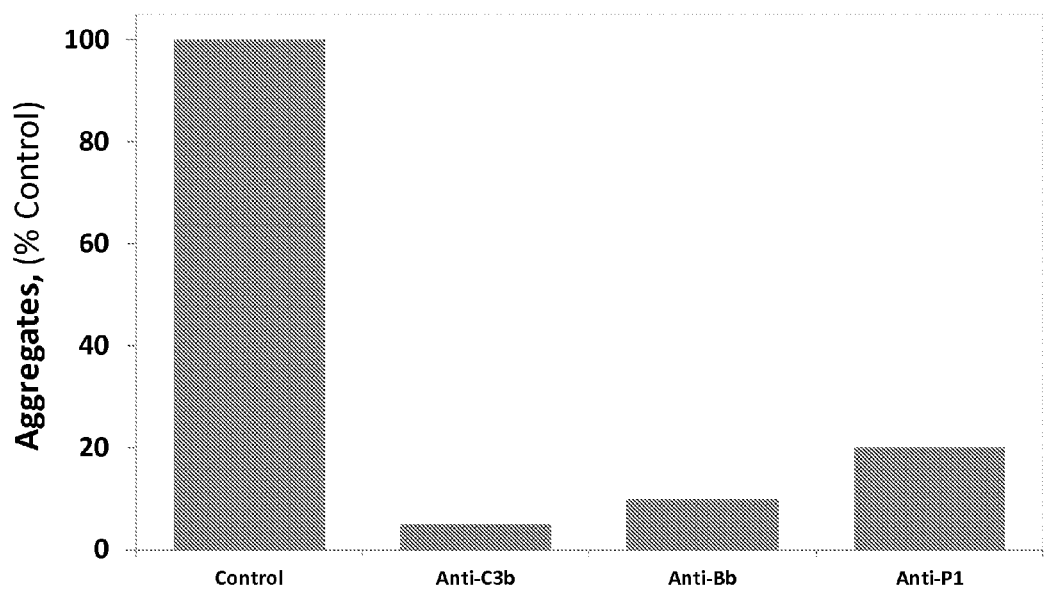

FIG. 14 is a graph showing that the invented antibodies inhibit monocyte-platelet aggregates. The monocyte-platelet aggregation occurs due to the activation of the AP and not CP or CP-induced AP.

Figure 15:
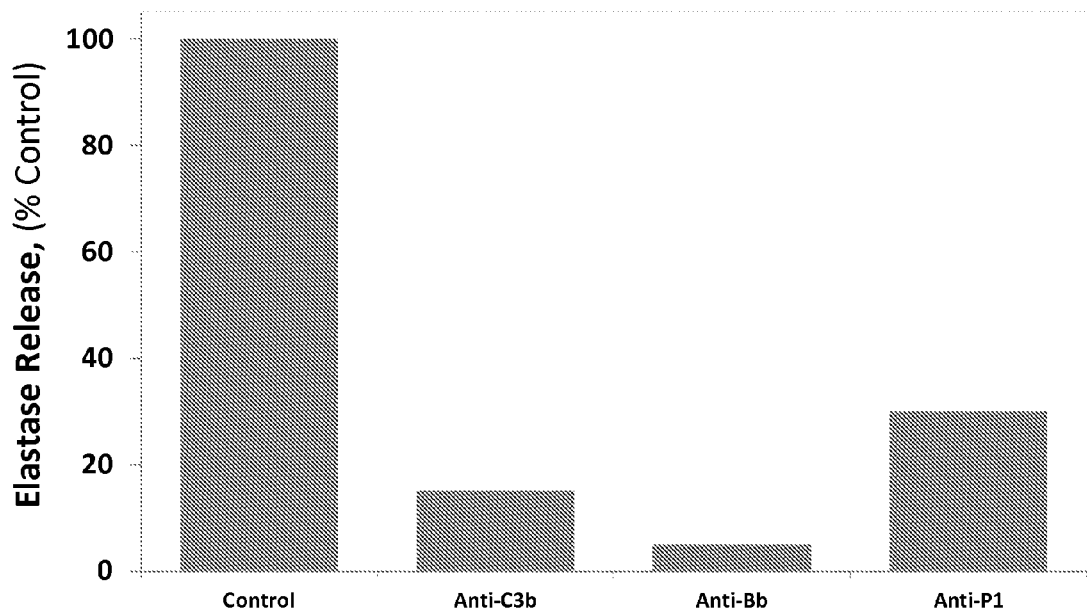

FIG. 15 is a graph showing that the invented antibodies inhibit elastase release from neutrophils. The neutrophil elastase is produced from neutrophils that are activated via the C3a/C5a produced from the alternative pathway.

Figure 16:
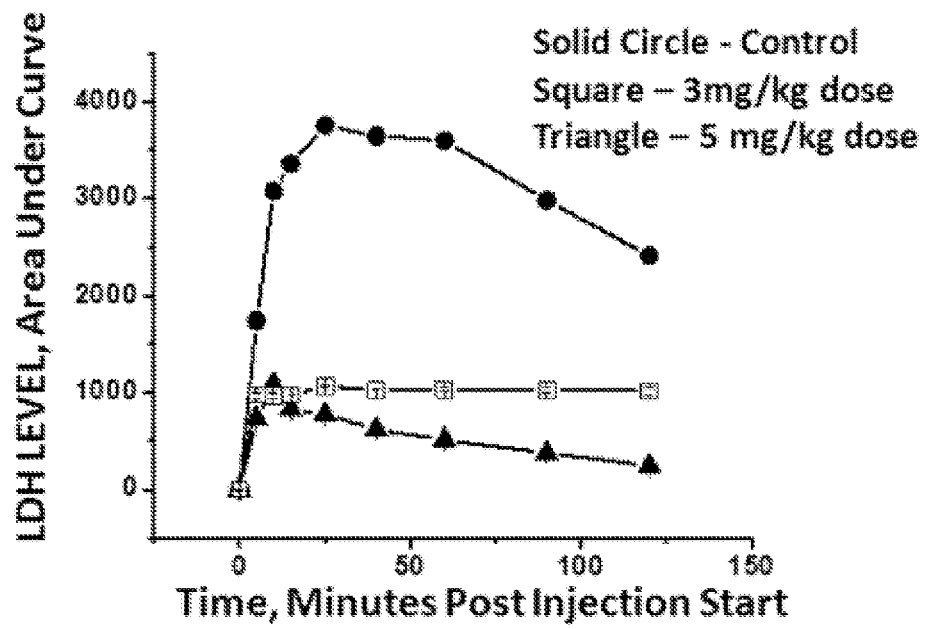

FIG. 16 is a graph showing antibodies of the invention prevent LDH release in an in vivo model of PNH.

Figure 17:
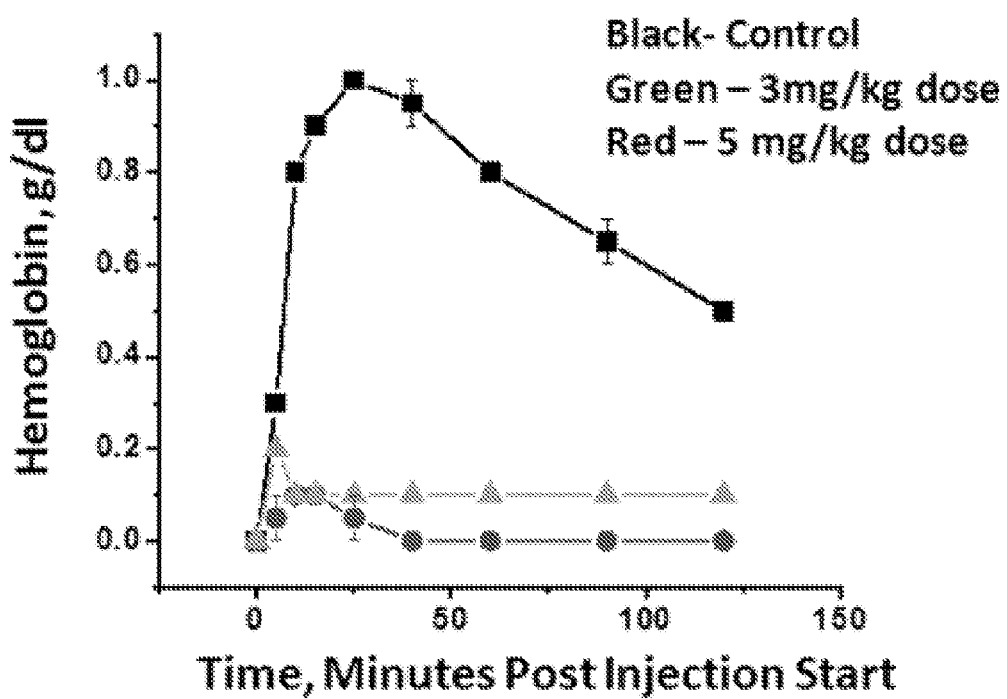

FIG. 17 is a graph showing antibodies of the invention prevent HgB release in vivo in a model of PNH.

Figure 18:
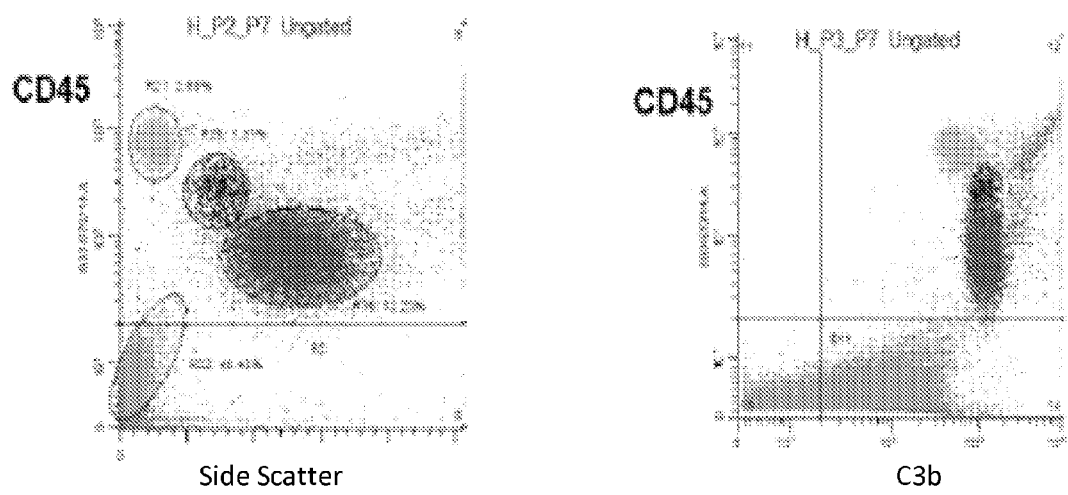

FIG. 18 illustrates a graph showing cells in blood from PNH patients.

DETAILED DESCRIPTION

Definitions

Unless specifically defined herein, all terms used in this document have the same meaning as would be understood by those of ordinary skill in the art of the present invention. The following definitions are provided for clarity, and to define their intended meaning as used in the specification and claims to describe the present invention.

Complement Pathways

"CLASSICAL PATHWAY" refers to complement which is triggered by antigen-antibody complexes for activation and may or may not also trigger the alternative pathway amplification loop for its propagation.

"ALTERNATIVE PATHWAY" refers to complement activation which is triggered by a cell surface (or cell-surface like material) looking like a foreign surface. The absence of GPI linked protein makes the surface of the PNH cell foreign enough to activate the alternative pathway. The alternative pathway may also begin with spontaneous proteolytic generation of C3b from complement factor C3, where C3b has the ability to bind B and P both.

"ALTERNATIVE PATHWAY SPECIFIC PROTEIN" refers to C3b, factor B, factor Bb, factor D, and/or properdin. Here C3b refers to C3b as a part of the AP and not CP.

"AP AMPLIFICATION LOOP" refers to a looping series of reactions in which C3b formed makes AP C3 convertase. This convertase cleaves C3 and generates more C3b, which feeds back into the loop. This self-perpetuating cycle of reactions generates large amounts of C3b.

"C3b" is term used for both C3b derived from AP and CP pathways.

"ALTERNATIVE PATHWAY-DEPENDENT C5a" describes the formation of C5a produced from activity of the alternative pathway of the complement system in whole blood. For example, "AP-dependent C5a formation" refers to the formation of C5a via activation of the alternative pathway, which is independent of the classical pathway.

"ALTERNATIVE PATHWAY-DEPENDENT sC5b-9" describes the formation of sC5b-9 produced from activity of the alternative pathway of the complement system. For example, "AP-dependent sC5b-9 (soluble MAC) formation" refers to the formation of sC5b-9 via activation of the alternative pathway, which is independent of the classical pathway.

"ALTERNATIVE PATHWAY-DEPENDENT C5b-9" describes the formation of C5b-9 produced from activity of the alternative pathway of the complement system. For example, "AP-dependent C5b-9 formation (Deposited MAC)" refers to the formation of C5b-9 via activation of the alternative pathway, which is independent of the classical pathway.

"C3a DEPENDENT CELLULAR ACTIVATION" describes the activation of neutrophils, monocytes, platelets, T lymphocytes, endothelial cells, mast cells, and platelets which occurs when Alternative Pathway-Dependent C3a binds to C3a receptors, which are present on these cells. These cells are found, in their C3a activated state, in various different diseases (see OTHER DISEASES).

"C5a DEPENDENT CELLULAR ACTIVATION" describes the activation of neutrophils, monocytes, platelets, T lymphocytes, endothelial cells, mast cells, and platelets which occurs when Alternative Pathway-Dependent C5a binds to C5a receptors, which are present on these cells. These cells are found, in their C5a activated state, in various different diseases (see "OTHER DISEASES").

"C5b-9 and sC5b-9 DEPENDENT TISSUE INJURY/CELLULAR DAMAGE" describes the cellular damage caused by the formation of sC5b-9 and/or C5b-9. These molecules either bind to the cellular surface and/or insert themselves into the cell's plasma membrane resulting in pathological conditions also described as "TISSUE INJURY". Tissue injury occurs in various diseases and can result in the damage to various organs.

"MEMBRANE ATTACK COMPLEX" ("MAC") refers to a complex of the terminal five complement components (C5b-C9) that inserts into and disrupts cell membranes. This complex is also referred to as C5b-9. MAC complex is produced by both the alternative pathway and by the classical complement pathway. The complex that is associated with "S protein" is called sC5b-9, a soluble form of MAC. The invented antibodies inhibit alternative pathway associated C5b-9 and sC5b-9.

"C3a, C5a, C5b-9, sC5b-9 AND INFLAMMATION" describes inflammation caused by the products of AP activation and activity; and in particular, the AP products C3a, C5a, C5b-9, and sC5b-9 generating from AP activity. These molecules cause C3a DEPENDENT CELLULAR ACTIVATION, C5a DEPENDENT CELLULAR ACTIVATION, C5b-9 and sC5b-9 DEPENDENT CELLULAR DAMAGE, and result in the prevalence of CYTOKINE ACTIVATED CELLS, PROTEASE ACTIVATED CELLS, and PEROXIDE ACTIVATED CELLS, all of which can be implemented in various different diseases and disease pathologies.

Whole Blood & Inflammation

"WHOLE BLOOD" describes complete blood with the same composition of cells, chemicals, proteins, etc. as blood found in human blood vessels. The isolated blood contains all components of the complement system including inflammatory cells that are responsible for inflammatory responses.

"INFLAMMATION IN WHOLE BLOOD" describes the cascade of reactions beginning with alternative pathway activation in whole blood, the resulting production of C3a, C5a, and C5b-9 and sC5b-9 in whole blood, the resulting activation of neutrophils monocytes and platelets in whole blood, and ultimately, the production of inflammatory cytokines in whole blood (in vivo or ex vivo). Several inflammatory mediators are found to be secreted into the plasma. These inflammatory mediators are TNF, IL-1, IL-6, IL-8 and several others. Not included in the list.

"ALTERNATIVE PATHWAY (AP)-DEPENDENT INFLAMMATION IN HEMOLYTIC DISEASES" refers to an increase in alternative complement pathway activity, as measured by continued or increased formation, and/or release, of one or more of the following components C3a, C3b, C5a, C5b-9, or sC5b-9, and all the anticipated consequences thereof, in PNH and other hemolytic diseases. Such anticipated consequences include; continued or increased AP-dependent MAC-mediated deposition and/or lysis of cells, continued or increased AP-dependent activation of platelets, monocytes, neutrophils, mast cells, or basophils; and/or continued or increased AP-dependent formation or release of TNF-α, IL-1, or neutrophil elastase.

"OTHER ORPHAN AND NON_ORPHAN HEMATOLOGICAL AND NON HEMATOLOGICAL ACUTE AND CHRONIC DISEASES" describes a list of diseases where one of the elevated components measured is derived from the activation of the alternative pathway system. These components include but not limited to; C3a/C3b, P, Ba/Bb, C5a/C5a, and C5b-9/sC5b-9. Elevated levels of these components have been found associated with one or more diseases. These components are responsible for cellular activation and release of inflammatory mediators. These, in turn, ultimately cause tissue damage, defining the disease in both hematological and non-hematological diseases.

"ALTERNATIVE PATHWAY (AP)-DEPENDENT INFLAMMATION IN PNH" refers to an increase in alternative complement pathway activity, as measured by continued or increased formation, and/or release, of C3a, C3b, C5a, C5b, C5b-9, and/or sC5b-9, and all the anticipated consequences thereof. Such anticipated consequences include; continued or increased AP-dependent C3b and MAC-mediated deposition or lysis of cells, continued or increased AP-dependent activation of platelets, monocytes, neutrophils, mast cells, or basophils; and/or continued or increased AP-dependent formation or release of TNF-α, IL-1, or neutrophil elastase.

"AUTOIMMUNE DISEASE" refers to a condition where the immune response of a subject is inappropriately directed against substances and tissues normally present in the body.

"CELLULAR LYSIS" indicates tissue injury in part. Cellular lysis occurs as a result of C5b-9 formation of the cell surface. Such deposition of C5b-9 leads to cellular injury and in case of tissues the cell injury is a tissue injury.

Inhibitory Antibodies and Agents

"AGENT" "COMPOUND" refers to any substance, molecule, element, compound, entity, or any combination thereof. An agent can be, among other things, a protein, oligopeptide, small organic molecule, polysaccharide, polynucleotide, or other biochemical substance. It can be a natural product, a synthetic compound, a chemical compound, or a combination of two or more substances of different origins. Unless otherwise specified, the terms "agent", "substance", and "compound" can be used interchangeably.

"Alternative pathway specific antibody" refers to an antibody or fragment thereof that can bind to an alternative pathway protein to inhibit activation and/or progression of the alternative pathway in a subject.

"ANTIBODIES TO AP PROTEINS" describe anti-P, anti-Ba, anti-Bb, anti-C3b antibodies that neutralize the activity of the alternative pathway without inhibiting the classical pathway.

Pharmacology

"PHARMACOKINETIC ACTIVITY" or "PHARMACOKINETICS" refers to the mechanisms of absorption and distribution of an administered drug, the rate at which a drug action begins and the duration of the effect, the chemical changes of the substance in the body, and the effects and routes of excretion of the metabolites of the drug "THERAPEUTICALLY EFFECTIVE AMOUNT" is defined as an amount sufficient to completely inhibit AP activity in vivo As used herein, a "prophylactically effective amount" is defined as an amount sufficient to prevent the onset of a disease or disorder in a subject.

As used herein, the terms "administering," "administration," and like refer to ways in which the antibody or antigen binding fragment thereof can be given to the subject, including, but not limited to, oral administration, intravenous administration, intraperitoneal, intramuscular, subcutaneous administration, aural administration, or rectal administration.

Antibodies

"ANTIBODY" used in the broadest sense includes monoclonal antibodies, including full length or partial length monoclonal antibodies, and polyclonal antibodies from mouse, rabbit or human species. The antibodies can also be egenrated in other mammalas. In its most widely recognized form, an antibody contains two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hyper-variability, termed complementarity determining regions (CDRs), interspersed with regions that are more conserved, termed framework regions (FR). Each VH and VL is composed of three CDRs and four Frameworks arranged from amino-terminus to carboxyl-terminus in the following order: FR1, CDR1, FR2, CDR2, FR3, CDR3, FR4. The variable regions of the heavy and light chains contain a binding domain that interacts with an antigen. The term "antibody" encompasses whole antibodies and antibody fragments thereof, derived from any antibody-producing mammal (e.g., mouse, rat, rabbit, and primate including human), that specifically bind to proteins such as properdin, C3b, Ba, and Bb or portions thereof. Exemplary antibodies include polyclonal, monoclonal and recombinant antibodies; multi-specific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"OTHER ANTIBODIES" refer to antibodies developed in living organism including and not limited to animals and humans for therapeutic use in humans and animals. Any antibodies raised in a living organism is capable of inhibiting AP mediated lysis (Assay-3) but not the CP mediated lysis or the CP amplification loop.

"ANTIBODY FRAGMENT" refers to a portion derived from or related to a full-length antibody, particularly an anti-C3b, anti-P, and anti-Ba, or anti-Bb antibody, generally including the antigen binding or variable region thereof (see "ANTIGEN BINDING FRAGMENT"). The term "antibody fragment" refers to a portion derived from a full-length alternative pathway inhibitory antibody, generally including the antigen binding and variable region thereof. Other antibodies include nano bodies, diabodies, linear antibodies, single-chain antibody molecules and multispecific antibodies formed from antibody fragments. Examples of antibody fragments include Fab, Fab', F(ab)2, F(ab')2 and Fv fragments, or scFv fragments (and any PEGylated variations of any of the forgoing).

"ANTIGEN BINDING FRAGMENT" of an antibody refers to the one or more fragments of an intact antibody that retain the ability to specifically bind to a given antigen. Antigen binding functions of an antibody can be performed by fragments of an intact antibody containing the Complementarity Determining Regions (CDRs). Examples of antigen binding fragments:

"Fab" fragments (single chain variable regions with VH and VL);

"Monovalent Fragments" (antibody fragments consisting of the VL, VH, CL and CH1 domains);

"F(ab')2" fragments (bivalent fragments comprising two Fab fragments linked by a disulfide bridge at the hinge region);

"Fd" fragments (which consist of the VH and CH1 domains of an antibody);

"Fv" fragment (which consist of the VL and VH domains of a single arm of an antibody);

single domain antibody ("dAb"), which consist of a VH domain or a VL domain;

an isolated Complementarity Determining Region ("CDR").

A "FUNCTIONAL DERIVATIVE" of an antibody is any compound which is either taken from, or incorporates within itself, the functional region of the antibody. Functional derivatives of antibodies include, but are not limited to, antigen binding fragments, CDRs, humanized antibodies, "Fab" fragments, "Fd" fragments, chimeric antibodies, monoclonal antibodies, recombinant antibodies, and single chain antibodies.

CDRs, as antigen binding fragments, can also be incorporated into single domain antibodies, maxi bodies, mini bodies, intrabodies, diabodies, triabodies, tetra bodies, v-NAR and bis-scFv. Antigen binding fragments of antibodies can be grafted into scaffolds based on polypeptides such as Fibronectin type III (Fn3). Antigen binding fragments can be incorporated into single chain molecules comprising a pair of tandem Fv segments (VH-CH1-VH-CH1) which, together with complementary light chain polypeptides, form a pair of antigen binding regions.

As used herein, the term "Fc region" refers to the region of the antibody that induces effector functions.

"AFFINITY" refers to the chemical strength of the interaction between an antibody and an antigen at single antigenic sites.

"BINDING SPECIFICITY" refers to the ability of an individual antibody or antigen binding fragment to bind to a particular target, e.g., the binding specificity of an antibody to bind only to its target.

"COMPOUNDS," "BLOCKER", "INHIBITOR", or "ANTAGONIST" refers to a chemical substance, or force, that retards or prevents a chemical or physiological reaction or response. Common blockers or inhibitors include, but are not limited to, antisense molecules, antibodies, antagonists and their derivatives. For example, an antibody that binds to a component of an AP specific interaction between that component and another component of the AP. Such an antibody would be an inhibitor or blocker of that interaction and, by extension, the AP.

"CHIMERIC ANTIBODY" is a recombinant protein that contains the variable domains and CDRs derived from an antibody of from a non-human species of animal, while the remainder of the antibody molecule is derived from a human antibody. The replacement of the non-binding region of the antibody with a human constant region enables the chimeric antibody to retain its specificity in recognizing and binding the targeted antigen while having reduced antigenicity in humans (compared to the original mouse antibody).

"HUMANIZED ANTIBODY" is an antibody that consists of non-human CDRs and humanized framework regions. Humanized antibodies are typically recombinant proteins in which only the antibody complementarity-determining regions are of non-human origin.

As used herein, a "single-chain Fv" or "scFv" antibody fragment comprises the VH and VL domains of an antibody, wherein these domains are present in a single polypeptide chain.

As used herein, the term immunogenicity refers to the ability of an antigen to initiate an immune response in a subject.

"COMPLEMENTARITY DETERMINING REGIONS (CDRs)" are the key binding regions of the antibody. There are typically three CDRs found within the variable regions of each of the two heavy and light chain variable regions. CDRs can be shuffled around, in terms of location, to create a particular binding affinity. See also "ANTIGEN BINDING FRAGMENTS."

"EFFECTOR FUNCTIONS" refer to those biological activities attributable to the native Fc region of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. In order to minimize or eliminate side effects of a therapeutic antibody, it may be preferable to minimize or eliminate effector functions.

As used herein, the term "reduced Fc effector function(s)" refers to the function(s) of an antibody wherein the antibody does not act against an antigen that recognizes the Fc region of the antibody. Examples of reduced Fc effector functions can include, but are not limited to, reduced Fc binding to the antigen, lack of Fc activation against an antigen, an Fc region that contains mutations to prevent normal Fc effector functions, or prevention of the activation of platelets and other cells that have Fc receptors.

"HUMAN ANTIBODY" is an antibody in which all components of the antibody are of human origin, including the framework, CDRs, and constant regions. The term "humanized" antibody is an antibody of non-human origin that retains the binding specificity of the non-human antibody while being less immunogenic in humans. See CHIMERIC ANTIBODY and HUMANIZED ANTIBODY.

"PURIFIED ANTIBODY" refers to antibodies which have been isolated from contaminants. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue, or preferably, silver stain.

"ISOTYPE" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

"MONOCLONAL ANTIBODY" refers to an antibody obtained from a population of substantially homogeneous antibodies, i.e., the individual antibodies comprising the population are identical. A monoclonal antibody is directed against a single determinant on the antigen. For example, the monoclonal antibodies useful in the present invention may be prepared by the hybridoma methodology or they may be made using recombinant DNA methods in bacterial or eukaryotic animal or plant cells. The "monoclonal antibodies" may also be isolated from phage antibody libraries, or generated using in vitro, in vivo, and cell culture methods. Monoclonal antibodies include those that bind to a unique sequence of amino acids and have a single specific epitope on its target antigen.

"POLYCLONAL ANTIBODY PREPARATIONS," unlike monoclonal antibody preparations, include different antibodies directed against different determinants (epitopes). As used herein, the term "polyclonal" refers to an antibody that recognizes multiple epitope sites on a single antigen.

"RECOMBINANT ANTIBODY" includes all antibodies that are prepared, expressed, created or isolated by recombinant means and methods.

"SINGLE CHAIN ANTIBODY" refers to an antibody in which the two domains of the Fv fragment, VL and VH, are coded for by separate genes. These genes can be joined, using recombinant methods, by an artificial peptide linker. Joining the genes results in the production of a single protein chain in which the VL and VH regions pair to form monovalent molecules (known as single chain Fv, "scFv"). Such single chain antibodies include one or more "antigen binding fragments" of an antibody. See ANTIGEN BINDING FRAGMENT.

"THERAPEUTIC ANTIBODY" refers to an antibody that may be considered effective in a therapeutic or prophylactic context with regard to a disease or condition of interest.

Amino Acids and Amino Acid Sequence

"AMINO ACID," in the broadest sense, refers to the naturally occurring amino acids which can be divided into groups based upon the chemical characteristic of the side chain of the respective amino acids. "Hydrophobic" amino acids are Ile, Leu, Met, Phe, Trp, Tyr, Val, Ala, Cys and Pro. "Hydrophilic" amino acids are, Asn, Gln, Ser, Thr, Asp, Glu, Lys, Arg and His. The "uncharged hydrophilic" amino acids are Ser, Thr, Asn and Gln. The "acidic" amino acids are Glu and Asp. The "basic" amino acids are Lys, Arg and His. As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"CONSERVATIVE AMINO ACID SUBSTITUTION" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

"IDENTICAL," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. The percent identity between two amino acid sequences can also be determined using the algorithm of Meyers and Miller.

PNH and Hemolytic Diseases

As used herein, the term "HEMOLYTIC DISEASES" refers to any disorder or disease in which cellular lysis, cellular damage and inflammation play a role in the pathology of the disease. Hemolytic disease is also an inflammatory disorder or disease wherein AP activation causes cellular lysis, cellular damage, and inflammation. Hemolytic diseases include diseases characterized by pathologic lysis of erythrocytes and/or platelets. Anucleated cells such as erythrocytes and platelets are subject to full lysis. Lysis of erythrocytes releases hemoglobin which has pathological outcome for blood and organs. Nucleated cells such as neutrophils, monocytes, T lymphocytes can be attacked by the MAC but do not undergo full lysis.

"INTRAVASCULAR HEMOLYSIS" refers to the lysis of anucleated and nucleated cells which is caused by AP activation and the associated production and deposition of C5b-9 on cell surfaces.

"EXTRAVASCULAR HEMOLYSIS" refers to lysis of cells due to C3b deposition and removal via complement receptors. C3b is produced via the activation of the classical and the alternative pathway. This invention is focused on C3b produced via the alternative complement pathway.

"TRAP ANTAGONIST" is a receptor-Fc fusion protein consisting of the antibody Fab fused to the Fc portion of human IgG1. In a preferred embodiment, an expression plasmid encoding the target protein is transfected into CHO cells, which secrete the trap antagonist into the culture medium. The resulting antagonist trap binds its ligands using the binding domains of high-affinity receptors, having greater affinity for properdin.

"SUBCUTANEOUS ADMINISTRATION" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue. There are various formulations available specially those skilled in the art are well aware of such formulations.

"TISSUE INJURY" refers to the tissue where C5b-9 (MAC) is found to injure the tissue. Tissue injury is caused by the MAC and can be inhibited by the antibodies that prevent MAC formation. One example shown in the application is the quantifiable death of erythrocytes in a time dependent manner in the presence of normal human serum that contains physiological levels of complement components. This demonstration of lysis of cells is quantifiable by the loss of scattering at OD700. Nucleated cells present in tissues are also injured by complement similar to erythrocytes. Inhibition of erythrocyte lysis and therefore tissue injury can be prevented by the use of antibodies of this invention. Tissue injury can occur in any part of the body/organs and can lead to pathological outcome such as arthritis. In hematological disorder where all cells that lack the GPI are subject to MAC attack, tissue injury and damage can be prevented by the use of such antibodies. This definition can be extended to many diseases where tissue injury occurs as a result of AP activation but not CP activation.

Embodiments described herein relate to methods for treating a subject suffering from hemolytic disease, hemolytic related, or PNH-like, condition by administering to an afflicted subject an effective amount of one (or several) of a specific genus of inhibitory antibodies that inhibit intravascular and extravascular lysis mediated only the alternative complement pathway without affecting the classical complement pathway. The antibodies of this genus have been identified and selected, from a variety of antibodies inhibiting the complement system, for their specific and unique effect on specific components of the alternative pathway. The inhibitory antibodies of the claimed genus are selective for the alternative complement pathway. The antibodies produced from this combination of selection criteria are useful for a multitude of hemolytic conditions.

Both, the classical and the alternative pathways are independent. Lectin or the MBL pathway is part of the classical pathway. Both pathways independently generate C3b, C3a, C5b, C5a, and C5b-9. Antibodies of the present invention inhibit C3b and C5b-9 formation, molecules produced via both pathways. These monoclonals do not inhibit classical pathway derived C3b and C5b-9 whether the amplification loop is a part of the process or not. This invention leaves the C3b produced via the classical pathway intact for host defense such as opsonization. This invention leaves the C5b-9 produced via the classical pathway intact for host defense.

Prior art uses inhibitors do not appear to be selective because, the classical pathway feeds into the alternative pathway and also work in co-ordinance with the alternative pathway. Classical pathway uses the amplification loop of the alternative pathway. Inhibitors of AP developed in such a setting would inhibit the amplified activity of the classical pathway.

Uniquely, complement attack does not damage normal cells, abnormal cells are those that lack the important regulators of the complement system such as CD55 and CD59. These abnormal cells are found in PNH. PNH cells lack CD55 and CD59, our invention shows that both CD55 and CD59 are absent in nearly all types of cells including erythrocytes, platelets, T-lymphocytes, neutrophils, and monocytes—but the total population of each type of cells may be different—for example, the % of abnormal cells can vary from less than 1% to 10% or 10% to 100%.

In PNH, abnormal erythrocytes undergo lysis and release hemoglobin as a result of AP activation. The released hemoglobin can be damaging to kidneys. Breakthrough due to lysis of erythrocytes is considered important and drugs have been discovered and currently being used to control intravascular hemolysis. This drug due to its downstream action does not prevent extravascular hemolysis and therefore patients continue to remain anemic.

To prevent extravascular hemolysis from taking place; several major categories of complement inhibitors can be developed; a) Classical pathway inhibitors that prevent C3b deposition produced via the classical pathway onto the cell surface, b) Classical pathway inhibitors that prevent C3b formation produced via the amplification loop, c) AP inhibitors that prevent the formation of CP derived C3b formation, and d) AP inhibitors that prevent C3b produced via the alternative pathway without affecting the classical pathway. The inventor of the current application claims those inhibitors that selectively target the alternative pathway derived C3b formation without affecting the classical pathway derived C3b formation. The rationale for such an approach is that such inhibitors would leave the C3b produced via the Classical pathway for host defense. The present inventors claim a genus of monoclonal antibodies that prevent the formation of C3b only via the alternative pathway without affecting the classical pathway derived C3b.

To prevent intravascular hemolysis; several major categories of complement inhibitors can be developed; a) Classical pathway inhibitors that prevent C3b deposition produced via the classical pathway onto the cell surface, b) Classical pathway inhibitors that prevent C5b-9 formation produced via the amplification loop, c) AP inhibitors that prevent the formation of CP derived C5b-9 formation, and d) AP inhibitors that prevent C5b-9 produced via the alternative pathway without affecting the classical pathway. The inventor of the current application claims those inhibitors that selectively target the alternative pathway derived C5b-9 formation without affecting the classical pathway derived C5b-9 formation. The rationale for such an approach is that such inhibitors would leave the C5b-9 produced via the Classical pathway for host defense. The present inventors claim a genus of monoclonal antibodies that prevent the formation of C5b-9 only via the alternative pathway without affecting the classical pathway derived C5b-9.

C3b and C5b-9 are produced via both the classical and the alternative pathways. The two C3 convertases (CP C3 convertase and AP C3 convertase) with different molecular structure have been identified; (C4b2a) and (PC3bBb). These C3 convertases cleave C3 and generate two different types of C3b molecules. Since both complement pathways are independent, this invention only targets C3b production via the alternative pathway without affecting the C3b produced via the classical pathway or from CP amplification loop. A genus of monoclonal antibodies that selectively targets the alternative pathway derived C3b are the focus of the current invention.

Antibodies of the present invention would control extravascular hemolysis in vivo and its associated clinical outcomes such as increased reticulocyte counts, hemoglobin (HgB) and LDH in clinical trials. In certain embodiments, the present invention comprises a method of treating a subject having hematological disorder wherein erythrocytes, neutrophils, monocytes, platelets and T lymphocytes are deficient in GPI linked proteins, the method comprising administering an effective amount of an inhibitor that inhibits the alternative complement pathway to prevent the formation and deposition of C3b, PC3b, PC3bBb and P(C3b)n(Bb)n. Such an action is important for preventing extra- and intra-vascular hemolysis and episodes of hemolytic crisis. In other embodiments, the invention comprises a method of treating a subject previously treated with Eculizumab or a comparable drug wherein the subject already is exhibiting extravascular hemolysis, the present invention is expected to dis-assemble to convertase and halt the progression of extravascular hemolysis.

In certain embodiments, the methods of the present invention comprise treating a subject having complement-mediated hemolytic disorder affecting blood cells, wherein the subject exhibits at least one of the following characteristics; a) the subject exhibits signs or symptoms continued loss of red blood cells by ongoing or intermittent intravascular hemolysis and/or extravascular hemolysis; b) the subject has red blood cells opsonized by fragments of C3; c) the subject requires periodic blood transfusions; c) the subject has low normal or below normal levels of hemoglobin; e) the subject has low normal or below normal levels of platelets; f) the subject has high normal or above normal reticulocytes; g) the subject has high normal or above normal bilirubin; h) the subject has iron overload or is at risk of iron overload.

As preferred embodiments useful to accomplish the above methods, the present invention provides agents and compositions that inhibit the activity of the complement alternative pathway. Such agents and compositions comprise fusion proteins carrying the binding regions of the antibodies from the claimed genus and or antibodies themselves. These agents are expected to prevent the initiation of C3 convertase formation and formation of C3b, prevent deposition of C3b onto cells that lack the GPI linked proteins. As a result, extravascular hemolysis is down-regulated, number of transfusions are reduced, cytopenia is reduced, and intravascular hemolysis is reduced. In another aspect of the present invention where reduction in cytopenia is claimed, cytopenia includes leukocytopenia, thrombocytopenia, erythrocytopenia, leukocytopenia, lymphocytopenia, and neutropenia. These processes can occur as a result of cellular aggregate formation and removal of such aggregates from subject's circulation. Reduction in cell number can also occur due to extravascular hemolysis.

In preferred embodiments, the inhibitor of the complement alternative pathway may comprise a fusion of the "Fab", or a fragment comprising at least the variable region of the antibody or a biologically active fragment thereof to the Fc region of the antibody. In another aspect of the current invention, the inhibitor of the complement alternative pathway may comprise only the blocking Anti-C3b antibody, Anti-Factor Bb antibody, Anti-Properdin antibody, and Anti-Factor D antibodies specially those that block both the formation of C3b and C5b-9. If such antibodies block the formation of C3b and not the formation of C5b-9, then such antibodies are excluded from the current invention. The selected antibodies of the genus should only inhibit the alternative pathway but not the classical pathway.

In a particular preferred embodiment, the inhibitor of the complement alternative pathway is a genus of neutralizing monoclonal antibodies that have the following characteristics:

Inhibit the alternative pathway derived C3b and do not inhibit the classical pathway derived C3b. The classical pathway derived C3b is required for opsonization and for host defense. Thus the selected genus of the antibodies perform specific function.

These antibodies doe not inhibit the classical pathway and therefore do not inhibit the formation of C3b via the classical pathway.

The present invention provides in one aspect a method of treating a subject having a complement-mediated hemolytic disorder affecting blood cells, the method comprising administering an effective amount of the antibody and its antigen binding fragments that inhibit activation of the complement alternative pathway, wherein the antibody inhibits the formation of both the C3b and C5b-9 responsible for extravascular and intravascular hemolysis respectively.

In certain embodiments of any of the methods described herein, the subject has one or more of the following characteristics: a) the subject exhibits signs or symptoms of cytopenia by ongoing or intermittent intravascular hemolysis and/or extravascular hemolysis; b) the subject has cell bound C3b wherein the cell is selected from the group comprising leukocytes, lymphocytes, erythrocytes, platelets, and monocytes, basophils; c) the subject requires periodic blood transfusions; the subject has low normal or below normal levels of hemoglobin; the subject has low normal or below normal levels of platelets; the subject has high normal or above normal reticulocytes; the subject has high normal or above normal bilirubin; or the subject has iron overload or is at risk of iron overload; or the subject has high number of dead cells.

In some embodiments, the method includes administering an effective amount of a monoclonal antibody selected from the collection of antibodies of this invention which inhibit the activity of the complement alternative pathway and therefore;

Increase in the total number of cells to normal levels.

Increase the total number of surviving red blood cells increase to normal levels.

Increase the total number of neutrophils to normal levels.

Increase the total number of monocytes to normal levels.

Increase the total number of T-lymphocytes to normal levels.

Increase the total number of platelets to normal levels.

Decrease the total number of dead cells, increase the total number of healthy cells.

Decrease the total number of cellular aggregates.

Decrease in the total LDH to normal levels.

Decrease bilirubin to normal levels.

Decrease hemoglobin in plasma.

Decrease in C3a, C3b, C5a, C5b, C5b-9, and sC5b-9 levels.

Decrease in activated cells.

Decrease in inflammatory cytokine levels.

Decrease in cellular activation.

In some embodiments, the antibodies of the current invention dampen and/or inhibit the activation of AP without inhibiting CP. They inhibit alternative pathway-dependent lysis and activation of cells involved in inflammation, inhibit production of inflammatory molecules and ultimately inhibit a myriad of pathologies associated with various hemolytic diseases. These antibodies also inhibit the formation of C3b responsible for extravascular hemolysis and intravascular hemolysis mediated via C5b-9.

C3b of alternative complement pathway (C3b)—This key molecule is important in the amplification of the alternative pathway. When associated with a disease state, AP activation causes C3b to be produced and deposited on various cells, including blood cells. This, in turn, causes extravascular lysis of erythrocytes and platelets, the root cause of erythrocytopenia and thrombocytopenia respectively. For this reason, pathological overproduction of C3b is detrimental and must be inhibited or controlled. C3b is also deposited on neutrophils, monocytes, and T-lymphocytes. Deposition of C3b on these nucleated cells does not cause lysis of these cells but causes cell damage and equivalent to tissue injury. C3b receptors are found on these nucleated cells and the density of such receptors is increased during complement activation and diseases. As a result, such cells become dysfunctional. It is the invention of this application to demonstrate that not only erythrocytes would be subject to lysis but also the platelets would be subject to lysis. Both erythrocytes and platelets are a nucleated cells. The nucleated cells such as neutrophils, monocytes, and platelets—they all would bind C3b and are removed via extravascular lysis.

We believe that if C3b formation is inhibited only via the alternative pathway, no C3b produced via the alternative pathway will be available for deposition on cells and therefore would inhibit cell loss via extravascular lysis and/or removal by the host liver/or spleen. Inhibition of removal would mean cytopenia which includes all cells will be inhibited. In hematological disorders such as PNH, not only erythrocytopenia is observed, but also thrombocytopenia, neutropenia, monocytopenia, lymphocytopenia is observed. It is important to address removal of leukocytes and platelets as these are new findings.

Neutrophils and other cells bear C3b receptors and therefore bound C3b could be detected with the anti-C3b antibody. Neutrophils coated with C3b are incapable of fighting infections therefore the neutralizing monoclonals of the claimed invention would prevent infection.

Similar to erythrocytes, platelets are also anucleated and therefore have the ability to lyse.

C3b produced via the classical pathway is designated as (C3b) to differentiate this C3b from those produced via the alternative pathway. C3b would remain intact for opsonization and removal of bacteria and therefore must not be inhibited. The antibodies of the current genus do not inhibit the classical pathway and therefore do not inhibit associated side products such as C3b, C3a, C5b, C5a, and C5b-9 produced via the classical pathway. The process of opsonophagocytosis begins with deposition of C3b on the surface of cells and the subsequent uptake by phagocytic cells. Inappropriate and/or uncontrolled production of C3b leads to inappropriate and/or uncontrolled opsonophagocytosis.

C3a—The C3a molecule is a peptide with a molecular weight of 9,000 Da and a high affinity for C3a receptors (C3aR). C3aRs are present on neutrophils, monocytes, platelets, mast cells, and T lymphocytes. Binding of C3a to C3aR activates the release of inflammatory molecules from the triggered/activated cells. Upon activation, these cells: a) form intra- and inter-cellular aggregates, b) invade the normal tissue and host themselves causing pathology, and c) release inflammatory mediators such as TNF-$\alpha$, IL_1, 11-18, IL-27, peroxides and proteases that can degrade the matrix and initiate inflammation and tissue destruction. For example activated/triggered monocytes express CD11b and release Tumor Necrosis Factor alpha (TNF-$\alpha$). Activated monocytes can form aggregates with platelets. Activated neutrophils also express CD11b and release peroxides and neutrophil elastase. Activated platelets express a higher concentration of CD62P and form aggregates with neutrophils and monocytes. Both mast cells and T lymphocytes are also activated by C3a. C3a initiates the release of TNF-$\alpha$ from monocytes. TNF-$\alpha$ is known to play a key role in the pathological outcomes and conditions. Platelets also bear C3a receptors. Upon activation by C3a, platelets express CD62P, an activation marker. CD62P is responsible for inter cellular aggregate formation. These aggregates are removed from circulation, which ultimately leads to thrombocytopenia.

C5a also plays a role in activation of platelets. Regardless of the method of platelet activation, activated platelets express CD62P, which is also called P-selectin. P-selectin also mediates platelet-monocyte conjugation. This binding triggers the release of tissue factor from monocytes.

C5a/C5b—AP C5 convertase (P(C3b)n(Bb)n) cleaves C5 and produces C5a and C5b. C5a is known to activate neutrophils and monocytes as C3aR and C5aR receptors have been found on these cells. Upon activation, neutrophils and monocytes produce inter and intracellular aggregates and release inflammatory markers such as neutrophils elastase, peroxides and a variety of matrix proteases that degrade the tissue matrices. Similar to C3a, C5a also causes the release of inflammatory mediators relevant to several pathologies and associated hemolytic diseases.

C5b-9 and sC5b-9—These complexes are also called "MAC", the C5b-9 is a complex that forms on the cell surface and causes tissue injury. As demonstrated in FIG. 6, rabbit erythrocytes (rRBC) activate the AP in whole blood. In response, C5b-9 is integrated in the cell membrane, causing lysis of these cells by human complement. This assay represents a way of demonstrating tissue injury using an erythrocyte hemolysis assay. The sC5b-9 is a MAC complex that is formed by the association of protein S to C5b. C5b binds S instead of depositing on a cell surface. Protein S enables the formation of "soluble MAC," abbreviated as sC5b-9. Soluble MAC also activates platelets and other cell types.

C3a and C5a activates cells, activated cells express markers such as CD62P and CD11b. These activated cells form aggregates. Aggregates are removed from circulation leaving patient cytopenic.

The antibodies of the present invention can prevent AP derived formation of C3a, C3b, C5a, C5b, and C5b-9. As a result, cellular activation is prevented. If there is no activation, there is no release of inflammatory markers. Thus, the antibodies of this invention are capable of blocking, preventing the progression of the disease.

Role of Alternative Pathway in Hemolytic Diseases

Based on the available literature and associated data, it appears that in chronic hemolysis, complement activation is mediated predominantly via the formation of C5b-9 on cell surfaces. It does not differentiate between the classical pathway derived or the alternative pathway derived. This invention targets the C5b-9 formed via the alternative complement pathway, but not the classical complement pathway. This invention would leave the classical pathway intact for host defense against infection.

Hemolytic diseases include those in which lysis of erythrocytes results in a release of hemolglobin. Such actions reduce the total concentration of erythrocytes in the blood. Paroxysmal nocturnal hemoglobinuria ("PNH") is a rare hemolytic disease. It is an autoimmune disorder of the blood wherein erythrocytes are destroyed by activities of the body's own complement pathways. PNH results from somatic mutations which render cells unable to synthesize the glycosyl-phosphatidylinositol ("GPI") anchor. The GPI anchor protects cells against complement attack. PNH cells are deficient in complement-regulating surface proteins that include the decay-accelerating factor ("DAF"), or CD55, and membrane inhibitor of reactive lysis ("MIRL"), or CD59.

In PNH, lysis of erythrocytes causes a pathologic reduction in the total erythrocyte count (i.e., hemolytic anemia). The presence of hemoglobin in the urine (hemoglobinuria) is particularly evident after sleeping and usually causes the urine to appear dark in color. Subjects with PNH will also have free hemoglobin in their bloodstream (hemoglobinemia). Hemolytic anemia is due to intravascular lysis of red blood cells by complement component C5b-9 (MAC). Reduced numbers of erythrocytes and platelets cause dysphagia, fatigue, erectile dysfunction, thrombosis and recurrent abdominal pain.

Erythrocyte Lysis—Erythrocytes are anucleated cells and are responsible for maintaining the hemoglobins. These cells are known to be subject to complement attack in PNH due to the absence of CD55 and CD59 from the cell surface. These cells are therefore subject to C3b deposition and removal via extravascular lysis. These CD59 deficient cells also allow deposition of C5b-9 and erythrocyte removal via intravascular lysis. Lysis results in hemoglobin release from these erythrocytes causing hemolytic anemia and therefore decrease in the number of erythrocytes in general causing erythrocytopenia. Thus erythrocytes are subject to removal via both extra- and intra-vascular lysis. Additionally, excessive free hemoglobin can cause kidney damage and system loss of iron. Haptoglobin helps ameliorate the situation by binding free hemoglobin and facilitating enzymatic degradation of the bound hemoglobin.

Pathologic intravascular hemolysis, such as that associated with PNH and other hemolytic diseases, often results in concentrations of free hemoglobin high enough to completely deplete haptoglobin. Once haptoglobin has been depleted, the burden is then on the kidneys to re-absorb the free hemoglobin. Once the kidneys reach their capacity for hemoglobin re-absorption, hemoglobinuria begins. The release of free hemoglobin during intravascular hemolysis results in excessive oxidation of nitric oxide (NO) to nitrate ($NO_{3-}$) The depletion of NO causes enhanced smooth muscle contraction, vasoconstriction and platelet activation and aggregation. The systemic consequences of excess free hemoglobin in blood also effect abdominal pain, erectile dysfunction, esophageal spasm, and thrombosis.

As a routine laboratory test, blood smears are, generally, evaluated to identify morphologic abnormalities of RBCs (Red Blood Cells), reticulocyte count (to determine bone marrow compensation for RBC loss), lactate dehydrogenase (LDH), and levels of free hemoglobin (from hemolysis). Concentrations of bilirubin, haptoglobin, hemosiderin, and free hemoglobin can measure the extent of hemolysis and help differentiate between intravascular vs. extravascular hemolysis. RBC numbers, levels of RBC (i.e., cell-bound) hemoglobin, and hematocrit are often evaluated to determine the extent of any anemia and/or any other associated symptom of hemolytic disease. Levels of Lactate Dehydrogenase (LDH) can also provide some information with regards to the extent of ongoing cell death.

Lysis of erythrocytes sometimes could give erroneous and inconsistent results due to persistent extravascular and intra-vascular hemolysis. Therefore cells that do not undergo lysis would be better for determining the clone size in PNH patients. Such examples are neutrophils and other mononuclear cells.

Convertase Laden Erythrocytes—In PNH, erythrocytes that lack the CD55, would be prone to C3b deposition. Such cells not only have the C3b but also have the entire C3 convertase. Antibodies of the current genus, prevent the formation of C3b, C3bBb, PC3bBb formation and therefore would prevent the lysis of erythrocytes via extra- and intra-vascular hemolysis. Thus these antibodies would prevent the formation of both the C3 and C5 convertases.

Antibodies of the current invention, those that selectively prevent the formation of C3b and C5b-9 produced via the alternative pathway would inhibit extra- and intra-vascular hemolysis with resultant benefit in total anemia. Platelet Lysis—Platelets are anucleated and therefore subject to complement attack via the alternative pathway. Similar to erythrocytes, platelets are also destroyed via the similar mechanism. Lysis of platelets would occur in PNH patients where platelets lack the CD55 and CD59 on its cell surface. Platelet lysis means reduction in platelet number and therefore blood clotting ability of blood in PNH patients. The reduction in platelet number results in increased levels of platelet contents including but not limited to platelet factor 4 (PF4), platelet derived growth factor (PDGF), beta thromboglobulin, P-selectin. This includes all contents that are reported now or in future are covered under this invention. Thus antibodies of the current invention would decrease thrombocytopenia associated with patients with hematological disorders.

Lysis of Nucleated Cells—Under this category fall cells such as Neutrophils, monocytes, and lymphocytes. These cells are known to be CD55/CD59 positive and have recently been considered reliable cells for establishing PNH clone. Often higher percentage of leukocytes are detected with CD59 than shown with erythrocytes. Erythrocytes generally have a lower life span compared to leukocytes. Nucleated cells do not lyse and therefore are present in blood for longer duration compared to erythrocytes and therefore are more confirmed markers of PNH.

Neutrophils bear C3b receptors and therefore would bind such molecules. We show increased staining of C3b, properdin, and Bb on neutrophils indicating that the convertase forms on such cells. Antibodies of the current invented genus of antibodies is capable to preventing the formation of alternative pathway derived C3 convertase but not classical pathway derived C3b. Similar finds have been noted on all nucleated cells. It was surprising to note that nearly all nucleated cells showed heavy staining with both C3b and C5b-9. Both of these molecules deposit on cell surface as a result of AP activation.

It is the intent of the proposed invention to prevent the formation and deposition of C3b and C5b-9 on the nucleated and non-nucleated cells. AP specific selected antibodies inhibit the pathway upstream and prevent the deposition of both molecules that cause extra and intravascular lysis and damage. Nucleated cells when laden with C3b and C5b-9 are likely to become dysfunctional and recognized lend themselves to death. Dead cells are recognized by the stain specific for cell death.

Role of C3a and C5a in Inflammation: Elevated levels of C3a and C5a are predicted in PNH due to the continuous activation of the alternative pathway leading to lysis of erythrocytes. C3a and C5a have potent pro-inflammatory and immuno-regulatory functions. They increase vascular permeability and serve as chemo attractants, which promote soft tissue swelling. The anaphylatoxins activate neutrophils and monocytes, which results in the production of pro-inflammatory mediators such as TNF-α IL-1, IL-6, IL-8, and IL-17 [47-50]. C5a is a potent chemotactic protein that induces neutrophil chemotaxis, de-granulation, neutrophil elastase release, and superoxide generation. Neutrophils contain a potent arsenal of vasoactive, proteolytic and cytotoxic substances, which are produced to mediate many of the manifestations of inflammation and cellular lysis in hemolytic diseases such as PNH. Compounds of the current invention inhibit the detrimental inflammation, tissue injury, and cellular lysis.

Blood Transfusion and Anti Complement Antibodies—

Blood cell transfusion is given when the patient has too few red blood cells (anemia). Blood tests in PNH show changes consistent with intravascular hemolytic anemia: low hemoglobin, raised lactate dehydrogenase, raised reticulocytes (immature red cells released by the bone marrow to replace the destroyed cells), raised bilirubin (a breakdown product of hemoglobin), and decreased levels of haptoglobin. Anemia causes weakness and tiredness. In severe cases, it can cause shortness of breath or a rapid heartbeat. Transfusions are usually used when the hemoglobin level is less than 8 grams per deciliter. Sometimes instead of a transfusion, you may get a red blood cell growth factor—a drug that helps your body make more red blood cells. This growth factor is called erythropoietin (Procrit®, Epogen®, Aransep®). Platelet, another anucleated cell would also decrease in number based on complement-mediated lysis. Doctors prescribe platelet transfusions to keep the platelet count above 10,000 to 20,000 (per cubic millimeter). Transfused platelets last only two to three days. The antibodies of the current invention are expected to preserve the added platelets and prevent the destruction of platelets made by the patient's body.

White blood cell (granulocyte) transfusions are rare. This is because the granulocytes last only a few hours in the bloodstream. Donated white blood cells must be used right away and do not last long. A common example is filgrastim (Neupogen®) for increasing the number of neutrophils/leukocytes. The antibodies of the claimed genus can help prevent the damage and lysis of cells that are increased by the additives.

To prevent cytopenia in general, the antibody of the claimed genus could prevent C3b formation and deposition and C5b-9 formation and deposition, the two main functions of the AP derived moieties are important for hemolytic disorder whether it is with or without the additives.

Role of Complement System Activation in PNH and Other Hemolytic Diseases and Conditions Elevated levels of C3a, C5a, C3b, C5b, and C5b-9 can gauge the level of activation, inflammation and hemolysis in disease conditions. Examples of complement-associated disorders involving hematologic disorders include, but are not limited to: Catastrophic anti-phospholipid syndrome (CAPS), Cold Agglutinin Disease (CAD), which increases c3b, Thrombotic thrombocytopenic purpura (TTP), which increases CD46, factor H, and factor I, Idiopathic thrombocytopenic purpura, where C3 and C4 detected are on platelets, Serum sickness, where abnormal factor H leads to increased glomerular C3 deposition, Endotoxemia, Sepsis, Atypical hemolytic uremic syndrome (ahus), where there is enhanced formation of c3bbb convertase and resistance to complement regulators, Paroxysmal Nocturnal Hemoglobinuria (PNH), where it has been shown a C5 antibody treatment reduced thromboembolism risk, Septic shock, sickle cell anemia, which elevates c3b, Hypereosinophilic syndrome, which increases c5a, anti-phospholipid, Autoimmune lymphoproliferative syndrome, Dego's disease, where c5b-9 is activated, Evan's syndrome, essential mixed cryoglobulinemia, and pure red cell aplasia. Antibodies of the invention genus of antibodies, selected with The Screening Method (see Page 23), can prevent local damage and have shown benefit in whole blood models of the disease. Antibodies of the current invention prevent blood inflammation and cellular lysis and the associated maladies.

Classical Pathway Versus Alternative Pathway C3 Convertases and PNH

Both the classical and the alternative pathway C3 convertases are responsible for the cleavage of central C3. Eculizumab inhibits both the CP and the AP at the C5 level and does not inhibit the formation of C3a and C3b. This is a severe disadvantage of Eculizumab since both excess C3a and excess C3b have been implemented in several disease conditions. C3b produced by both, or either, pathways can coat cells. These cells can then be removed via the opsonization process.

Conceptually, inhibition of the AP, but not the CP, will allow for CP dependent production of C3b which may be required, in case of infection, for opsonization via the CP. The antibodies of the invention genus of antibodies only inhibit the AP. They do not inhibit the CP or any amplification loop of the CP. Inhibition of C3b is essential to prevent extravascular lysis (and effective removal) of erythrocytes, while CP dependent C3b is essential to host defense. In diseases such as PNH, it is the alternative pathway that is problematic, not the classical pathway. Thus, to combat overproduction of these proteins, the best treatment is to shut down the alternative pathway alone. Present thinking on the subject is that the two pathways and inextricably connected, and that it may not be possible to shut down the AP without inhibiting the CP. The present invention presents a challenge to the present thinking and offers a method for shutting down the AP without, to any degree, inhibiting the CP. Any treatment that shuts down or significantly inhibits the classical pathway will jeopardize the body's ability to fight infection. C3b production is needed for the removal of unwanted cells, such as infectious bacteria. Therefore, it is desirable and advantageous to preserve production of CP dependent C3b while inhibiting AP dependent C3b.

Selection and Identification of the Claimed Genus of Antibodies

While both the classical and alternative pathways produce C3a and C5a, the present invention selectively inhibits AP produced C3a and C5a. Equimolar concentrations of C3a and C3b are produced as a result of the C3 cleavage. Thus inhibition of C3b formation in vitro can be demonstrated by the assays described herein. The formation of C3b evidences the concurrent formation of C3a (and vice versa). Any antibody, targeting a component of the C3 convertase complex, which acts to inhibit the cleavage of C3 into C3b and C3a, will inhibit C3b and C3a in equal measure.

Inhibition of C3a production will also inhibit all of the activities of C3a. Such activities include: subsequent activation of neutrophils, monocytes, platelets, basophils, and T lymphocytes, as well as production of inflammatory markers. (See FIGS. 13 through 18.) C3b deposits on the cell surfaces via C3b receptors. C3b deposition is required for opsonization/removal of erythrocytes and other cells which cause pathological outcomes in other hemolytic diseases U.S. Pat. Nos. 6,333,034 & 7,423,128 claims antibodies that inhibit both CP and AP mediated complement activation and therefore host defense is compromised. These antibodies play in role how antibodies prevent the formation of properdin oligomer. Properdin is a thrombospondin type 1 repeat and consists of six repeats of thrombospondin type1. These antibodies inhibit the binding of properdin to C3b and prevent the formation of C3c. C3b cleavage results in the formation of C3c. Thus these antibodies prevent the cleavage of C3b.

In another aspect, the alternative pathway specific antibody of the present invention can bind to the alternative pathway protein without reducing the levels of that protein in the human.

Therapeutic Antibodies

Figure 1:
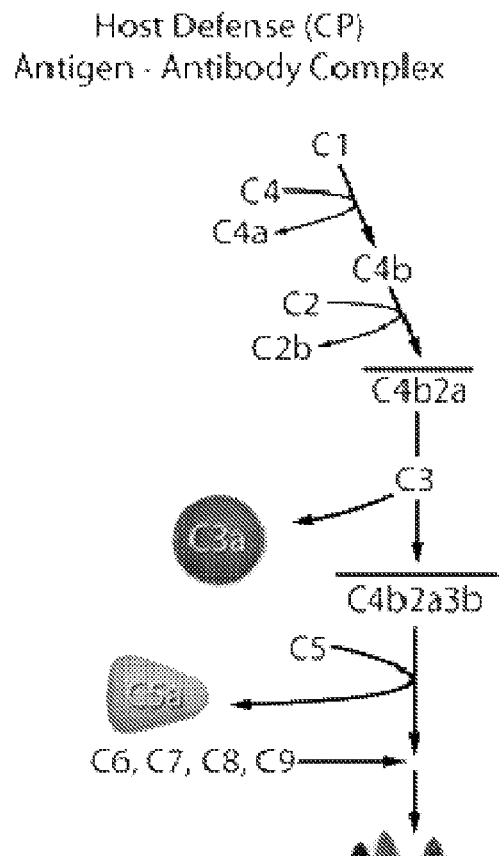
FIG. 1 is a schematic showing the complement cascade of the classical pathway and the alternative pathway. Lectin pathway is not shown as it is not the part of the invention. The FIG. 1 shows a schematic representation of the CP and the AP. In this figure, we show that both CP and AP are distinct and not connected. The schematic only shows how the antibodies of the current genus work and not the way antibodies of the other invention work. AP amplification is shown in the upper right hand side and consists of PC3b, PC3bB, PC3bBb. As can be seen in the schematic, PC3bBb then acts to perpetuate the cycle by cleaving C3 into more C3b which binds to P to again form PC3b. Application of the invention completely inhibits the alternative pathway without affecting the classical pathway by specifically targeting the components of this amplification loop. These antibodies prevent the amplification loop of the alternative complement pathway without affecting the classical pathway (as shown on the left side of the schematic in FIG. 1).
Figure 1:
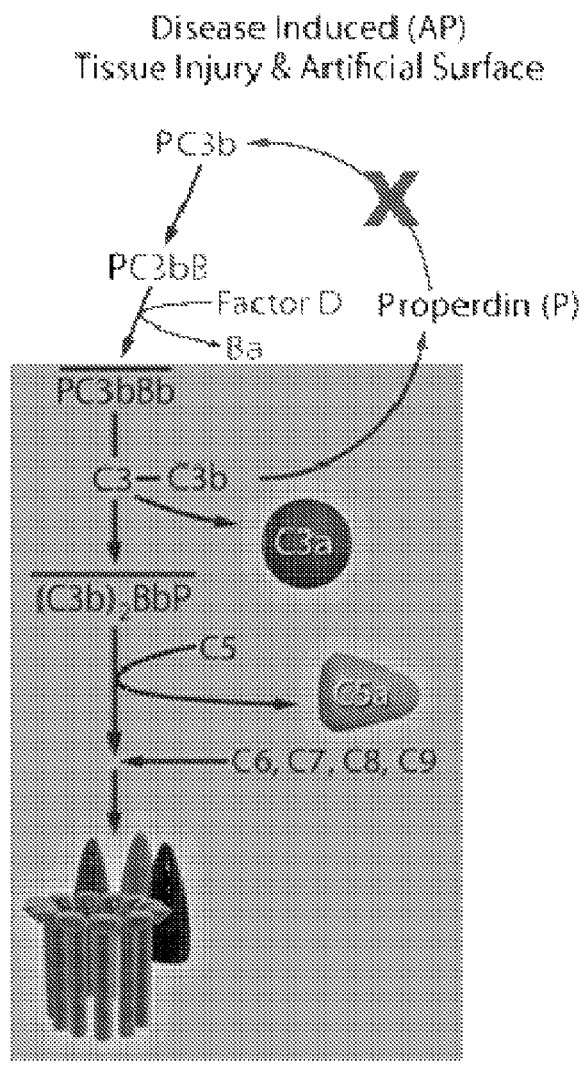

Referring to FIG. 1, we show that both CP and AP are distinct and not connected. It is known that CP has an amplification loop and that connects the CP and the AP. The schematic only shows how the antibodies of the current genus work and not the way antibodies of other inventions work. AP amplification is shown in the upper right hand side and consists of PC3b, PC3bB, PC3bBb. As can be seen in the schematic, PC3bBb then acts to perpetuate the cycle by cleaving C3 into more C3b which binds to P to again form PC3b. Application of the antibodies selected using the screening method described herein completely inhibits the alternative pathway without affecting the classical pathway by specifically targeting the components of this amplification loop. These antibodies prevent the amplification loop of the alternative complement pathway without affecting the classical pathway (as shown on the left side of the schematic in FIG. 1).

Based on the old conversion of pathway at C3 theory, those with ordinary skill in the art would expect any activation of the classical pathway to invariably have the effect of triggering and propagating the alternative pathway. This is because the two pathways are believed to "overlap" at the starting point of the C3. According to this theory, C3b produced via the classical pathway participates in the AP amplification loop. The genus of antibodies selected using the method described herein specifically targets components of the alternative pathway amplification loop in such a way as to inhibit the alternative pathway regardless of whether or not the AP amplification loop has been otherwise triggered by the classical pathway. Thus, for example, anti-C3b antibodies described herein only inhibit the AP and not the CP amplification loop or the CP propagation.

The "Screening Method": Selection of Antibodies that Inhibit the Alternative Complement Pathway, do not Inhibit the Classical Complement Pathway, and are Specific for Components of the AP C3 Convertase Antibodies specific for complement proteins belonging to the alternative pathway (whether part of the CP amplification loop or an alternative pathway by itself), such as C3b, P, Ba, and Bb can be screened using a "Screening Method" described herein to select antibodies to inhibit alternative complement pathway without affecting the CP or the amplification loop of the CP. C3b, P, Ba, and Bb are large proteins of, respectively, 210K, 50K, 33K, and 66K molecular weight. One skilled in the art can generate millions of antibodies to each of these proteins. Production of antibodies to a target is, by itself, meaningless without further selection of those antibodies as having a specific therapeutic function.

In some embodiments, the Screening Method can include a two-stage screening process. The first stage utilizes three successive screening assays to identify Type AP antibodies (antibodies which specifically inhibit the AP). The selection process leads to identification of alternative pathway specific antibodies which are similar in functionality but targeted to a wide variety of antigens. These selected antibodies cannot be differentiated based on the targets they bind to or the species of animals in which they were raised. Upon sequencing, it is clear that such antibodies have widely different CDRs (the regions involved in binding to antigens). The functionality, and ultimate therapeutic value, of these antibodies can't be defined by their sequences alone. The Screening Method described herein can identify and define a genus of antibodies against Properdin (P), Factor C3b (C3b), and/or Factor B (Ba, or Bb) which have the desired functionality and effect.

A1) Step 1: Selection Based on Function

Three distinct types of antibodies can be identified using specific assays. The antibodies can be referred to as Type CP, Type CP/AP, and Type AP, and are defined as follows.

Type CP: These inhibit the classical pathway but not the alternative pathway.

Type CP/AP: These inhibit both the classical pathway and alternative pathway.

Type AP: These inhibit the alternative pathway but not the classical pathway.

Identification of these three different types of complement inhibiting antibodies is accomplished using three different assays; a CP only assay, a combined CP and AP assay, and an AP only assay.

Type CP

For classical pathway activation, antibody sensitized sheep cells are used as an activator in 1% normal human serum in the presence of Ca2+/Mg2+. The calcium ions are required for the activation of the classical pathway for the initial trigger of the C1q/C1r/s complexes. CP will not occur in the absence of the Calcium ions. Mg2+ is required for alternative pathway activation. In 1% normal human serum containing Ca2+/Mg2+, only the CP proceeds to completion. Without the requisite levels of NHS which is 10%, the alternative pathway will not have a significant presence. FIG. 2, Assay-1 shows that shows that CP activation leads to the lysis of antibody sensitized sheep red blood cells. Antibody bound sRBCs act as a trigger for the classical pathway. The observed CP activity is isolated from AP activity by using a 1% buffer solution containing Ca2+ and Mg2+. FIG. 6 also shows that none of the selected antibodies materially inhibit CP mediated hemolysis of the sRBCs in 1% human serum in classical pathway condition.

Type CP/AP

For classical pathway activation, along with the amplification loop of the alternative pathway, antibody sensitized sheep red blood cells are used as an activator in 10% Ca2+/Mg2+ in normal human serum. The difference between the assays used to identify Type CP antibodies and those used to identify Type AP/CP antibodies is the concentration of normal human serum which is 10% in Type CP/AP. The concentration of Ca2+/Mg2+ used in the identification of Type AP/CP antibodies, by providing the level of Mg2+ required for AP activation, allows for both the CP and the AP to be active. Antibody sensitized sRBCs only activate the CP. They do not, by themselves, activate the Alternative Pathway. However, in the presence of sufficient NHS, activated CP will utilize the amplification loop of the AP. Thus, the assay system is designed to evaluate the performance of complement inhibitors under conditions in which both pathways are active (FIG. 3, Assay 2 and FIG. 4 Panel B). Under these conditions, the C3b produced via the classical pathway can feed into the alternative pathway causing "amplification of the alternative pathway loop" of the alternative pathway and can serve as a trigger indirectly. In other words, the AP has been activated by the CP. Antibodies that prevent CP initiated activation of the AP have been described in (R Gupta-Bansal, J B Parent, K R Brunden, Molecular immunology. 37(5):191-201). These antibodies reduced hemolysis of the sheep red blood cells in these assays. However, at this stage in The "Screening Method", the antibodies have yet to be differentiated according to how (and where) they inhibit the process. Antibodies which inhibit the classical pathway's activation of the AP by inhibiting any stage of the CP are not included in the selected genus of antibodies. Accordingly, the antibodies that inhibit the classical pathway initiated amplification of the alternative pathway have been excluded from the selected genus of antibodies.

Type AP

Rabbit RBCs (rRBC) are used to activate the AP in 10% normal human serum in the presence of Mg2+ and in the absence of Ca2+. Because the CP requires the presence of Ca2+, the classical pathway will not be active under these conditions. Thus, in 10% NHS in Mg2+, only the AP proceeds to completion. As shown in FIG. 2, Assay-3, AP activation leads to cellular lysis of the rRBCs. It should be noted that this assay demonstrates that the alternative pathway can be activated, and progress to completion, in the absence of active classical pathway function. The AP does not require initiation by the classical pathway in order to proceed. FIG. 4 clearly shows that the invention genus of antibodies inhibits AP dependent hemolysis of rRBCs in 10% normal human serum.

When an antibody's effect on AP activation and progression is observed in isolation, with the AP as a stand-alone process, the information obtained is different than the information obtained from observation of the antibody's effects in conditions where both the CP and the AP are active. The information obtained here is also different than that obtained from observation of the antibody's effect in conditions where only the CP is active.

Analysis of the Three Assays

If the presence of a particular antibody(s) in one of these three assays was found to reduce the rate of hemolysis, it was concluded that that antibody inhibits the pathway, or pathways, which were active in that assay. Thus, for example, if an antibody was found to reduce hemolysis in all three assays, it was concluded that the antibody inhibited both the AP and the CP (Type CP/AP). If an antibody was found to inhibit hemolysis only in assays containing 1% human serum (with Ca2+/Mg2+ buffer) it was concluded that that antibody inhibited the CP but not the AP (Type CP). If an antibody was found to inhibit hemolysis only in the assays containing 10% human serum and Mg2+(but not Ca2+), it was concluded that the antibody inhibited the AP but not the CP.

This is the first stage of The Screening Method. Antibodies passing these selection criteria have been shown to: 1) inhibit the alternative pathway under conditions in which the alternative pathway is active in isolation (i.e., without concurrent activation of the classical pathway), and 2) have no effect on CP activity (either in isolation or when concurrent with AP activity).

The invention uses this combination of assays to first identify Type AP antibodies. However, additional screening steps are needed in order to identify the selected genus of antibodies. Additional screening is necessary because these assays will identify antibodies in both the upstream and the downstream portion of the AP and the CP.

A2) Step 2: Selection of Those Type AP Antibodies which Act on C3 Convertase Formation The second step of the Screening Method is to identify which Type AP antibodies inhibit only the functional activity of AP C3 convertase. In other words, this step identifies those Type AP antibodies which act "up-stream" of the alternative complement pathway system, at the amplification loop of the AP, rather than "down-stream."

This step is accomplished by first establishing a solid phase ELISA based binding assay. This assay allows for the direct detection of C3b and C5b-9 produced via the alternative pathway. Detections of these proteins represent an early component (C3b) and a late component (C5b-9) of the alternative complement pathway. If an antibody inhibits production of C5b-9 but not C3b, it is likely to be acting on the C5 convertase of the AP. By contrast, C3b production will be inhibited by antibodies that inhibit the activity of the C3 convertase. Inhibition of C3b production will also inhibit production of C5b-9 (because C5b-9 is produced downstream of C3b). Thus, Stage 2 of The Screening Method separates antibodies inhibiting C3 convertase (up-stream) from those inhibiting C5 convertase (down-stream).

The Screening Method identified antibodies that selectively inhibit the AP C3 convertase. This stage of selection utilizes an assay in which human serum at 10% in the presence of Mg++ is allowed to incubate over an LPS coating. LPS is a specific activator of the alternative pathway and can allow formation of AP derived C3 convertase and C5 convertase. As shown in FIG. 6, the selected genus of antibodies prevents the formation of C3b, a central component of the alternative pathway amplification loop. FIG. 7 shows that they also inhibit formation of C5b-9.

At the conclusion of the this stage selection process, antibodies that prevent the AP dependent cellular lysis and C3b formation (FIG. 6) are selected as being members of the selected genus of antibodies. These antibodies are defined by the fact that they all: 1) selectively inhibit the alternative pathway without inhibiting the classical pathway (FIGS. 2, 4, and 5), and 2) inhibit the alternative pathway dependent C3b formation, by acting on C3 convertase formation, an upstream component of the AP.

FIGS. 10 and 11 show that the selected genus of antibodies inhibits formation of complement proteins C3a and C5a, respectively.

Selected Genus of Antibodies

Application of the Screening Method has thus far produced several antibodies from the selected genus of antibodies.

C3b as Target Protein

Mouse Anti Human C3b (Anti-C3b)

C3b is a large protein and therefore multiple antibodies can be produced against various segments of this protein. There exist multiple sites where-on an antibody might bind and inhibit the protein's activity in any variety of ways. Depending on how and where an antibody binds to C3b, the effect of that antibody could range from inconsequential to complete inhibition. Injecting a mouse with Human C3b will result in the production of a myriad of mouse antibodies against the Human C3b protein.

The selected genus of antibodies include those that bind to C3b in such a way as to prevent the interaction of C3b with Factor B. The effect of these antibodies is necessarily isolated to the alternative pathway since no such interaction exists within the classical pathway. These antibodies prevent the formation of C3a/C3b, C5a/C5b, and C5b-9/sC5b-9 critical for pathological outcome causing disease initiation and progression. Inhibition of the formation of each of these molecules, by the alternative pathway, has significant physiological consequences. Inhibition of alternative pathway produced C3b (herein referred to as "aC3b") impacts extravascular hemolysis of erythrocytes. The C3b produced by the classical pathway is not inhibited by these antibodies and therefore is required for opsonization of foreign particles/bacteria that are coated with CP produced C3b (herein referred to as "cC3b"). Thus, the selected genus of antibodies prevents the formation of aC3b and not cC3b by such antibodies that have this as a common function. The inhibition of C3a formation has direct effect on monocytes activation and production of TNF-α which is a validated marker of inflammation.

Properdin as Target Protein

As is the case with C3b, Properdin is a large protein with many potential sites where antibodies can bind. Different antibodies binding in different ways and/or on different sites of the Properdin protein, will inhibit either amplification loop of the classical pathway or alternative pathway. Properdin is known to be part of the amplification loop of the classical pathway. Thus, classical pathway activation can be dampened by the use of specific anti-properdin antibodies that inhibit the amplification loop (U.S. Pat. No. 6,333,034). Some antibodies can inhibit the classical pathway activation where interactions of Properdin to C3b, within the classical pathway, become important for classical pathway amplification. (U.S. Pat. No. 6,333,034)

Properdin binds to itself and generates aggregates. Depending upon the configuration of the aggregate, antibodies binding Properdin can bind mono, di-, tri- and tetramer, with each generating different responses. Thus antibody-to-properdin ratio can be 1:1, 1:2, 1:3, and 1:4. This means that an antibody can bind in any configuration. An assay can be used to separate antibodies in a rank order according to potency, by the ratio at which they bind Properdin. In other words, antibodies that bind at a 1:1 ratio can be separated from those that bind at a 1:2 ratio, a 1:3 ratio and a 1:4 ratio. A binding ratio of 1:1 suggests that the antibody binding is via one arm and not by two arms. Such antibodies demonstrate a 1:1 binding ratio regardless of whether or not the antibody is a Fab (monovalent) or the IgG (divalent).

Properdin is involved directly in the AP activation but indirectly in classical pathway activation via the amplification loop in vivo. Also, Properdin binds both C3b and C5b. An antibody which disrupts Properdin's interaction with C3b may or may not interrupt Properdin's interaction with C5b (and vice versa). Antibodies that prevent one or both may be of distinguishable clinical significance.

Thus, some antibodies targeting Properdin a) inhibit both the classical pathway and alternative pathway, or b) inhibit the alternative pathway alone. The selected genus of antibodies would only include those antibodies targeting Properdin which acted on Properdin in specifically such a way as to only inhibit the AP, and not the CP.

Anti Human P (Anti-P) Derived from Mouse

The protein Properdin (P) is a large protein with a molecular weight of approximately 50,000. A multitude of antibodies can be produced against various protein motifs of this large protein. Not all, or even most, of these antibodies will necessarily have any therapeutic value. Identification and selection of the appropriate antibody, or antibodies, those with optimal therapeutic value, is crucial.

Two mouse anti-human-P antibodies were selected using a proprietary combination of successive screening methods. The Screening Method enabled this inventor to identify those antibodies which 1) bind to human Properdin, 2) selectively inhibit only the activity of the alternative complement pathway, and 3) interrupt the alternative pathway in such a way as to not disrupt the amplification loop of the classical pathway. These antibodies bind properdin as the target antigen. And they do so in such a way as to inhibit the formation of the P(C3b)n, PC3bB and PC3bBb, and by extension, (Bb)n and C3bBb. The inhibition of these specific complexes is one of the essential and defining common characteristics of all the antibodies of the selected genus. In preventing the formation of these complexes, these antibodies all prevent the alternative pathway's production of C3b, C5a, C5b, and C5b-9, as well as TNF-α, IL-1.

Anti Human P (Anti-P) Derived from Rabbit

Three rabbit anti-human-P antibodies were selected using the Screening Method (the same that was used for selecting the anti-human-P mouse antibodies). As can be seen in FIG.

2, these antibodies inhibit the alternative pathway dependent lysis of rabbit red blood cells (rRBC) in normal human serum (NHS) in buffer that lacks calcium and therefore there is no contribution from the classical complement pathway. In doing so, the effect of these antibodies is targeted, and isolated, to a section of the alternative pathway which does not overlap with the classical pathway. These antibodies prevent the formation of C3a, C3b, C5a, C5b, and C5b-9. The formation of these specific proteins is the critical step in the alternative pathway wherein a normal immune system process can become the source of a pathological condition. It's the overproduction of these proteins from the alternative pathway that often cause arthritic conditions.

The selected alternative pathway specific anti-human-P antibodies generated in rabbits are analogous in effect to those from the mouse models. They are analogous in effect because both the mouse and the rabbit derived antibodies were selected using The Screening Method. They inhibit the formation of C3a, C3b, C5a, C5b, and C5b-9; thereby inhibiting the activation of monocytes, neutrophils, platelets, and the formation of TNF-α (which also plays a key role in inflammation).

Sequences of these anti-properdin rabbit antibodies are very different as shown in the tables noted below. Therefore, looking at the protein sequences alone would not necessarily yield any understanding of their effect on Properdin. Unless tested using the Screening Method, it would be difficult to determine if a given antibody belongs to the selected genus of antibodies. Accordingly, the selected genus of antibodies can't be defined by a specific amino acid sequence. Rather, the genus is defined by the ability of its member antibodies to 1) selectively inhibit AP activation without disrupting any function of the CP, and b) act on a specific part of the AP that is isolated from the CP and which is responsible for AP production of C3a, C3b, C5a, C5b, and C5b-9.

Ba as Target Protein

Anti Human Ba (Anti-Ba) Derived from Mouse

The protein Ba (cleaved from Factor B) is a large protein with a molecular weight of approximately 33,000. Thus, like Properdin and C3b, any of a multitude of antibodies can be produced against various protein motifs of, and locations on, the protein. With this protein, as with the other proteins of the AP, the invention is a selected genus of antibodies which bind to the protein in such a way as to inhibit the formation of C3a, C3b, C5a, C5b, and C5b-9, which are required for the pathological progression of the disease.

As can be seen in FIG. 2, these antibodies inhibit the alternative pathway dependent lysis of rabbit red blood cells (rRBC) in normal human serum (NHS) in a buffer that lacks calcium. The classical pathway can't function in a buffer which lacks calcium. Thus, in these conditions, there is no contribution from the classical complement pathway. Such conditions enable one to observe the effect these antibodies have on the alternative complement pathway in the complete absence of the classical pathway. Observing the antibodies under these conditions is one step of the Screening Method by which the antibodies of the invention are identified.

The sequencing of these anti-alternative pathway antibodies are very different. Thus, here again we observe that the selected genus of antibodies can't be defined by a specific amino acid sequence. Rather, the genus is defined by those which are selected by The Screening Method.

Bb as Target Protein

Anti Human Bb (Anti-Bb) Derived from Mouse

The protein Bb (cleaved product of Factor B) is a large protein with a molecular weight of approximately 64,000. Thus, where again we find that several antibodies can be produced against various protein motifs of this protein. Again we apply the Screening Method in order to produce only those antibodies which have the desired effects. Mouse anti-human-Bb antibodies were raised against factor Bb and therefore would not bind the Ba fragment of the antibody. These monoclonal antibodies were also selected using the Screening Method. They bind Bb and factor B, but not Ba as the target antigen. The selected anti-human-Bb antibodies share the features characteristic of the selected anti-C3b, anti-P, anti-Ba antibodies. Like all of the antibodies from the selected genus of antibodies, these anti-human-Bb antibodies prevent the formation of C3a, C3b, C5a, C5b, and C5b-9 by the alternative pathway. In so doing, these antibodies also prevent the formation of well known markers of inflammation such as TNF-α, IL-1.

Anti Human Bb (Anti-Bb) Derived from Rabbit

Three rabbit anti-Human Bb antibodies were selected using the Screening Method. Members of the selected genus of antibodies which bind Bb do not also bind Ba. Factor B is an integral component of the alternative complement pathway but not the classical complement pathway. Antibodies binding human Bb, which survive The Screening Method, prevent the formation of complexes critical for the propagation of the alternative pathway; C3bB, PC3bB, C3bBb, PC3bBb, P(C3b)n(Bb)n. Like all antibodies of the invention, they prevent the AP induced formation of C3b, C3a, C5b, C5a, and C5b-9, and inhibit the AP at a juncture not shared with the classical pathway. Inhibition of formation of each of these molecules has physiologic consequences. Inhibition of C3b (aC3b) will impact extravascular hemolysis. Inhibition of C3a and C5a will impact cellular activation and subsequent release of inflammatory mediators. Inflammatory mediators, when over-produced, can cause any number of disease pathologies in humans.

As with other antibodies of the selected genus, sequences of these rabbit anti-Bb antibodies are very different. Therefore, looking at the protein sequences alone would not enable one to predict whether such antibodies could have the desired effect.

Table 1 and Table 2 list the amino acid sequences of the heavy and light chains of anti-C3b, anti-P, ant-Ba, and anti-Bb antibodies that were selected using the Screening Method described herein. The Tables identify the heavy chain and light chain CDR1s, CDR2s and CDR3s of the antibodies as well as in the respective frameworks. Accordingly, aspects of the application described herein, relate to an isolated monoclonal antibody, or antigen binding portion thereof comprising: (a) a heavy chain variable region comprising CDR1, CDR2, and CDR3, of the respective antibodies; and (b) a light chain variable region comprising CDR1, CDR2, and CDR3 of the respective antibodies. Other embodiments described herein relate to antibodies that bind to the same epitope on as the VH and VL sequences described in Tables 1 and 2.

TABLE 1

HEAVY CHAIN

| TARGET | SPECIES | CDR1 | CDR2 | CDR3 |
|---|---|---|---|---|
| Properdin | Mouse | GYIFTNYPIH (SEQ ID NO: 1) | FIDPGGGYDEPDERFRD (SEQ ID NO: 2) | RGGGYYLDY (SEQ ID NO: 3) |
| Properdin | Mouse | GFSLSTSGMGVG (SEQ ID NO: 4) | HIWWDDVKSYNPALKS (SEQ ID NO: 5) | IGDGYYSFDY (SEQ ID NO: 6) |
| Properdin | Mouse | GYIFTTYPIH (SEQ ID NO: 7) | FIDPGGGYDEPDDKFRD (SEQ ID NO: 8) | RGDGYYFDY (SEQ ID NO: 9) |
| Properdin | AMGEN | GDSISSGGHYWS (SEQ ID NO: 10) | YIYYSGSSYYNPSLKS (SEQ ID NO: 11) | TGDYFDY (SEQ ID NO: 12) |
| Properdin | AMGEN | GFTFSNYGIH (SEQ ID NO: 13) | VIWYDGNNKYYADSVKG (SEQ ID NO: 14) | GGYYDSRGYYTPYYYYGMDV (SEQ ID NO: 15) |
| Properdin | AMGEN | GFTFSCYGMH (SEQ ID NO: 16) | VIWYDGSNKYYADSVKG (SEQ ID NO: 17) | AGGATAMDV (SEQ ID NO: 18) |
| Properdin | AMGEN | GYTLTELSMH (SEQ ID NO: 19) | GFDPEDGETIYAQMFQG (SEQ ID NO: 20) | GTYYDILTGPSYYYYGLGV (SEQ ID NO: 21) |
| Properdin | AMGEN | GGSISIYYWS (SEQ ID NO: 22) | YIYYSGSTNYNPSLKS (SEQ ID NO: 23) | WNYGDAFDI (SEQ ID NO: 24) |
| Properdin | Rabbit | GFSFSSGYWIF (SEQ ID NO: 25) | GIYSGSSGTTYYANWAKG (SEQ ID NO: 26) | SVDGIDSYDAAFNL (SEQ ID NO: 27) |
| Factor Bb | Mouse | GYTFTNYWIH (SEQ ID NO: 28) | YINPNTGYNDYNQKFKD (SEQ ID NO: 29) | GGQLGLRRAMDY (SEQ ID NO: 30) |
| Factor Bb | Rabbit | GFDLSTYAMS (SEQ ID NO: 31) | AVSATTGNTYYATWAKG (SEQ ID NO: 32) | YASSGVGTYFDL (SEQ ID NO: 33) |
| Factor Bb | Rabbit | GFSLSNYHLG (SEQ ID NO: 34) | VITYGGSTYYASWVKG (SEQ ID NO: 35) | RDSGGYHLDL (SEQ ID NO: 36) |
| Factor Bb | Rabbit | GFSLSSNAIN (SEQ ID NO: 37) | TIHTNTKTYYATWARG (SEQ ID NO: 38) | ADL (SEQ ID NO: 39) |
| Factor C3b | Mouse | GYTFTSYWIN (SEQ ID NO: 40) | DIYPVRGITNYSEKFKN (SEQ ID NO: 41) | GNFGNFDAMDY (SEQ ID NO: 42) |

TABLE 2

Light Chain

| TARGET | SPECIES | CDR1 | CDR2 | CDR3 |
|---|---|---|---|---|
| Properdin | Mouse | RASQDISFFLN (SEQ ID NO: 43) | YTSRYHS (SEQ ID NO: 44) | QHGNTLPWT (SEQ ID NO: 45) |
| Properdin | Mouse | KASQDVSDAVA (SEQ ID NO: 46) | SPSYRYT (SEQ ID NO: 47) | QQHYSTPWT (SEQ ID NO: 48) |
| Properdin | Mouse | RSSQSLVHSNGNTYLH (SEQ ID NO: 49) | RSSQSLVHSNGNTYLH (SEQ ID NO: 50) | SQNTHVPRT (SEQ ID NO: 51) |
| Properdin | AMGEN | RASQDISNYLA (SEQ ID NO: 52) | AASTLQS (SEQ ID NO: 53) | QKYNSAPWT (SEQ ID NO: 54) |
| Properdin | AMGEN | RASQGISNYLA (SEQ ID NO: 55) | AASTLQS (SEQ ID NO: 56) | QKYDSAPWT (SEQ ID NO: 57) |
| Properdin | | | | |
| Properdin | | | | |
| Properdin | | | | |
| Properdin | Rabbit | QASDNIYSLLA (SEQ ID NO: 58) | RASTLAS (SEQ ID NO: 59) | QQHYDYNYLDVA (SEQ ID NO: 60) |

TABLE 2-continued

Light Chain

| TARGET | SPECIES | CDR1 | CDR2 | CDR3 |
|---|---|---|---|---|
| Factor Bb | Mouse | RASKSISKYLA (SEQ ID NO: 61) | SGSTLQS (SEQ ID NO: 62) | QQHDEYPWT (SEQ ID NO: 63) |
| Factor Bb | Rabbit | QASENIYSRLA (SEQ ID NO: 64) | YASDLAS (SEQ ID NO: 65) | HSYYWNSAYSDNT (SEQ ID NO: 66) |
| Factor Bb | Rabbit | QASENIYSYLA (SEQ ID NO: 67) | KASYLAS (SEQ ID NO: 68) | LSTIASASNFDA (SEQ ID NO: 69) |
| Factor Bb | Rabbit | QSSQSVYRSNNVA (SEQ ID NO: 70) | EASSLAS (SEQ ID NO: 71) | AGGYSSSVDFFFA (SEQ ID NO: 72) |
| Factor C3b | Mouse | SATSSITYIH (SEQ ID NO: 73) | DTSRLAS (SEQ ID NO: 74) | QQWSSNPPT (SEQ ID NO: 75) |

In other embodiments, an antibody described herein can comprises heavy and light chain variable regions comprising amino acid sequences that are homologous to the amino acid sequences of the preferred antibodies described herein, and wherein the antibodies retain the desired functional properties. For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to the amino acid sequence of a heavy chain variable region listed in Table 1 for a respective antibody; (b) the light chain variable region comprises an amino acid sequence that is at least 80% homologous to the amino acid sequence of a light chain variable region listed in Table 2 for the respective antibody; and (c) the antibody specifically binds to respective protein, C3b, P, Ba, or Bb.

In various aspects, the antibody can be, for example, a human antibody, a humanized antibody or a chimeric antibody. In other aspects, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding the amino acid sequences, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Thus, such antibodies contain the $V_H$ and $V_L$ CDR sequences described in the Tables yet may contain different framework sequences from these antibodies.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

In general, therapeutic antibodies, once selected, can be manipulated, altered and engineered in a variety of ways for various different reasons. For example, the inactive (non-binding) parts of an selected antibody may be changed and manipulated in countless ways which do not at all change the defining functions of the antibody. In fact, the functional (protein binding part) of the antibody might be entirely severed from the rest of the antibody. These alterations may have utility for making the antibody easier or less costly to produce. Or, such alterations may make the antibody more chemically stable in human subjects. These manipulations and derivations of the selected antibodies are not new or separate inventions. Accordingly, any such manipulations, alternations and derivations of the selected genus of antibodies which utilize the same defining characteristics of the genus itself are within the scope of the invention.

The invention includes compounds which constitute the functional (target protein binding) components of any one or several of the selected genus of antibodies, as well as the therapeutic use such compounds. These compounds include, but are not limited to, whole antibodies of the selected genus, antigen-binding fragments of antibodies of the selected genus, and chimeric or humanized manifestations of any antibody or antibody fragment derived from the selected genus of antibodies. Such derivations of the inventions may include, but are not limited to, truncated, linear, single-chained, an IgG fragment, a F(ab) fragment, a F(ab') fragment, a F(ab)2 fragment, a F(ab')2 fragment, an Fv fragment or an scFv fragment which may be manifested from any antibody of the selected genus.

The invention includes the result of any member of the antibody genus having its Fc region mutated at the 297 position to generate an aglycosylated antibody. The invention includes the results of any antibody of the selected genus being engineered to elicit reduced Fc-mediated effector functions. Methods of engineering may include, without limitation, amino acid mutations, amino acid additions or deletions, glycan modification or removal, pegylation, and/or truncation.

Methods of Administration

The invention provides methods of treatment comprising administering to a subject an effective amount of an embodiment of the invented genus of antibodies. The subject may be an animal (a mammal such as a cow, pig, rat, or monkey) but is preferably a human. Various delivery systems are known and can be used to administer an embodiment of the invention, (e.g., encapsulation in liposomes, microparticles, microcapsules, recombinant cells capable of expressing the compound, receptor-mediated endocytosis, construction of a nucleic acid as part of a retroviral or other vector, etc.). Methods of introduction can be enteral or parenteral and may include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g., daily, weekly, monthly, etc.) or in combination with other agents.

Dosage

Administration of the invented genus of antibodies, and/or any functional derivations thereof, may be by any method known in the art. Such administration may be subcutaneous, intraarticular, intramuscular, intradermal, intraperitoneal, intravenous, intranasal, or via oral routes of administration. In one preferred embodiment, the antibody is administered by subcutaneous injection or intravenous injection. In a specific embodiment, the antibody is administered by subcutaneous injection.

In one embodiment, the amount of AP antibody administered is in a dosage range between 0.3 mg/kg to 30 mg/kg. In a more specific embodiment, the AP antibody is administered once a day in a range between 0.5 mg/kg to 10 mg/kg. In another embodiment, AP antibody is administered in a dosage range between 0.3 mg/kg to 30 mg/kg at least once a week. In yet another embodiment, AP antibody is administered in a dosage range between 0.3 mg/kg to 30 mg/kg at least once a month. Thus, depending upon the AP inhibition profile, administration regimen can be chosen.

Formulation

The compound can be administered to an individual in a formulation with a pharmaceutically acceptable excipient(s). A wide variety of pharmaceutically acceptable excipients are known in the art and need not be discussed in detail herein.

The compound can be incorporated into a variety of formulations for therapeutic administration. In one example, a subject compound can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols.

Formulations can also be developed for subcutaneous, intraperitoneal, intravenous, and intraarticular administration.

Dosing Schedule

A compound of the present invention can be administered to an individual with a certain frequency and for a period of time so as to achieve the desired therapeutic effect. For example, an antibody of the present invention can be administered, for example, once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

AP Specific Antibodies that Inhibit Alternative Pathway (AP)-Dependent Inflammation in Hemolytic Diseases Alternative Pathway in Whole Blood—Inflammation Model There is direct link between C3a/C5a production and activation of neutrophils, monocytes, and platelets and release of a battery of inflammatory cytokines, proteases, and peroxides. In this model, whole blood from a healthy donor is subjected to AP activation via contact as a stimulus. Anaphylatoxin production, cellular activation and measurement of inflammatory cytokines were determined in the presence and absence of antibodies of the current invention. Activation of cells is related to aggregate formation and finally removal from circulation causing cytopenia. AP antibodies of this invention are demonstrated to have a regulatory effect on prevention of activation and cytopenia.

In order to demonstrate the effect of the activation of the alternative pathway in vivo, an ex vivo whole blood inflammation model was used. This model produces effects similar to those exhibited by the cells involved in initiating and perpetuating the inflammatory response. The whole blood system contains the full array of complement proteins and cells responsible for carrying out the ultimate inflammatory response which is the end result of alternative pathway activation. The alternative pathway is triggered in whole blood by contact of the plasma with the artificial surfaces of the polypropylene tubing. Even a simple exposure of the plasma to air can trigger AP activation, and the resultant cellular activation and release of inflammatory mediators. In this model, blood circulation in an artificial system generates complement anaphylatoxins, activated cells, and inflammatory mediators such as TNF-$\alpha$ and IL-1. Multiplex analysis further indicated the production of cytokines such as VEGF, IL-1, IL-17, and several macrophage derived cytokines. These effects in vitro can predict the disease outcome if elevated levels of such components are found in blood or local tissue levels.

Anti-C3b, Anti-Ba, Anti-Bb, and Anti-P antibodies have the potential to down regulate the formation of TNF-$\alpha$ and therefore prevent the onset and progression of the arthritic condition. The therapeutic value of a reduction of TNF-$\alpha$ is a known phenomenon to those of ordinary skill in the art. However, as discussed previously, one skilled in the art cannot predict the outcome of using any given antibody against a given protein in the alternative pathway. Not all Anti-C3b antibodies will have a therapeutic effect. The same is true for Anti-Ba, Anti-Bb and Anti-P antibodies unless selected using the two step process.

AP Specific Antibodies and Cellular Lysis/Inflammation in Humans

In addition to the process of developing the invented genus of antibodies, as well as the resultant genus of antibodies, the invention additionally consists of a method of treating cellular lysis, cellular damage, and inflammation in hemolytic disorders. The method comprises of administering to the afflicted subject a therapeutically effective amount of a compound which is either a member of the invented genus of antibodies, and/or has been derived from such an antibody and utilizes the same AP inhibiting properties as any antibody from the invented genus of antibodies. Such a compound, or compounds, would inhibit the AP processes which lead to the complement activated intravascular and extravascular hemolysis. The antibodies of the claimed invention do not inhibit CP amplification loop and therefore only inhibit AP activation regardless of the target against which they have been made. These antibodies are claimed to inhibit only alternative pathway derived C3b but not classical pathway derived C3b.

In other inventions, the classical pathway can use the amplification of the alternative pathway amplification loop and prevent C3b produced via the classical pathway.

Intravascular Hemolysis—is caused by the deposition of C5b-9 on cell surfaces of erythrocytes. The MAC causes cell lysis. Such a lysis is present on cells that are deficient in CD59. Antibodies of the claimed invention inhibit only AP derived C5b-9 formation and not the classical pathway derived C3b.

Extravascular Hemolysis—is caused by the deposition of C3b on the cell surface. The C3b is responsible for effective removal of cells via extravascular route. The antibodies of the claimed invention inhibit C3b formation and therefore inhibition of alternative pathway mediated removal of cells.

Paroxysmal nocturnal hemoglobinuria ("PNH") and other hemolytic diseases are treated using a antibody of the claimed invention which binds to or otherwise blocks the generation and/or activity of one or more complement components of the alternative pathway and not the classical pathway. Such compounds include, for example, antibodies and fragments of the antibodies which bind to or otherwise block the generation and/or activity of one or more complement components of the alternative pathway but not classical pathway, such as, for example, an antibody specific to complement component C3b, Properdin, Ba, and Bb. The compound is an anti-C3b antibody, an anti-properdin antibody, an anti Ba antibody, and an anti-Bb antibody. Such antibodies are further selected from the group consisting of Anti-C3b (murine, chimeric and humanized), an anti-P antibody (murine, chimeric and humanized), and anti-Ba (murine, chimeric and humanized), and anti-Bb (murine, chimeric, humanized) and other functional fragments of such antibodies. These antibodies are required to have two major functions; a) ability to inhibit C3b and C5b-9 formation.

It was surprising to find that a group of selected antibodies do not inhibit the amplification loop of the classical pathway and therefore do not inhibit the classical pathway in 10% NHS. These antibodies were selected from a set of assays that specifically isolates antibodies that are specific to the alternative pathway. These compounds inhibit the pathway upstream and therefore are a potent inhibitors of C3a, C3b, C5a, C5b, and C5b-9 formation in vitro and in ex vivo in human blood and plasma/serum. Inhibition of C3b formation by such antibodies is important to prevent extravascular hemolysis. Antibodies of this invention prevent C3b formation produced only via the AP but not CP in a dose dependent fashion in human serum and whole blood. Antibodies of this invention also inhibit AP derived C5b-9 and sC5b-9 formation in whole blood and/or serum. Therefore it is surprising that these antibodies do not inhibit any amplification of the classical pathway.

The AP-inhibiting antibodies can be administered prophylactically in individuals known to have a hemolytic disease to prevent, or help prevent the onset of symptoms.

Alternatively, the AP-inhibiting antibodies can be administered as a therapeutic regimen to an individual experiencing symptoms of a hemolytic disease.

In another aspect, a method of increasing the proportion of damage sensitive type III red blood cells and therefore the total red blood cell count in a patient afflicted with a hemolytic disease will increase. The method comprises administering a compound which binds to a specific AP protein and blocks the AP but not the CP. By increasing total number of erythrocytes, symptoms such as fatigue and anemia are alleviated in a patient afflicted with a hemolytic disease.

In another aspect, the present invention provides a method of rendering a subject afflicted with a hemolytic disease, transfusion-independent by administering a compound to the subject. The, compound being selected from the group consisting of anti-C3b, anti-P, anti-Ba, and anti-Bb antibodies and their functionally active antigen binding fragments which bind the AP specific protein, compounds which block the formation of C3b and C5b-9 that block the activity of one or more AP specific proteins.

It is surprising that AP specific antibodies can reduce the lysis of erythrocytes and patients are rendered transfusion-independent in accordance with the present methods. Less C5b-9 formation is directly related to less cellular damage means more cells and patients can become transfusion independent and may not require transfusion.

In another aspect, the present invention contemplates a method of reducing the lysis of red blood cells, the present methods reduce the amount of free hemoglobin in the blood, thereby increasing nitric oxide (NO) and prevention of kidney damage.

In another aspect, the present invention contemplates a method of treating/preventing thrombosis in a subject by administering the antibodies of the claimed invention to prevent platelet activation, platelet lysis, removal of platelets, and formation of platelet aggregates.

In another aspect, the present invention contemplates a method of treating pharmacological effects of preventing cell damage, wherein the cells are selected from the group comprising neutrophils, monocytes, platelets, and T-lymphocytes.

In yet another aspect, the present invention contemplates a method of treating a subject afflicted with a hemolytic disease by administering: 1) one or more compounds known to increase hematopoiesis in combination with 2) a compound selected from the group consisting of compounds that inhibit AP activation by inhibiting C3b formation and C5b-9 formation in a subject. Suitable compounds known to increase hematopoiesis include, for example, steroids, immunosuppressants (such as, cyclosporin), anti-coagulants (such as, warfarin), folic acid, iron and the like, erythropoietin (EPO) and antithymocyte globulin (ATG) and antilymphocyte globulin (ALG). In particularly useful embodiments, erythropoietin (EPO) is administered in combination with an antibody selected from the group consisting of anti-C3b, anti-P, anti-Ba, and anti-Bb antibodies.

In another aspect, the present disclosure provides a method of treating one or more symptoms of hemolytic diseases in a subject where the red cells are subject to complement attack, by administering a compound selected from the group consisting of compounds which bind to AP specific complement components, compounds which block the formation of C3a, C5a, C5b-9 and compounds which block the activity of one or more complement components such as P, Ba, Bb, C3a, C5a, C5b, C6, C7, C8, and C9, said compound being administered alone or in combination with one or more compounds known to increase hematopoiesis.

In another aspect, the methods of the present invention can selectively inhibit the activation of the alternative pathway in a human. The Type-AP antibody can inhibit activation of the alternative pathway without affecting activation of the classical pathway or the amplification loop of the CP.

In another aspect, the alternative pathway specific antibody can be selected from the group comprising, but is not limited to, an anti-C3b antibody, and anti-Factor Ba antibody, an anti-Factor Bb antibody, anti-factor B antibody, an anti-Factor D antibody, or an anti-Properdin antibody.

In a further aspect, the alternative pathway protein that the alternative specific antibody of the present invention can bind to can be selected from the group comprising, but is not limited to, C3b, Factor B, Factor Ba, Factor Bb, Factor D, or Properdin.

In yet another aspect, the methods of the present invention can be used to prevent the formation of byproducts that can form as a result of activation of the alternative pathway in a human. In one example, the methods of the present invention can prevent the formation of anaphylatoxins. Anaphylatoxins include, C3a and C5a. In another example, the methods of the present invention can prevent the formation of C5b-9 or sC5b-9 (otherwise known as MAC). In a further example, the methods of the present invention can prevent the activation of neutrophils, macrophages, and platelets in a subject. In yet another example, the methods of the present invention can prevent the formation of cytokines. Cytokines can include, but are not limited to, IL-1, TNF-α, VEGF, GM-CSF.

In one aspect, the alternative pathway specific antibody of the present invention can be a monoclonal antibody, a polyclonal antibody, an aglycosylated antibody, or an antibody that has one or more mutations.

In another aspect, the alternative pathway specific antibody of the present invention can be selected from the group including, but not limited to, human, humanized, recombinant, chimeric, de-immunized, truncated, aglycosylated, linear, single-chained, an IgG fragment, a F(ab) fragment, a F(ab') fragment, a F(ab)2 fragment, a F(ab')2 fragment, an Fv fragment or an scFv fragment.

In another aspect, the methods of the present invention can include an alternative pathway specific antibody that can have a reduced effector function. Reduced effector functions can include, but are not limited to, reduced Fc binding, lack of Fc activation, an Fc region that contains mutations that prevent the Fc effector functions, or the prevention of activation of platelets and cells that bear Fc receptors.

In another aspect, an effective amount of the alternative pathway specific antibody can be administered to the subject. In one example, the alternative pathway specific antibody or antigen binding fragment thereof can be administered to the subject in a therapeutically effective amount. In another example, the alternative pathway specific antibody or antigen binding fragment thereof can be administered to the subject in a prophylactically effective amount. In a further example the alternative pathway specific antibody can be effective in a therapeutic setting in vivo or ex vivo. In yet another example, the alternative pathway specific antibody can be effective in a prophylactic setting in vivo or ex vivo.

In yet another aspect, the alternative pathway specific antibody of the present invention can contain antigen binding regions termed as complementarity determining regions, or CDRs. In one example, the CDRs of the alternative pathway specific antibody can be present in a fusion protein.

In another example, the CDRs of the alternative pathway specific antibody can be derived from a rabbit alternative pathway specific monoclonal antibody or a mouse alternative pathway specific monoclonal antibody. In a further example, the CDRs of the alternative pathway specific antibody can have greater than 50% homology to the native CDRs of the alternative pathway specific antibody.

AP Specific Antibodies and Other Diseases

The invention genus of antibodies may be used to treat any disease, or disease condition, associated with inappropriate activation, or over activation, of the alternative pathway. Examples of alternative complement pathway associated disorders are numerous. The following is a list of some, but not all, of the diseases, and/or disease symptoms and conditions, which may be ameliorated through administration of the invention genus of antibodies.

Pathologies of the Auditory System—

Ménière's disease, in which complement factors H and B are over-expressed

Pathologies of the Cardiovascular System—

Kawasaki's disease (arteritis) Cardiac surgery complications Henoch-Schonlein purpura nephritis, wherein studies suggest that generation of MAC may be involved in the pathogenesis of vascular injury in a significantly large number of skin lesions and of HSP nephritis, Vascular leakage syndrome (associated with elevated c3a), Percutaneous coronary intervention (PCI)/coronary angioplasty, Ischemia-reperfusion following acute myocardial infarction, Myocardial infarction, which elevates C3 and C4, Atherosclerosis, where C5a is present in atherosclerotic plaques, Immune complex vasculitis, in which MAC alters the membrane integrity of endothelial cells, Arteritis, which contain C3 and C4 deposits, Aneurysm, where it has been shown that C5 inhibition attenuates injury in abdominal aortic aneurysm model, Cardiomyopathy, where c5b-9 activates TNF-α, vasculitis, where it has been shown that C5−/− mice and factor B−/− mice do not develop disease, Takayasu's arteritis, Dilated cardiomyopathy, where c5b-9 activates TNF-α, Venous gas embolus (VGE), Wegener's granulomatosis, Behcet's syndrome, Autoimmune cardiomyopathy, Balloon angioplasty, in which high levels of C5a are associated with restenosis, Myocarditis, where C3a and TNF-α are present, Percutaneous transluminal coronary angioplasty (PTCA), IL-2 induced vascular leakage syndrome, Coronary artery disease (CAD), where there are high C3 levels, Dressler's syndrome (postmyocardial infarction syndrome), in which C3d levels are elevated, Giant cell arteritis (temporal or cranial arteritis), Ischemic heart disease, Ischemia-reperfusion injury, which generates C3a and c5a, Leukocytoclastic vasculitis, in which c3d,g and Terminal complement complexes are present, Mesenteric artery reperfusion, where it has been shown binding C3b attenuates injury, Microscopic polyangiitis, Pauci-immune vasculitis, associated with MAC, c3d, factor P, and factor B, Pulmonary vasculitis, Raynaud phenomenon, Post-ischemic reperfusion conditions, Pulmonary embolisms and infarcts, Restenosis following stent placement, Subacute bacterial endocarditis, where C3d is present Vasculitis associated with rheumatoid arthritis and C3 deposits.

Pathologies of Connective Tissue—

Mixed connective tissue disease and Polymyalgia rheumatica, which C3 and C4 are deposited.

Pathologies of the Skin—

Pemphigoid, Epidermolysis bullosa acquisita, in which Factor B deficient mice display delayed and less severe blistering in a disease model, Autoimmune bullous dermatoses, Bullous pemphigoid, which is associated with C3 and C5, scleroderma, where C5b-9 and C5a receptors are activated, Angioedema, Hereditary angioneurotic edema (HAE), Erythema multiforme, Herpes gestationis, Sjogren's syndrome, with activated c5b-9, Psoriasis, Alopecia areata, Atopic dermatitis (eczema), where levels of C3 and C4 are increased, Cicatricial pemphigoid, Dermatitis herpetiformis, Diffuse systemic sclerosis, Discoid lupus erythematosus, Eosinophilic spongiosis, Erythema nodosum, Lichen planus, Linear iga disease, Localized systemic sclerosis (morphea), Mucha-Habermann disease, Occular cicatricial pemphigoid, Pemphigus, Pemphigus vulgaris, Pyoderma gangrenosum, VitiligoUrticaria.

Pathologies of the Endocrine System—

Hashimoto's thyroiditis, Diabetes mellitus type 1, in which C3, c3d, and C4 levels are increased, Stress anxiety, Pancreatitis, Addison's disease, Insulin resistance, which increases factor H, Diabetic angiopathy Graves' disease.

Conditions Associated with Extracorporeal Procedures—

Post-cardiopulmonary bypass inflammation, Heparin-induced extracorporeal LDL precipitation (HELP), where C5a is increased, Postperfusion syndrome, Post-operative pulmonary dysfunction, Post-pump syndrome in cardiopulmonary bypass or renal bypass, which increases c5b-9, and complement activation during cardiopulmonary bypass operations, hemodialysis, cardiopulmonary bypass, leukopheresis, plasmapheresis, plateletpheresis, and extracorporeal membrane oxygenation (ECMO), which can activate SC5b-9 via alternative pathway.

Pathologies of the Gastrointestinal System—

Crohn's disease, Celiac Disease/gluten-sensitive enteropathy, associated with c3b, Intestinal ischemia, Inflammatory bowel disease (IBD), associated with c5a, Ulcerative colitis, where it has been shown a C5a antibody attenuates damage in colitis model, Eosinophilic gastroenteritis, Gastritis, where levels of c3b, ic3b, and C3c are increased Pancreatitis.

Hematologic Disorders—

Catastrophic anti-phospholipid syndrome (CAPS)[96], Cold Agglutinin Disease (CAD), which increases c3b, Thrombotic thrombocytopenic purpura (TTP), which increases CD46, factor H, and factor I, Idiopathic thrombocytopenic purpura, where C3 and C4 detected are on platelets, Serum sickness, where abnormal factor H leads to increased glomerular C3 deposition, Endotoxemia, Sepsis, Atypical hemolytic uremic syndrome (ahus), where there is enhanced formation of c3bbb convertase and resistance to complement regulators, Paroxysmal Nocturnal Hemoglobinuria (PNH), where it has been shown a C5 antibody treatment reduced thromboembolism risk, Septic shock, sickle cell anemia, which elevates c3b, Hypereosinophilic syndrome, which increases c5a, anti-phospholipid, Autoimmune lymphoproliferative syndrome, Dego's disease, where c5b-9 is activated, Evan's syndrome, essential mixed cryoglobulinemia, and pure red cell aplasia.

Pathologies of the Hepatic System—

Autoimmune chronic active hepatitis, which increase c3d, Infectious hepatitis, Primary biliary cirrhosis inflammation (PBC), associated with higher c1q, C3, factor B, and properdin levels, Primary sclerosing cholangitis, where C3 is increased Autoimmune hepatitis.

Pathologies of Hypersensitivity—

Anaphylactic shock, in which blocking C3a and C5a has shown to be effective therapy, Anaphylactoid reactions from use of radiographic contrast media, adverse drug reaction, Allergy.

Pathologies of the Musculoskeletal System—

Osteoarthritis, Osteoporosis, Acute gouty arthritis, where C6 and MAC are activated, Spondyloarthropathy, Polymyositis, Dermatomyositis, which increases C3b and c5b-C9, Ankylosing spondylitis, associated with increased c3b, Arthritis, where C5a levels rise, Enthesitis-related arthritis, Eosinophilic fasciitis, Juvenile rheumatoid (idiopathic) arthritis, with increased c1q, C4, and MAC, Myositis, Psoriatic arthritis, where it has been shown that anti-C5a prevents arthritis, Reiter's syndrome (reactive arthritis) Relapsing polychondritis.

Pathologies of the Nervous System—

Myasthenia gravis, Multiple sclerosis (MS), Guillain Barre syndrome, which activates C3a and c5a, stroke, where C4 and sC3b-5 is elevated, Cranial nerve damage in meningitis, Variant Creutzfeldt-Jakob disease (vcjd), Neuropathic pain, Alzheimer's disease (AD), where it has been shown that treatment with C5a receptor antagonist reduced pathology, Multifocal motor neuropathy (MMN), Huntington's disease (HD) where there is deposition of C3 and C9 and upregulation of C5a receptors, Amyotrophic lateral sclerosis (ALS), which increases C5a and c5a, Parkinson's disease, degenerative disc disease (DDD), Idiopathic polyneuropathy, allergic neuritis, where C3 depletion can result in less injury, Acute disseminated encephalomyelitis, Acute hemorrhagic leukoencephalitis, Autoimmune peripheral neuropathy, Chronic inflammatory demyelinating polyneuropathy, demyelination, where reduction in C3 and C4 has shown to prevent demyelination, Idiopathic inflammatory demyelinating diseases, Lambert-Eaton myasthenic syndrome, Meningitis, in which C5a is correlated with prognosis and c5ar deficient mice suffered less brain damage, Miller-Fisher syndrome, Neuromyelitis optica (NMO), Perivenous encephalomyelitis, where it has been shown C6 deficient mice are unable to form MAC and exhibit no demyelination, progressive inflammatory neuropathy, opsoclonus myoclonus syndrome, Rasmussen's encephalitis, pediatric autoimmune neuropsychiatric disorders associated with *streptococcus*, stiff person syndrome, Susac syndromeanxiety.

Pathologies of Vision—

Endophthalmitis, where there is higher levels of C3a and C4a in the vitreous, Diabetic retinopathy, where there are C3d and c5b-9 deposits in choriocapillaris, Diabetic retinal microangiopathy, with C5b-9 in the retina, Histoplasmosis of the eye, Purtscher's retinopathy, Age-related macular degeneration (AMD), Dry Age-Related Macular Degeneration (AMD), with elevated c3a, choroidal neurovascularization (CNV), Uveitis, Diabetic macular edema, Pathological myopia, Central retinal vein occlusion (CRVO), Retinal neovascularization, Retinal pigment epithelium (RPE), Choroidal neovascularization (CNY), Dominant drusen, where C3a and C5a promote coronial neurovasculiaztion, Photoreceptor and/or Retinal Pigmented Epithelial (RPE) loss, Stargardt's diseaseScleritis.

Oncological Pathologies—

Hemangiomas, Tumor cell metastasis.

Pathologies of the Renal System—

Glomerulonephritis, Poststreptococcal glomerulonephritis (PSGN), Goodpasture's disease, Membranous nephritis, Berger's Disease/iga nephropathy, Mesangioproliferative glomerulonephritis, where c5b-9 is elevated, Membranoproliferative glomerulonephritis (Dense Deposit Disease), Membranous glomerulonephritis, Renal cortical necrosis (RCN), Renal reperfusion injury, where it has been shown C5 inhibition protects from renal injury, Cryoglobulinemic glomerulonephritis, ABO Incompatible Renal Transplant, Atypical hemolytic uremic syndrome (ahus), Lupus (SLE) nephritis.

Pathologies of the Respiratory System—

Eosinophilic pneumonia, Hypersensitivity pneumonitis, Bronchiecstasis, Reactive airway disease syndrome, where it has been shown C5 and c5ar deficient mice show no airway hyperreactivity, Respiratory syncytial virus (RSV) infection, Parainfluenza virus infection, Rhinovirus infection, Adenovirus infection, Allergic bronchopulmonary aspergillosis (ABPA), Tuberculosis, Parasitic lung disease, Pollution-induced asthma, in which higher C3c and C4 in serum has been shown in children living in polluted areas, Airway hyperresponsiveness (AHR), Adult respiratory distress syndrome, which elevates C3 and c3a, Exercise-induced asthma, Cough variant asthma, occupational asthma, Allergic asthma, Pollen-induced asthma, Severe asthma, Chronic obstructive pulmonary disease (COPD), Emphysema, bronchitis, Cystic fibrosis, Interstitial lung disease, Acute respiratory distress syndrome (ARDS), Transfusion-related acute lung injury (TRALI), Acute lung injury, Byssinosis, Asbestos-induced inflammation, Bronchoconstriction, Fibrosing alveolitis (idiopathic pulmonary fibrosis), which elevates factor Ba, Ischemia/reperfusion acute lung injury, Organic dust diseases, where C3, c3d, and factor B levels increase, Pneumonia, Pathologies caused by inert dusts and minerals (e.g., silicon, coal dust, beryllium, and asbestos).

Systemic Disorders—

Systemic lupus erythematosis (SLE), Rheumatoid arthritis, Acquired Immune Deficiency Syndrome (AIDS), Sarcoid, Systemic inflammatory response syndrome (SIRS), Systemic juvenile rheumatoid arthritis, which elevates Factor Bb and SC5b-9, Castleman's disease, Complement component 2 deficiency, Multiple organ failure, Interleukin-2 induced toxicity during IL-2 therapy, Barraquer-Simons Syndrome (acquired partial lipodystrophy).

Complications of Organ and Tissue Transplants—

Transplant rejection, where it has been shown anti-C5 antibodies improved graft survival, Xenograft rejection, Allotransplantation of organs or grafts, where it has been shown C5 inhibition reduces antibody mediated rejection, Hyperacute rejection, Graft versus host disease, Hyperacute allograft rejection, Presensitized Renal Transplant—Living Donor, Revascularization to transplants and/or replants.

Associated with Trauma—

Hemorrhagic shock, where it has been shown C5a receptor antagonist attenuates multiple organ injury, Hypovolemic shock, Spinal cord injury, Cerebral trauma and/or hemorrhage, Severe burns, where it has been shown C5a blockade improves burn-induced cardiac dysfunction, Frostbite, Crush injury, Wound healing, Brain trauma, Cerebral ischemia reperfusion, which elevates C5 Smoke injury.

Pathologies of the Urogenital and/or Reproductive System—

Spontaneous abortion, Sensory bladder disease, Interstitial cystitis (painful bladder syndrome), Fetomaternal tolerance, Preeclampsia, Sinusitis, Complications of pregnancy, Chronic abacterial cystitis, Hemolysis, elevated liver enzymes, and low platelets (HELLP) syndrome, Infertility, Placental dysfunction and miscarriage and pre-eclampsia, Recurrent fetal loss.

Other Relevant Diseases and Conditions—

Agammaglobulinemia, antisynthetase syndrome, atopic allergy, autoimmune enteropathy, autoimmune inner ear disease, autoimmune polyendocrine syndrome type 1 (Whitaker's syndrome), autoimmune polyendocrine syndrome type 2 (Schmidt syndrome), autoimmune progesterone dermatitis, Balo disease/Balo concentric sclerosis, Vitelliform macular dystrophy (best disease), Bickerstaff's encephalitis, Blau syndrome, Cancer, chemical injury (due to irritant gasses and chemicals, e.g., chlorine, phosgene, sulfur dioxide, hydrogen sulfide, nitrogen dioxide, ammonia, and hydrochloric acid), chronic recurrent multifocal osteomyelitis, Churg-Strauss syndrome, Cogan syndrome, corneal neovascularization, Cushing's syndrome, cutaneous leukocytoclastic angiitis, Dercum's disease, fibrodysplasia ossificans progressiva, fibrogenic dust diseases, gastrointestinal pemphigoid, Hashimoto's encephalitis, hemolytic uremic syndrome (HUS), hemoptysis, hypogammaglobulinemia, immune complex-associated inflammation, ischemia-related retinopathies, lichen sclerosus, lupoid hepatitis, juvenile lymphocytic thyroiditis, Majeed syndrome, malattia leventinese (radial drusen), neuromyotonia, North Carolina macular dystrophy, ord's thyroiditis, palindromic rheumatism, paraneoplastic cerebellar degeneration, parasitic diseases, Parry Romberg syndrome, pars planitis, Parsonage-Turner syndrome, pattern dystrophy, pernicious anaemia, POEMS syndrome, polyarteritis nodosa, proliferative nephritis, restless leg syndrome, retroperitoneal fibrosis, rheumatic fever, rotational atherectomy, Schnitzler syndrome, Sorsby's fundus dystrophy, Still's disease, Surgical trauma, Sydenham chorea, sympathetic ophthalmia, Tolosa-Hunt syndrome, transverse myelitis, undifferentiated spondyloarthropathy, vasculitis associated with systemic lupus erythematosus, vasculitis associated with hepatitis A, von Hippel-Lindau disease (VHL), Whipple's disease, Autoimmune Neutropenia, Chemotherapy, Hemodialysis, Human Immunodeficiency Virus (HIV), Malaria, Epstein Barr Virus, Vitamin Deficiencies, Hypersplenism, Idiopathic Thrombocytopenic Purpura (ITP), Disseminated Intravascular Coagulation (DIC), Post-Transfusion Purpura, Neonatal Allo-Immune Thrombocytopenia, Onyalai, Cyclic Neutropenia, Snake bites, Administration of Interferon, Administration of Tumor Necrosis Factor, administration of Radiotherapy, and application of Corticosteroids.

ITP—ITP is a relatively common hematological disorder defined by low platelet count, normal bone marrow and the absence of other causes of thrombocytopenia. ITP can be diagnosed using standard clinical laboratory tests are used, including: urinalysis, CBC with differential, hematology, coagulation, serum chemistry (includes determining concentration of GM-CSF and soluble GM-CSF), surfactant D, erythrocyte sedimentation rate, and C-reactive protein.

Patients with chronic ITP are identified as at risk for bleeding if platelet the count is less than $30 \times 10^{9/1}$ for those patients not receiving corticosteroids or less than $50 \times 10^9$/L for those patients receiving corticosteroids.

Antibody mediated rejection in organ transplantation, antineutrophil cytoplasmic autoantibody (ANCA) vasculitis, catastrophic antiphospholipid antibody syndrome, dense deposit disease or C3 nephropathy, hemolytic cold agglutinin disease, neuromyelitis optica, nonexudative (dry) macular degeneration, Shiga toxin E. coli-related hemolytic uremic syndrome (STEC-HUS), systemic lupus erythematosus (SLE), thrombotic thrombocytopenic purpura (TTP)

Example 1

Cellular Assay to Demonstrate Inhibition of AP Activation in a Subject Using Exemplary Compounds of the Invention Genus of Antibodies To assess the ability of the exemplary compounds of the present invention to inhibit AP activation in a in vivo-like system, an erythrocyte hemolysis assay was used. Rabbit red blood cells (rRBCs) were incubated with normal human serum (NHS) in an AP enabling buffer. The presence of rRBCs ("the foreign body") preferentially induces activation of the AP, resulting in C5b-9 deposition on the erythrocytes and ultimately causing cell lysis. The extent of cell lysis is detected based on light scattering at optical density of 700 nm. Exemplary compounds of the invention genus of antibodies inhibited hemolysis of rRBCs in a dose dependent manner, as shown in FIGS. 2 and 3.

Introducing rabbit Erythrocytes (rRBC) into 10% human serum (with $Mg^{2+}$/EGTA) represent the introduction of a foreign cell surface which initiates the alternative complement cascade. Activation of the AP results in the formation of MAC which causes lysis of the foreign cells (the rRBCs). The selected antibodies of the present invention prevent lysis of these erythrocytes. This process was quantified after examining the light scattering caused by intact red blood cells.

It is well established that rabbit erythrocytes specifically activate the AP, with a resulting lysis of the rRBCs by the C5b-9 (MAC) complex. A progressive decrease in light scatter (due to lysis of intact cells) was measured at 700 nm as a function of time in a temperature-controlled ELISA plate reader. The data were recorded and analyzed with a SpectraMax® 190 plate reader and SoftMax® Pro software. The results were plotted with MicoCal® Origin Software.

As shown in FIG. 4, anti-C3b, anti-Ba, anti-Bb, and anti-P antibodies of the present invention inhibit AP activation and therefore lysis of rRBC in human serum only under conditions that promotes alternative pathway dependent lysis.

Lysis of cells occurs in several diseases including hemolytic diseases. Inhibition of lysis would provide significant benefit in disease conditions where cell death occurs as a result of production of C5b-9 (FIG. 4). Lysis of cells also is indicative of tissue injury seen in other diseases where role of complement in tissue injury appears to be well established.

Example 2

The Antibody of the Present Invention does not Inhibit the Classical Pathway

To test the activity of the antibodies for CP inhibition, antibody-sensitized, sheep erythrocytes (sRBC) were incubated in 1% normal human serum in CP buffer ($Ca^{2+}$/$Mg^{2+}$). These sRBCs activate the CP, which induces lysis of cell membranes. Lysis of the cell membranes results in a gradual decrease in light scattered by cells. When an alternative pathway specific antibody of the present invention was incubated with sRBCs at 37° C. in 1% NHS with a buffer containing $Ca^{2+}$ and $Mg^{2+}$ ("the CP buffer") no effect on hemolysis was observed within the time period beginning with the start of hemolysis and concluding with maximal hemolysis. This implies that the alternative pathway specific antibody of the present invention does not affect CP hemolytic activity in NHS (FIG. 5) and is not expected to compromise the CP's expected contribution to host defense against pathogens.

Monoclonal antibodies of the present invention, irrespective of the target antigen against which they have been raised, do not inhibit the classical pathway. In a typical assay, antibody sensitized sheep erythrocytes are incubated with Normal Human Serum, with CP buffer containing $Ca^{++}$. These conditions allow for selective activation of the classical pathway. Mechanistically, the antigen-Antibody complex on the surface of the sheep cells activates the classical complement pathway which causes erythrocyte lysis.

As shown in FIG. 5, the representative antibody of the present invention that inhibits the AP but not the CP or the amplification loop of the CP. Development of monoclonal antibodies of this invention will leave the classical pathway intact for host defense against infection.

Lack of inhibition of CP activation by the antibodies of the current genus suggests that host defense will not be compromised as classical pathway is required for host defense. Classical pathway, upon activation, generates C3b which is required for opsonization. In a disease state during AP activation. Thus C3b mediated opsonization is not inhibited by the antibody of this invention.

Example 3

The Antibody of the Present Invention does not Inhibit the Amplification Process Required for the Full Potential of the Classical Pathway A specifically designed assay was used in order to test candidate antibodies for any inhibitory effect on any amplification process which may affect the full potential of the Classical Pathway. In this assay, antibody-sensitized sheep erythrocytes (sRBC) were incubated in 10% normal human serum in CP buffer ($Ca^{2+}/Mg^{2+}$) These sRBCs activate the CP via an antibody-antigen bond complex, which induces lysis of cell membranes. Lysis of cell membranes results in a gradual decrease in light scattered by intact cells. When the alternative pathway specific antibody of the present invention was incubated with sRBCs at 37° C. in $Ca^{2+}$ and $Mg^{2+}$ containing buffer ("the CP buffer") in 10% normal human serum (NHS), no effect on hemolysis was observed (FIG. 2 Panel B) within the time period beginning with the start of hemolysis and concluding with maximal hemolysis. This implies that the alternative pathway specific antibody of the present invention does not affect CP hemolytic activity in NHS and is not expected to compromise the CP's expected contribution to host defense against pathogens. It also implies that the alternative pathway specific antibodies of the present invention do not affect any amplification process which may be required for the full potential of the CP. Accordingly, antibodies of the invention genus are not expected to compromise the CP's full contribution to normal host defense to pathogens.

Monoclonal antibodies of the present invention were evaluated for their effect on the on amplification of the alternative pathway. This was done using an assay of normal human serum (10% NHS with AP isolating $Mg^{2+}$ only buffer) at 37 degree C. with a fixed number of rabbit erythrocytes (Covance) in a temperature controlled ELISA plate reader capable of reading at 700 nm. A progressive decrease in light scatter (due to lysis of intact cells) was measured at 700 nm as a function of time. The data were recorded and analyzed with a SpectraMax® 190 plate reader and SoftMax® Pro software.

As shown in FIG. 2, panel B, the alternative pathway specific antibody of the present invention does not inhibit amplification of the CP which might be initiated by the AP amplification loop. The antibody of the present invention does not inhibit any amplification of the CP (or the CP amplification loop, FIG. 2, panel A) and therefore is a specific inhibitor of the AP. Host defense will remain intact.

Example 4

The Antibody of the Present Invention Inhibits C3b Formation when AP is Activated Alternative pathway activation generates C3b via the cleaving of C3 by AP C3 convertase. C3 is thereby split into C3b and C3a. Antibodies were evaluated for inhibition of C3b using LPS to activate the Alternative Pathway. Microtiter plates were coated with LPS (Lipopolysaccharide from *Salmonella Typhosa*) 2 µg/50 µl in PBS overnight. The wells were incubated with 1% BSA in PBS to block the unoccupied sites on the plate. Following 2 hour incubation at 37 degree, the plate was rinsed with PBS and incubated with Normal human serum (10% final concentration in AP buffer) was mixed with antibodies of the invention and incubated with LPS coated wells. The plate was again incubated for 2 hours 37° C. to allow C3b formation to occur. The plates were extensively washed with PBS, and components of the C3 convertase were detected appropriately with antibodies. We detected C3b with rabbit anti-human C3c at 1:2000 in blocking solution. Following incubation, the plates were rinsed with PBS and prepared with peroxidase labeled goat anti-rabbit at 1:2000 in blocking solution for C3b detection. All plates were developed with TMB following extensive washing with PBS. In the presence of an AP specific antibody of the present invention inhibition of C3b formation was observed.

The alternative pathway specific antibodies of the present invention inhibit formation of C3b produced in excess via the alternative complement pathway. C3b coated cells are generally destroyed via what is known as extravascular hemolysis in PNH disease. Other nucleated cells can be removed as well via the same mechanism. Thus neutropenia, leokopenia and thrombocytopenia are some examples where the end result is the reduction in the number of cells. The genus of antibodies claimed in the current application is expected to prevent the formation of C3b responsible for removal of cells via extravascular route. Extravascular lysis is important in indications such as paroxysmal nocturnal hemoglobinuria where C3b coated erythrocytes are removed from circulation via the unwanted extravascular route.

Shown in FIG. 18 is blood from PNH patient. T lymphocytes are shown in yellow, monocytes are shown in blue, and neutrophils are shown in red. These cells atin with FITC labeled CD45 to stain all leukocytes. Platelets are shown in green. As shown, all cells carry C3b suggesting that it is CD55 may be partly absent on all cells to allow C3b deposition. Antibodies of the current invention would inhibit C3b deposition as shown in FIG. 6.

Example 5

The Antibody of the Present Invention Inhibits C5b-9 Formation in AP Buffer in 10% NHS Alternative pathway activation generates C3b via the cleaving of C3 by AP C3 convertase. C3 is thereby split into C3b and C3a. AP C5 convertase cleaves C5 into C5a and C5b. The C5b molecule inserts itself into the plasma membrane and generates C5b-9 molecules on the cell surface leading to cellular lysis and damage of the cell wall. Antibodies were evaluated for inhibition of C5b-9 using LPS to activate the Alternative Pathway. Microtiter plates were coated with LPS (Lipopolysaccharide from *Salmonella Typhosa*) 2 µg/50 µl in PBS overnight. Following 2 hour incubation at room temperature, the plate was rinsed with PBS and incubated with Normal human serum (10% final concentration in AP buffer) was mixed with antibodies of the invention and incubated with LPS coated wells. The plate was again incubated for 2 hours 37° C. to allow C5b-9 formation to occur. The plates were extensively washed with PBS, and components of the C5b-9 were detected appropriately with neo antibody to C5b-9. We detected C5b-9 with mouse anti-MAC at 1:2000 in blocking solution. All plates were developed with TMB following extensive washing with PBS. In the presence of an AP specific antibody of the present invention inhibition of C5b-9 formation was observed.

As shown in FIG. 7, the alternative pathway specific antibodies of the present invention inhibit formation of C5b-9 produced in excess via the alternative complement pathway. C5b-9 coated cells are destroyed via intravascular hemolysis in PNH disease. Other nucleated cells can be removed as well via the same mechanism. Thus neutropenia, leokopenia and thrombocytopenia are some examples where the end result is the reduction in the number of cells. The genus of antibodies claimed in the current application is expected to prevent the formation of C5b-9 responsible for removal of cells via extravascular route. Extravascular lysis is important in indications such as paroxysmal nocturnal hemoglobinuria where C5b-9 coated erythrocytes are removed from circulation via the intravascular lysis.

As shown in FIG. 10, all Blood cells were stained with CD59 and C5b-9 antibodies. Cells including platelets, neutrophil, monocytes and T lymphocytes are attacked by C5b-9. As shown for each cell type are the plots for CD59 and MAC. In this donor all cells demonstrated a similar pattern and therefore all or one cell type is sufficient to demonstrate the value of this assay for PNH detection and drug monitoring. The ratio of C5b-9 carring cells versus CD59 deficient cells appear to be similar. These cells will be attacked and would be dead. The antibody of the current invention inhibit the formation of C5b-9.

Example 6

Inhibition of Formation of Inflammatory Mediators in Whole Blood Inflammation Model by Compounds (Antibodies of the Current Genus)

Alternative pathway activation generates C3b, which is cleaved from C3 by AP C3 convertase. C3 is cleaved into C3b and C3a. Inhibition of C3b formation has been addressed in Example 5. Formation of C3a is measured using an ELISA (Quidel Corp). Antibodies of the present invention inhibit the formation of C3a. C3a receptors, which bind C3a, are found on monocytes. C3a is known to activate monocyte which release TNF-α, a potent inflammatory cytokine and an inflammatory mediator. TNF-α plays a role in the development and progression of arthritis. Anti-TNF-α therapies alone have provided significant, though incomplete, benefits for patients with various arthritic conditions and diseases, including rheumatoid arthritis and osteoarthritis. Inhibition of C3a formation is directly linked to the inhibition of monocyte activation and inhibition of TNF-α formation and arthritis inflammation.

AP activation in whole blood replicates conditions that are primary to disease induction and progression. Blood inflammation is linked to AP activation and production of inflammatory cytokines. When whole human blood is subjected to AP activation via an artificial trigger, inflammation in whole blood forwards to completion. This includes the formation of anaphylatoxins (e.g., C3a, C5a), the MAC complex (C5b-9/sC5b-9), activation of pro-inflammatory cells such as neutrophils, monocytes and platelets, and formation and release of pro-inflammatory cytokines including TNF-α, IL-1β, IL-6, IL-8, and IL-17.

In this blood inflammation (BI) model, a 2 mL aliquot of freshly isolated heparinized human blood was circulated in polyvinyl chloride tubing at 37° C. for 2 hours. Blood samples following the tubing loop rotation were evaluated for C3a, C5a, and C5b-9/sC5b-9 formation. Additionally inflammation markers such as TNF-α and neutrophil elastase were also measured.

The results shown in FIG. 8 demonstrate that antibodies of the invention inhibit C3a formation. Elevated levels of C3a have been found in several diseases where significant pathology exists. Excessive C3a production results in excessive monocyte activation and a progressively severe pathology. Many diseases where C3a is found elevated can be treated with the antibodies of this invention. Inhibition of C3a suggests inhibition of monocytes activation and inhibition of inflammation in vivo. Thus ex vivo assays are reflective of in vivo inflammation which occurs in other diseases.

Results shown in FIG. 9 demonstrate that antibodies of the invention inhibit C5a formation. C5a activates neutrophils and monocytes by binding their respective receptors on each of these cell types. Activated neutrophils express CD11b and release elastase and are responsible for edema in several models of inflammation. As shown in FIG. 11, the alternative pathway specific antibodies of the present invention inhibit neutrophil activation and, consequently, neutrophil mediated pathological outcomes in vivo. As shown in FIG. 19-25 inhibition of AP activation prevents tissue inflammation, synovitis, bone and cartilage degradation.

Results from FIGS. 11, 12, and 13 show that the antibody of the current invention prevent cellular activation. Activation of all three major cell types is inhibited. Aggregate formation and thrombosis is also inhibited by these antibodies as shown in FIG. 4.

Example 7

The Antibody of the Present Invention Inhibit Hemolysis & LDH In Vivo

Rabbits were injected with PNH cells. The cells lysed over time and released hemoglobin and LDH which was measured by hemoQ and LDH was measured using a kit that measures Lactate dehydrogenase was evaluated. Cytotox® LDH Kit Cat#G1781 and G1782 (Promega, Madison, Wis.) was used for LDH measurement. As shown in FIGS. 16 and 17, the antibody of the current invention inhibits hemoglobin release and release of LDH in vivo. The antibodies of the current invention inhibited erythrocyte lysis and LDH formation in vivo in animals.

It is to be understood that this invention is not limited to particular embodiments described, as such may, of course, vary. It is also to be understood that the terminology used herein is for describing particular embodiments only, and is not intended to be limiting, since the scope of the present invention will be limited only by the appended claims. All patents, patent applications, publications listed or identified in this disclosure are herein incorporated by reference in their entirety.

Having described the invention, the following is claimed:

1. A method of treating a hemolytic disorder in a subject in need thereof, the method comprising administering to the subject a therapeutically effective amount of an antibody that binds to properdin (P), wherein the antibody comprises:
   (1) a light chain variable domain that includes CDR sequences having the sequence of SEQ ID NO:49 (CDR1), SEQ ID NO:50 (CDR2), and SEQ ID NO:51 (CDR3), and a heavy chain variable domain that includes CDR sequences having the sequence of SEQ ID NO:7 (CDR1), SEQ ID NO:8 (CDR2), and SEQ ID NO:9 (CDR3),
   (2) a light chain variable domain that includes CDR sequences having the sequence of SEQ ID NO:52 (CDR1), SEQ ID NO:53 (CDR2), and SEQ ID NO:54 (CDR3), and a heavy chain variable domain that includes CDR sequences having the sequence of SEQ ID NO:10 (CDR1), SEQ ID NO:11 (CDR2), and SEQ ID NO:12 (CDR3),
   (3) a light chain variable domain that includes CDR sequences having the sequence of SEQ ID NO:55 (CDR1), SEQ ID NO:56 (CDR2), and SEQ ID NO:57 (CDR3), and a heavy chain variable domain that includes CDR sequences having the sequence of SEQ ID NO:13 (CDR1), SEQ ID NO:14 (CDR2), and SEQ ID NO:15 (CDR3), or
   (4) a light chain variable domain that includes CDR sequences having the sequence of SEQ ID NO:58 (CDR1), SEQ ID NO:59 (CDR2), and SEQ ID NO:60 (CDR3), and a heavy chain variable domain that includes CDR sequences having the sequence of SEQ ID NO:25 (CDR1), SEQ ID NO:26 (CDR2), and SEQ ID NO:27 (CDR3),
   and selectively inhibits C3a, C5a, C3b, C5b, and C5b-9 produced exclusively by the alternative pathway, without inhibiting the classical pathways ability to produce C3a, C5a, C3b, C5b, and C5b-9.

2. The method of claim 1, the antibody being administered at an amount effective to prevent C3b formation responsible for extravascular hemolysis and C5b-9 responsible for intravascular hemolysis.

3. The method of claim 1, the hemolytic disorder being selected from the group consisting of Paroxysmal Nocturnal Hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, and Neonatal Allo-Immune Thrombocytopenia (NAITP).

4. The method of claim 1, wherein the hemolytic disorder is associated with C3b induced activation of blood cells and the antibody is administered at amount effective to inhibit C3b induced activation of blood cells.

5. The method of claim 4, wherein the activation of blood cells includes neutrophil activation, monocyte activation, platelet activation and T-lymphocyte activation.

6. The method of claim 1, wherein the antibody is administered to the subject with one or more symptoms selected from the group consisting of:
   a. The subject has red blood cells opsonized with C3b;
   b. The subject has leukocytes opsonized with C3b;
   c. The subject has platelets opsonized with C3b;
   d. The subject has anemia;
   e. The subject has higher than normal levels of LDH;
   f. The subject has higher than normal levels of free hemoglobin;
   g. The subject has lower than normal levels of platelets;
   h. The subject has higher than normal levels of reticulocyte counts; and i. The subject has higher than normal levels of bilirubin.

7. The method of claim 6, wherein the antibody reduces all or one of listed symptoms a-i to normal levels.

8. The method of claim 1, wherein the subject is being treated for extravascular hemolysis.

9. A method of treating aberrant cytopenia associated with alternative pathway activation in a subject in need thereof, the method comprising: administering to the subject a therapeutically effective amount of an antibody that binds to properdin (P), wherein the antibody comprises:
   (1) a light chain variable domain that includes CDR sequences having the sequence of SEQ ID NO:49 (CDR1), SEQ ID NO:50 (CDR2), and SEQ ID NO:51 (CDR3), and a heavy chain variable domain that includes CDR sequences having the sequence of SEQ ID NO:7 (CDR1), SEQ ID NO:8 (CDR2), and SEQ ID NO:9 (CDR3),
   (2) a light chain variable domain that includes CDR sequences having the sequence of SEQ ID NO:52 (CDR1), SEQ ID NO:53 (CDR2), and SEQ ID NO:54 (CDR3), and a heavy chain variable domain that includes CDR sequences having the sequence of SEQ ID NO:10 (CDR1), SEQ ID NO:11 (CDR2), and SEQ ID NO:12 (CDR3), (3) a light chain variable domain that includes CDR sequences having the sequence of SEQ ID NO:55 (CDR1), SEQ ID NO:56 (CDR2), and SEQ ID NO:57 (CDR3), and a heavy chain variable domain that includes CDR sequences having the sequence of SEQ ID NO:13 (CDR1), SEQ ID NO:14 (CDR2), and SEQ ID NO:15 (CDR3), or (4) a light chain variable domain that includes CDR sequences having the sequence of SEQ ID NO:58 (CDR1), SEQ ID NO:59 (CDR2), and SEQ ID NO:60 (CDR3), and a heavy chain variable domain that includes CDR sequences having the sequence of SEQ ID NO:25 (CDR1), SEQ ID NO:26 (CDR2), and SEQ ID NO:27 (CDR3), and selectively inhibits C3a, C5a, C3b, C5b, and C5b-9 produced exclusively by the alternative pathway, without inhibiting the classical pathways ability to produce C3a, C5a, C3b, C5b, and C5b-9.

10. The method of claim 9, the aberrant cytopenia being associated with and/or resulting from a hemolytic disorder, the hemolytic disorder being selected from the group consisting of Paroxysmal Nocturnal Hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, and Neonatal Allo-Immune Thrombocytopenia (NAITP).

11. The method of claim 9, wherein the cytopenia includes at least one of leukocytopenia, thrombocytopenia, erythrocytopenia, leukocytopenia, lymphocytopenia, and neutropenia.

12. A method of treating cellular and/or tissue damage caused by alternative complement pathway induced inflammation in a subject, the method comprising administering to the subject a therapeutically effective amount of an antibody that binds to properdin (P), wherein the antibody comprises:

(1) a light chain variable domain that includes CDR sequences having the sequence of SEQ ID NO:49 (CDR1), SEQ ID NO:50 (CDR2), and SEQ ID NO:51 (CDR3), and a heavy chain variable domain that includes CDR sequences having the sequence of SEQ ID NO:7 (CDR1), SEQ ID NO:8 (CDR2), and SEQ ID NO:9 (CDR3), (2) a light chain variable domain that includes CDR sequences having the sequence of SEQ ID NO:52 (CDR1), SEQ ID NO:53 (CDR2), and SEQ ID NO:54 (CDR3), and a heavy chain variable domain that includes CDR sequences having the sequence of SEQ ID NO:10 (CDR1), SEQ ID NO:11 (CDR2), and SEQ ID NO:12 (CDR3), (3) a light chain variable domain that includes CDR sequences having the sequence of SEQ ID NO:55 (CDR1), SEQ ID NO:56 (CDR2), and SEQ ID NO:57 (CDR3), and a heavy chain variable domain that includes CDR sequences having the sequence of SEQ ID NO:13 (CDR1), SEQ ID NO:14 (CDR2), and SEQ ID NO:15 (CDR3), or (4) a light chain variable domain that includes CDR sequences having the sequence of SEQ ID NO:58 (CDR1), SEQ ID NO:59 (CDR2), and SEQ ID NO:60 (CDR3), and a heavy chain variable domain that includes CDR sequences having the sequence of SEQ ID NO:25 (CDR1), SEQ ID NO:26 (CDR2), and SEQ ID NO:27 (CDR3), and selectively inhibits C3a, C5a, C3b, C5b, and C5b-9 produced exclusively by the alternative pathway, without inhibiting the classical pathways ability to produce C3a, C5a, C3b, C5b, and C5b-9.

13. A method of inhibiting lysis of neutrophils, monocytes, platelets, and/or T-lymphocytes in a subject, the method comprising administering to the subject a therapeutically effective amount of an antibody that binds to properdin (P), wherein the antibody comprises:

(1) a light chain variable domain that includes CDR sequences having the sequence of SEQ ID NO:49 (CDR1), SEQ ID NO:50 (CDR2), and SEQ ID NO:51 (CDR3), and a heavy chain variable domain that includes CDR sequences having the sequence of SEQ ID NO:7 (CDR1), SEQ ID NO:8 (CDR2), and SEQ ID NO:9 (CDR3), (2) a light chain variable domain that includes CDR sequences having the sequence of SEQ ID NO:52 (CDR1), SEQ ID NO:53 (CDR2), and SEQ ID NO:54 (CDR3), and a heavy chain variable domain that includes CDR sequences having the sequence of SEQ ID NO:10 (CDR1), SEQ ID NO:11 (CDR2), and SEQ ID NO:12 (CDR3), (3) a light chain variable domain that includes CDR sequences having the sequence of SEQ ID NO:55 (CDR1), SEQ ID NO:56 (CDR2), and SEQ ID NO:57 (CDR3), and a heavy chain variable domain that includes CDR sequences having the sequence of SEQ ID NO:13 (CDR1), SEQ ID NO:14 (CDR2), and SEQ ID NO:15 (CDR3), or (4) a light chain variable domain that includes CDR sequences having the sequence of SEQ ID NO:58 (CDR1), SEQ ID NO:59 (CDR2), and SEQ ID NO:60 (CDR3), and a heavy chain variable domain that includes CDR sequences having the sequence of SEQ ID NO:25 (CDR1), SEQ ID NO:26 (CDR2), and SEQ ID NO:27 (CDR3), and selectively inhibits C3a, C5a, C3b, C5b, and C5b-9 produced exclusively by the alternative pathway, without inhibiting the classical pathways ability to produce C3a, C5a, C3b, C5b, and C5b-9 at levels sufficient to maintain normal host defense.

14. The method of claim 13, the lysis being associated with and/or resulting from a hemolytic disorder, the hemolytic disorder being selected from the group consisting of Paroxysmal Nocturnal Hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, and Neonatal Allo-Immune Thrombocytopenia (NAITP).

15. A method of inhibition alternative pathway platelet activation and dysfunction in a subject in need thereof, the method comprising administering to the subject the method comprising administering to the subject a therapeutically effective amount of an antibody that binds to properdin (P), wherein the antibody comprises:

(1) a light chain variable domain that includes CDR sequences having the sequence of SEQ ID NO:49 (CDR1), SEQ ID NO:50 (CDR2), and SEQ ID NO:51 (CDR3), and a heavy chain variable domain that includes CDR sequences having the sequence of SEQ ID NO:7 (CDR1), SEQ ID NO:8 (CDR2), and SEQ ID NO:9 (CDR3), (2) a light chain variable domain that includes CDR sequences having the sequence of SEQ ID NO:52 (CDR1), SEQ ID NO:53 (CDR2), and SEQ ID NO:54 (CDR3), and a heavy chain variable domain that includes CDR sequences having the sequence of SEQ ID NO:10 (CDR1), SEQ ID NO:11 (CDR2), and SEQ ID NO:12 (CDR3), (3) a light chain variable domain that includes CDR sequences having the sequence of SEQ ID NO:55 (CDR1), SEQ ID NO:56 (CDR2), and SEQ ID NO:57 (CDR3), and a heavy chain variable domain that includes CDR sequences having the sequence of SEQ ID NO:13 (CDR1), SEQ ID NO:14 (CDR2), and SEQ ID NO:15 (CDR3), or (4) a light chain variable domain that includes CDR sequences having the sequence of SEQ ID NO:58 (CDR1), SEQ ID NO:59 (CDR2), and SEQ ID NO:60 (CDR3), and a heavy chain variable domain that includes CDR sequences having the sequence of SEQ ID NO:25 (CDR1), SEQ ID NO:26 (CDR2), and SEQ ID NO:27 (CDR3), and selectively inhibits C3a, C5a, C3b, C5b, and C5b-9 produced exclusively by the alternative pathway, without inhibiting any of the classical pathways ability to produce C3a, C5a, C3b, C5b, and C5b-9.

16. The method of claim 15, the platelet activation and dysfunction being associated with and/or resulting from a hemolytic disorder, the hemolytic disorder being selected from the group consisting of Paroxysmal Nocturnal Hemoglobinuria (PNH), Idiopathic Thrombocytopenic Purpura (ITP), Thrombotic Thrombocytopenic Purpura (TTP), Hemolytic-Uremic Syndrome (HUS), Disseminated Intravascular Coagulation (DIC), Antiphospholipid Syndrome (APS), Post-Transfusion Purpura, and Neonatal Allo-Immune Thrombocytopenia (NAITP).

* * * * *

UNITED STATES PATENT AND TRADEMARK OFFICE
CERTIFICATE OF CORRECTION

PATENT NO. : 9,926,366 B2  
APPLICATION NO. : 14/433587  
DATED : March 27, 2018  
INVENTOR(S) : Rekha Bansal Page 1 of 1

It is certified that error appears in the above-identified patent and that said Letters Patent is hereby corrected as shown below:

In the Claims

Column 73, Line 58, in Claim 1, replace "pathways ability" with --pathway's ability--.

Column 75, Line 21, in Claim 9, replace "pathways ability" with --pathway's ability--.

Column 76, Line 6, in Claim 12, replace "pathways ability" with --pathway's ability--;

Line 45, in Claim 13, replace "pathways ability" with --pathway's ability--.

Column 78, Line 7, in Claim 15, replace "pathways ability" with --pathway's ability--.

Signed and Sealed this  
Thirty-first Day of July, 2018

Andrei Iancu  
*Director of the United States Patent and Trademark Office*